United States Patent
Araki et al.

(10) Patent No.: US 7,476,685 B2
(45) Date of Patent: Jan. 13, 2009

(54) PYRIDINE CARBOXAMIDE DERIVATIVES AND THEIR USE AS PESTICIDES

(75) Inventors: Koichi Araki, Ibaraki (JP); Tetsuya Murata, Ibaraki (JP); Koshi Gunjima, Yachiyo (JP); Norihiko Nakakura, Tochigi (JP); Eiichi Shimojo, Tochigi (JP); Christian Arnold, Adendorf (DE); Waltraud Hempel, Liederbach (DE); Daniela Jans, Bad Homburg v. d. H. (DE); Olga Malsam, Bonn (DE); Jutta Maria Waibel, Frankfurt (DE)

(73) Assignee: Merial Limited, Duluth, GA (US)

( * ) Notice: Subject to any disclaimer, the term of this patent is extended or adjusted under 35 U.S.C. 154(b) by 243 days.

(21) Appl. No.: 10/514,485

(22) PCT Filed: May 6, 2003

(86) PCT No.: PCT/EP03/04714

§ 371 (c)(1),
(2), (4) Date: Sep. 26, 2005

(87) PCT Pub. No.: WO03/097604

PCT Pub. Date: Nov. 27, 2003

(65) Prior Publication Data

US 2006/0166991 A1    Jul. 27, 2006

(30) Foreign Application Priority Data

May 16, 2002    (EP)    .................... 02010910

(51) Int. Cl.
*A01N 43/40*    (2006.01)
*C07D 213/82*    (2006.01)
(52) U.S. Cl. ........................ 514/355; 546/316
(58) Field of Classification Search ............. 546/316; 514/355
See application file for complete search history.

(56) References Cited

U.S. PATENT DOCUMENTS

| 5,360,806 A * | 11/1994 | Toki et al. ................. 514/318 |
| 2002/0032328 A1 | 3/2002 | Shermolovich et al. |
| 2004/0167334 A1 | 8/2004 | Shermolovich et al. |

FOREIGN PATENT DOCUMENTS

| DE | 1 99 58 166 A | 12/2000 |
| DE | 100 14 006 A1 | 9/2001 |
| EP | 0 580 374 A1 | 1/1994 |

OTHER PUBLICATIONS

Database WPI, Week 0214, AN 106161 (2002), Derwent Publications Ltd., London, GB (abstract of WO 2001/90075 A published Nov. 29, 2001).
Database WPI, Week 0125, An 244289 (2001). Derwent Publications Ltd., London, GB (abstract of WO 2001/14340 A published Mar. 1, 2001).

* cited by examiner

*Primary Examiner*—Patricia L Morris
(74) *Attorney, Agent, or Firm*—Judy Jarecki-Black; Merial Limited; Thomas Kowalski, Esq

(57) ABSTRACT

The invention relates to 3-pyridylcarboxamide derivatives of the formula (I):

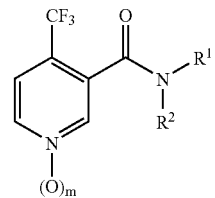

wherein the various symbols are as defined in the description, compositions thereof, methods for controlling pests by applying same, and processes for their preparation.

9 Claims, No Drawings

PYRIDINE CARBOXAMIDE DERIVATIVES AND THEIR USE AS PESTICIDES

CROSS-REFERENCE TO RELATED APPLICATIONS

This application is the U.S. national stage of International Appln. No. PCT/EP2003/004714, filed May 6, 2003, and claims priority under 35 U.S.C. § 119(a)-(d) of European Patent Application No. 02010910.4, filed May 16, 2002, said applications being incorporated by reference herein in their entireties and relied upon.

The invention relates to 3-pyridylcarboxamide derivatives and their use for the control of pests, in particular arthropods such as insects and acarids, and helminths (including nematodes); to compositions containing them, and to processes and intermediates for their preparation.

The control of insects, nematodes or helminths with 3-pyridylcarboxamide compounds has been described in many patents such as EP 580374, JP 10101648, JP 10182625, WO 200109104, WO 200114340, JP 6321903, JP 10195072 and JP 11180957.

However, the level of action and/or duration of action of these prior-art compounds is not entirely satisfactory in all fields of application, in particular against certain organisms or when low concentrations are applied.

Since modern pesticides must meet a wide range of demands, for example regarding level, duration and spectrum of action, use spectrum, toxicity, combination with other active substances, combination with formulation auxiliaries or synthesis, and since the occurrence of resistances is possible, the development of such substances can never be regarded as concluded, and there is constantly a high demand for novel compounds which are advantageous over the known compounds, at least as far as some aspects are concerned.

It is an object of the present invention to provide compounds which widen the spectrum of the pesticides in various aspects.

The present invention provides a compound which is a 3-pyridylcarboxamide derivative of formula (I):

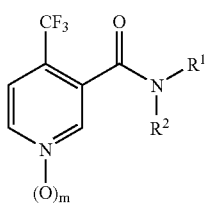

(I)

wherein:
$R^1$ is —C(=U)NR$^3$R$^4$ or —C(=V)OR$^{3a}$;
$R^2$ is H, $(C_1-C_6)$alkyl or $R^3$;
$R^3$ is $R^5$, OH or NH$_2$; or is $(C_1-C_6)$alkyl substituted by one or more $R^6$ groups;
or $R^2$ and $R^3$ together with the interconnecting atoms form a heterocyclic ring selected from (A), (B), (C), (D) and (E);

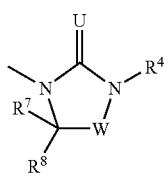

(A)

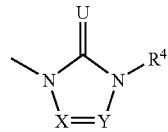

(B)

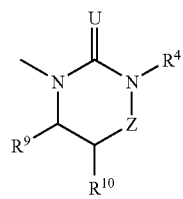

(C)

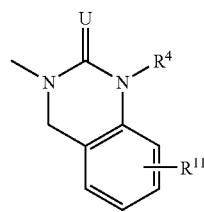

(D)

(E)

$R^{3a}$ is $(C_3-C_8)$cycloalkyl or $(C_3-C_8)$cycloalkyl-$(C_1-C_6)$alkyl, which cycloalkyl groups are unsubstituted or substituted by one or more $(C_1-C_6)$alkyl, $(C_1-C_6)$haloalkyl or $R^6$ groups; or is $(C_1-C_6)$alkyl, $(C_3-C_6)$alkenyl or $(C_3-C_6)$alkynyl which last three mentioned groups are substituted by one or more $R^6$ groups; or is $(C_1-C_6)$alkylamino;
or is NH(CHR$^{14}$)$_s$aryl which aryl group is unsubstituted or substituted by one or more $R^6$ groups;

$R^4$ is H or $R^5$; or is $(C_1-C_6)$alkyl unsubstituted or substituted by one or more $R^6$ groups;
or $R^3$ and $R^4$ together with the adjacent N atom form a 3 to 8-membered unsaturated, partially saturated or saturated heterocyclic ring which optionally contains up to three additional N, O or S atoms and which ring is unsubstituted or substituted by one or more $R^6$ or $R^{14a}$ groups (preferred examples of such ring systems include pyrrolidin-1-yl, pyrrolin-1-yl, piperidin-1-yl, morpholin-1-yl (or its N-oxide), thiomorpholin-1-yl (or its S-oxide or S,S-dioxide), 4,5-dihydropyrazol-1-yl or pyrazol-1-yl);

$R^5$ is $(C_3-C_6)$alkenyl, $(C_3-C_6)$alkynyl, $(C_3-C_8)$cycloalkyl, $(C_1-C_6)$alkoxy, $(C_3-C_6)$alkenyloxy, $(C_3-C_6)$alkynyloxy, $(C_1-C_6)$alkylamino, di-$(C_1-C_6)$alkylamino, CO$(C_1-C_6)$alkyl, NHCO$(C_1-C_6)$alkyl, NHSO$_2$$(C_1-C_6)$alkyl or SO$_2$$(C_1-C_6)$alkyl which last 12 mentioned groups are unsubstituted or substituted by one or more $R^6$ groups; or is $(C_3-C_8)$cycloalkyl-$(C_1-C_6)$alkyl which cycloalkyl group is unsubstituted or substituted by one or more $R^6$ groups; or is NH(CHR$^{14}$)$_s$aryl, —(CR$^{15}$R$^{16}$)$_p$aryl, O(R$^{15}$R$^{16}$)$_r$aryl, NHCOaryl, CO(CH$_2$)$_t$aryl, NHSO$_2$aryl, SO$_2$(CH$_2$)$_u$aryl or N=C(aryl)$_2$, —(CR$^{15}$R$^{16}$)$_p$heterocyclyl or O(R$^{15}$R$^{16}$)$_r$heterocyclyl, which last ten mentioned aryl or heterocyclyl groups are unsubstituted or substituted by one or more $R^{17}$ groups; or is $O(CR^{15}R^{16})_p(C_3-C_8)$cycloalkyl or $N=C[(C_1-C_6)alkyl]_2$;

$R^6$ is halogen, $(C_1-C_6)$alkoxy, $(C_1-C_6)$haloalkoxy, $S(O)_n R^{14a}$, CN, $CO_2(C_1-C_6)$alkyl, $CO_2H$, $NO_2$, OH, amino, $(C_1-C_6)$alkylamino, di-$(C_1-C_6)$alkylamino, carbamoyl, $(C_1-C_6)$-alkylcarbamoyl, di-$(C_1-C_6)$-alkylcarbamoyl or $CH[O(C_1-C_6)alkyl]_2$; or is phenoxy unsubstituted or substituted by one or more $R^{14a}$ or halogen groups;

$R^{17}$ is $R^6$, $R^{14a}$ or $CH_2OH$;

U is S, O or $NR^{18}$;

V is O or S;

W is $(CHR^{19})_q$, CO or $NR^{20}$;

X is $CR^{21}$ or N;

Y is $CR^{22}$ or N;

Z is O, CO or $NR^{23}$;

$R^7$, $R^8$, $R^9$, $R^{12}$, $R^{19}$, $R^{21}$ and $R^{22}$ are each independently H; or $(C_1-C_6)$alkyl, $(C_2-C_6)$alkenyl, $(C_2-C_6)$alkynyl, $(C_3-C_8)$cycloalkyl, $(C_1-C_6)$alkoxy, $(C_2-C_6)$alkenyloxy or $(C_2-C_6)$alkynyloxy, which last seven mentioned groups are unsubstituted or substituted by one or more $R^6$ groups; or is —$(CH_2)_p$aryl or heterocyclyl, which aryl or heterocyclyl groups are unsubstituted or substituted by one or more $R^6$ groups; or $(C_3-C_8)$cycloalkyl-$(C_1-C_6)$alkyl which cycloalkyl group is unsubstituted or substituted by one or more $R^6$ groups;

or $R^7$ and $R^8$ together with the attached carbon atom may represent C=O;

$R^{10}$, $R^{20}$ and $R^{23}$ are each independently H; or $(C_1-C_6)$alkyl, $(C_3-C_6)$alkenyl, $(C_3-C_6)$alkynyl or $(C_3-C_8)$cycloalkyl, which last four mentioned groups are unsubstituted or substituted by one or more $R^6$ groups; or is $(C_3-C_8)$cycloalkyl-$(C_1-C_6)$alkyl which cycloalkyl group is unsubstituted or substituted by one or more $R^6$ groups; or is —$(CH_2)_p$aryl or heterocyclyl which aryl or heterocyclyl groups are unsubstituted or substituted by one or more $R^6$ groups;

$R^{11}$ is $R^7$, halogen, CN, $CO_2(C_1-C_6)$alkyl, $NO_2$ or $S(O)_n R^{14}$; or is $(C_1-C_6)$alkylamino or di-$(C_1-C_6)$alkylamino, which groups are unsubstituted or substituted by one or more $R^6$ groups;

$R^{13}$ is $R^7$ or OH;

$R^{14}$, $R^{15}$ and $R^{16}$ are each independently H, $(C_1-C_6)$alkyl or $(C_1-C_6)$haloalkyl;

$R^{14a}$ is $(C_1-C_6)$alkyl or $(C_1-C_6)$haloalkyl;

$R^{18}$ is $R^7$ or OH; or is $(C_1-C_6)$alkylamino or di-$(C_1-C_6)$alkylamino, which groups are unsubstituted or substituted by one or more $R^6$ groups;

m is zero or one;

n, p, r, s, t and u are each independently zero, one or two;

q is one, two or three; and each heterocyclyl in the above mentioned radicals is independently a heterocyclic radical having 3 to 7 ring atoms and 1 to 4 hetero atoms selected from N, O and S;

or a pesticidally acceptable salt thereof;

with the exclusion of the compound wherein $R^1$ is —C(=U)$NR^3R^4$; U is O; $R^2$ is H; m is zero; $R^4$ is H and $R^3$ is 2,4-dichlorophenyl.

These compounds possess valuable pesticidal properties.

The invention also encompasses any stereoisomer, enantiomer or geometric isomer, and mixtures thereof.

By the term "pesticidally acceptable salts" is meant salts the cations or anions of which are known and accepted in the art for the formation of salts for pesticidal use. Suitable salts with bases, e.g. formed by compounds of formula (I) containing a carboxy or OH group, include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Suitable acid addition salts, e.g. formed by compounds of formula (I) containing an amino group, include salts with inorganic acids, for example hydrochlorides, sulphates, phosphates and nitrates and salts with organic acids for example acetic acid.

The term pests means arthropod pests (including insects and acarids), and helminths (including nematodes).

In the present patent specification, including the accompanying claims, the aforementioned substituents have the following meanings:

halogen atom means fluorine, chlorine, bromine or iodine;

alkyl groups and portions thereof (unless otherwise defined) may be straight- or branched-chain;

cycloalkyl groups preferably have from three to six carbon atoms in the ring and are optionally substituted by halogen or alkyl.

The haloalkyl and haloalkoxy groups can bear one or more halogen atoms; preferred groups of this type include —$CF_3$ and —$OCF_3$.

The term "halo" before the name of a radical means that this radical is partially or completely halogenated, that is to say, substituted by F, Cl, Br, or I, in any combination, preferably by F or Cl.

The expression "$(C_1-C_6)$-alkyl" is to be understood as meaning an unbranched or branched hydrocarbon radical having 1, 2, 3, 4, 5 or 6 carbon atoms, such as, for example a methyl, ethyl, propyl, isopropyl, 1-butyl, 2-butyl, 2-methylpropyl or tert-butyl radical.

"$(C_1-C_6)$-Haloalkyl" is to be understood as meaning an alkyl group mentioned under the expression "$(C_1-C_6)$-alkyl" in which one or more hydrogen atoms are replaced by the same number of identical or different halogen atoms, preferably by chlorine or fluorine, such as the trifluoromethyl, the 1-fluoroethyl, the 2,2,2-trifluoroethyl, the chloromethyl, fluoromethyl, the difluoromethyl or the 1,1,2,2-tetrafluoroethyl group.

"$(C_1-C_6)$-Alkoxy" is to be understood as meaning an alkoxy group whose hydrocarbon radical has the meaning given under the expression "$(C_1-C_6)$-alkyl".

The terms "alkenyl" and "alkynyl" with a range of carbon atoms stated as prefix denote a straight-chain or branched hydrocarbon radical having a number of carbon atoms which corresponds to this stated range and which contains at least one multiple bond which can be located in any position of the respective unsaturated radical. "$(C_2-C_6)$-Alkenyl" accordingly denotes, for example, the vinyl, allyl, 2-methyl-2-propenyl, 2-butenyl, pentenyl, 2-methylpentenyl or the hexenyl group. "$(C_2-C_6)$-Alkynyl" denotes, for example, the ethynyl, propargyl, 2-methyl-2-propynyl; 2-butynyl; 2-pentynyl or the 2-hexynyl group.

"$(C_3-C_8)$-Cycloalkyl" denotes monocyclic alkyl radicals, such as the cyclopropyl, cyclobutyl, cyclopentyl, cyclohexyl, cycloheptyl or cyclooctyl radical, and denotes bicyclic alkyl radicals, such as the norbornyl radical.

The expression "$(C_3-C_8)$-cycloalkyl-$(C_1-C_6)$-alkyl" is to be understood as meaning, for example the cyclopropylmethyl, cyclopentylmethyl, cyclohexylmethyl, cyclohexylethyl, cyclohexylbutyl, 1-methylcyclopropyl, 1-methylcyclopentyl, 1-methylcyclohexyl, 3-hexylcyclobutyl or the 4-tert-butylcyclohexyl radical.

"$(C_1-C_6)$-Alkylamino" denotes a nitrogen atom which is substituted by an alkyl radical of the above definition. "Di-$(C_1-C_6)$-alkylamino" denotes a nitrogen atom which is substituted by two alkyl radical of the above definition.

The expression "$(C_1-C_6)$-alkylcarbamoyl" denotes a carbamoyl group having one hydrocarbon radical which has the meaning given under the expression "($C_1$-$C_6$)-alkyl"; and "di-($C_1$-$C_6$)-alkylcarbamoyl" denotes a carbamoyl group having two hydrocarbon radicals which can be identical or different.

The expression "aryl" is to be understood as meaning a carbocyclic, i.e. constructed of carbon atoms, aromatic radical having preferably 6 to 14, in particular 6 to 12, carbon atoms, such as, for example, phenyl, naphthyl or biphenylyl, preferably phenyl.

The expression "heterocyclyl" preferably denotes a cyclic radical which can be completely saturated, partially unsaturated or completely unsaturated and which contains in the ring one or more identical or different atoms selected from the group consisting of nitrogen, sulfur and oxygen, where, however, two oxygen atoms may not be directly adjacent and at least one carbon atom has to be present in the ring, such as, for example, a thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine, 4H-quinolizine, piperidine, pyrrolidine, oxazoline, tetrahydrofuran, tetrahydropyran, isoxazolidine, thiazolidine, oxirane or oxetane radical.

Heterocyclyl preferably denotes a saturated, partially saturated or aromatic ring system having 3 to 7 ring members and 1 to 4 heteroatoms selected from the group consisting of O, S and N, where at least one carbon atom has to be present in the ring.

More preferably, heterocyclyl denotes a pyridine, pyrimidine, (1,2,4)-oxadiazole, (1,3,4)-oxadiazole, (1,3,4)-thiadiazole, (1,2,4)-thiadiazole, pyrrole, furan, thiophene, oxazole, thiazole, benzothiazole, imidazole, pyrazole, isoxazole, 1,2,4-triazole, tetrazole, pyrimidine, pyrazine, pyridazine, oxazoline, thiazoline, tetrahydrofuran, tetrahydropyran, morpholine, piperidine, piperazine, pyrroline, pyrrolidine, oxazolidine or thiazolidine radical (particularly a pyridine, pyrimidine, (1,2,4)-oxadiazole, (1,3,4)-oxadiazole, (1,3,4)-thiadiazole, 1,2,4-thiadiazole, thiazole, pyrazole, pyrrole, isoxazole, benzothiazole, 1,2,4-triazole, pyrazine, pyridazine, oxirane or oxetane radical).

Preferred substituents for the various aliphatic, aromatic and heterocyclic ring systems include halogen, nitro, cyano, ($C_1$-$C_4$)-alkyl, ($C_3$-$C_6$)-cycloalkyl, ($C_1$-$C_4$)-alkoxy, ($C_1$-$C_4$)-alkylthio, ($C_1$-$C_4$)-alkylsulfinyl, ($C_1$-$C_4$)-alkylsulfonyl, phenyl, benzyl or phenoxy, where in the alkyl radicals and the radicals derived therefrom one or more—and in the case of fluorine up to the maximum number of—hydrogen atoms can be replaced by halogen, preferably chlorine or fluorine.

More preferred substituents include halogen, nitro, cyano, ($C_1$-$C_4$)-alkyl, ($C_1$-$C_4$)-haloalkyl, ($C_3$-$C_6$)-cycloalkyl, ($C_1$-$C_4$)-alkoxy, ($C_1$-$C_4$)-haloalkoxy, ($C_1$-$C_4$)-alkylthio or ($C_1$-$C_4$)-haloalkylthio.

Most preferred substituents include halogen, nitro, cyano, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio or ($C_1$-$C_4$)-haloalkylthio.

It is to be generally understood, unless otherwise stated, that the term "unsubstituted or substituted by one or more groups" or "unsubstituted or substituted by one or more groups selected from" means that such groups (or preferred groups) may be the same or different.

$R^1$ is preferably —C(=U)NR$^3$R$^4$;

$R^2$ is preferably H or $R^3$ (more preferably $R^2$ is H);

$R^3$ is preferably $R^5$ or OH; or is ($C_1$-$C_6$)alkyl substituted by one or more $R^6$ groups;

or preferably $R^2$ and $R^3$ together with the interconnecting atoms form a heterocyclic ring selected from (A) and (C):

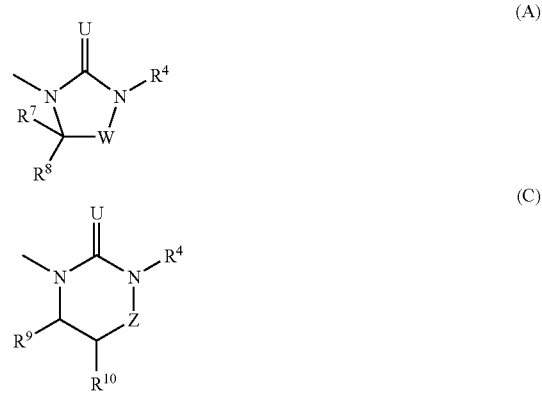

$R^4$ is preferably H or $R^5$, or is ($C_1$-$C_6$)alkyl unsubstituted or substituted by one or more $R^6$ groups;

or $R^3$ and $R^4$ together with the adjacent N atom may form a 3 to 8-membered unsaturated, partially saturated or saturated heterocyclic ring which optionally contains up to three additional N, O or S atoms and which ring is unsubstituted or substituted by one or more $R^6$ or $R^{14a}$ groups (particularly preferred examples of such ring systems include pyrrolidin-1-yl, piperidin-1-yl, morpholin-1-yl, thiomorpholin-1-yl or its S-oxide or S,S-dioxide);

$R^5$ is preferably ($C_3$-$C_6$)alkenyl, ($C_3$-$C_6$)alkynyl, ($C_3$-$C_8$)cycloalkyl, ($C_3$-$C_8$)cycloalkyl-($C_1$-$C_6$)alkyl, ($C_1$-$C_6$)alkoxy, ($C_3$-$C_6$)alkenyloxy, ($C_3$-$C_6$)alkynyloxy or O(CR$^{15}$R$^{16}$)$_p$($C_3$-$C_8$)cycloalkyl; or is —(CR$^{15}$R$^{16}$)$_p$phenyl, —(CR$^{15}$R$^{16}$)$_p$heterocyclyl, O(CR$^{15}$R$^{16}$)$_r$phenyl or O(CR$^{15}$R$^{16}$)$_r$heterocyclyl, which last four mentioned phenyl or heterocyclyl groups are unsubstituted or substituted by one or more $R^{17}$ groups; (more preferably $R^5$ is ($C_3$-$C_6$)alkenyl, ($C_3$-$C_6$)alkynyl, ($C_1$-$C_6$)alkoxy, ($C_3$-$C_6$)alkenyloxy, ($C_3$-$C_6$)alkynyloxy or O(CR$^{15}$R$^{16}$)$_p$($C_3$-$C_8$)cycloalkyl; or is —(CR$^{15}$R$^{16}$)$_p$phenyl, —(CR$^{15}$R$^{16}$)$_p$heterocyclyl, O(CR$^{15}$R$^{16}$)$_r$phenyl or O(CR$^{15}$R$^{16}$)$_r$heterocyclyl, which last four mentioned phenyl or heterocyclyl groups are unsubstituted or substituted by one or more $R^{17}$ groups);

$R^6$ is preferably halogen, ($C_1$-$C_6$)alkoxy, ($C_1$-$C_6$)haloalkoxy, S(O)$_n$R$^{14a}$, CN, NO$_2$ or OH; (more preferably $R^6$ is halogen or CN);

$R^{17}$ is preferably $R^6$, $R^{14a}$ or CH$_2$OH;

U is preferably S or O;

W is preferably (CHR$^{19}$)$_q$ or CO;

Z is preferably O;

$R^7$, $R^8$, $R^9$, $R^{10}$ and $R^{19}$ are each preferably H; or ($C_1$-$C_6$)alkyl unsubstituted or substituted by one or more $R^6$ groups;

or $R^7$ and $R^8$ together with the attached carbon atom represent C=O;

$R^{14}$, $R^{15}$ and $R^{16}$ are each preferably H or ($C_1$-$C_6$)alkyl;

$R^{14a}$ is preferably ($C_1$-$C_6$)alkyl or ($C_1$-$C_6$)haloalkyl;

m is preferably zero;

n, r, s, t and u are preferably zero or one;

q is preferably one; and heterocyclyl preferably denotes a pyridine, pyrimidine, (1,2,4)-oxadiazole, (1,3,4)-oxadiazole, (1,2,4)-thiadiazole, (1,3,4)-thiadiazole, benzothiazole, pyrrole, furan, thiophene, oxazole, thiazole, imidazole, pyrazole, isoxazole, 1,2,4-triazole, tetrazole, pyrimidine, pyrazine, pyridazine, oxazoline, thiazoline, tetrahydrofuran, tetrahydropyran, morpholine, piperidine, piperazine, pyrroline, pyrrolidine, oxazolidine, thiazolidine, oxirane or oxetane radical.

A preferred class of compounds of formula (I) are those in which:

$R^1$ is —C(=U)NR$^3$R$^4$ or —C(=V)OR$^{3a}$;

$R^{3a}$ is $(C_3-C_8)$cycloalkyl or $(C_3-C_8)$cycloalkyl-$(C_1-C_6)$alkyl, which cycloalkyl groups are unsubstituted or substituted by one or more $(C_1-C_6)$alkyl, $(C_1-C_6)$haloalkyl or $R^6$ groups; or is $(C_1-C_6)$alkyl, $(C_3-C_6)$alkenyl or $(C_3-C_6)$alkynyl which last three mentioned groups are substituted by one or more $R^{6a}$ groups; or is $(C_1-C_6)$alkylamino; or is NH(CHR$^{14}$)$_s$aryl which aryl group is unsubstituted or substituted by one or more $R^6$ groups;

$R^{6a}$ is $(C_1-C_6)$alkoxy, $(C_1-C_6)$haloalkoxy, $S(O)_n R^{14a}$, $CO_2(C_1-C_6)$alkyl, $CO_2H$, amino, $(C_0-C_6)$alkylamino, carbamoyl, $(C_1-C_6)$-alkylcarbamoyl, di-$(C_1-C_6)$-alkylcarbamoyl or CH[O$(C_1-C_6)$alkyl]$_2$; or is phenoxy unsubstituted or substituted by one or more $R^{14a}$ or halogen groups;

and the other values are as defined in formula (I).

A further preferred class of compounds of formula (I) are those in which:

$R^1$ is —C(=U) NR$^3$R$^4$;

$R^2$ is H;

$R^3$ is $R^5$ or OH; or is $(C_1-C_6)$alkyl substituted by one or more $R^6$ groups;

or $R^2$ and $R^3$ together with the interconnecting atoms may form a heterocyclic ring selected from (A) and (C):

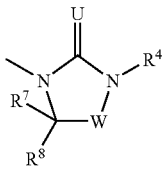

(A)

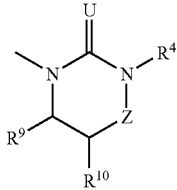

(C)

$R^4$ is H or $R^5$, or is $(C_1-C_6)$alkyl unsubstituted or substituted by one or more $R^6$ groups;

or $R^3$ and $R^4$ together with the adjacent N atom may form a pyrrolidin-1-yl, piperidin-1-yl, morpholin-1-yl or thiomorpholin-1-yl (or its S-oxide or S,S-dioxide) ring;

$R^5$ is $(C_3-C_6)$alkenyl, $(C_3-C_6)$alkynyl, $(C_3-C_8)$cycloalkyl, $(C_3-C_8)$cycloalkyl-$(C_1-C_6)$alkyl, $(C_1-C_6)$alkoxy, $(C_3-C_6)$alkenyloxy, $(C_3-C_6)$alkynyloxy or O(CR$^{15}$R$^{16}$)$_p$(C$_3$-C$_8$)cycloalkyl;

or —(CR$^{15}$R$^{16}$)$_p$phenyl, —(CR$^{15}$R$^{16}$)$_p$heterocyclyl, O(CR$^{15}$R$^{16}$)$_p$phenyl or O(CR$^{15}$R$^{16}$)$_p$heterocyclyl, which last four mentioned phenyl or heterocyclyl groups are unsubstituted or substituted by one or more $R^{17}$ groups;

$R^6$ is halogen, $(C_1-C_6)$alkoxy, $(C_1-C_6)$haloalkoxy, $S(O)_n R^{14a}$, CN, NO$_2$ or OH;

$R^{17}$ is $R^6$, $R^{14a}$ or CH$_2$OH;

U is S or O;

W is (CHR$^{19}$)$_q$ or CO;

Z is O;

$R^7$, $R^8$, $R^9$, $R^{10}$ and $R^{19}$ are each H; or $(C_1-C_6)$alkyl unsubstituted or substituted by one or more $R^6$ groups;

or $R^7$ and $R^8$ together with the attached carbon atom represent C=O;

$R^{14}$, $R^{15}$ and $R^{16}$ are each H or $(C_1-C_6)$alkyl;

$R^{14a}$ is $(C_1-C_6)$alkyl or $(C_1-C_6)$haloalkyl;

m is zero;

n, r, s, t and u are zero, one or two;

q is one; and wherein heterocyclyl denotes a pyridine, pyrimidine, (1,2,4)-oxadiazole, (1,3,4)-oxadiazole, (1,2,4)-thiadiazole, (1,3,4)-thiadiazole, pyrrole, furan, thiophene, oxazole, thiazole, benzothiazole, imidazole, pyrazole, isoxazole, 1,2,4-triazole, tetrazole, pyrazine, pyridazine, oxazoline, thiazoline, tetrahydrofuran, tetrahydropyran, morpholine, piperidine, piperazine, pyrroline, pyrrolidine, oxazolidine, thiazolidine, oxirane or oxetane radical.

A further preferred class of compounds of formula (I) are those in which:

$R^1$ is —C(=U)NR$^3$R$^4$;

$R^2$ is H;

U is O or S;

$R^3$ is $(C_1-C_6)$haloalkyl, $(C_3-C_6)$alkenyl, $(C_3-C_6)$alkynyl, $(C_3-C_8)$cycloalkyl, $(C_3-C_8)$cycloalkyl$(C_1-C_6)$alkyl, $(C_3-C_6)$alkenyloxy, $(C_3-C_6)$alkynyloxy, NH$_2$, $(C_1-C_6)$alkylamino, OH, Ophenyl, pyrimidyl, benzothiazolyl, thiazolyl, thiadiazolyl, —(CH$_2$)$_2$pyrrolidin-1-yl, NHSO$_2$phenyl, NHCO$(C_1-C_6)$alkyl, NHSO$_2(C_1-C_6)$alkyl, NHCOphenyl or N=C(phenyl)$_2$; or is pyridyl unsubstituted or substituted by one or more groups selected from halogen, $(C_1-C_6)$alkyl, $(C_1-C_6)$alkoxy, CN and NO$_2$; or is OCH$_2$phenyl which phenyl is unsubstituted or substituted by one or more groups selected from halogen, $(C_1-C_6)$alkyl, CN and NO$_2$; or is $(C_1-C_6)$alkoxy unsubstituted or substituted by a CO$_2(C_1-C_6)$alkyl group;

or is —(CHR$^{15}$)$_p$phenyl wherein p is 0, 1 or 2, $R^{15}$ is H or $(C_1-C_6)$alkyl, and phenyl is unsubstituted or substituted by one or more groups selected from halogen, $(C_1-C_6)$alkyl, $(C_1-C_6)$haloalkyl, $(C_1-C_6)$alkoxy, $(C_1-C_6)$haloalkoxy, CN, NO$_2$, OH, CH$_2$OH, CO$_2(C_1-C_6)$alkyl and phenoxy which phenoxy is unsubstituted or substituted by one or more groups selected from halogen and $(C_1-C_6)$haloalkyl;

or is $(C_1-C_6)$alkyl unsubstituted or substituted by one or more groups selected from $(C_1-C_6)$alkoxy, CN, OH, CO$_2(C_1-C_6)$alkyl and CH[O$(C_1-C_6)$alkyl]$_2$;

or is NH(CH$_2$)$_s$phenyl wherein s is zero or 1;

$R^4$ is H, $(C_1-C_6)$alkyl, $(C_3-C_6)$alkenyl, $(C_3-C_6)$alkynyl, $(C_3-C_8)$cycloalkyl, —(CH$_2$)$_p$phenyl wherein p is 0 or 1, or N=C[$(C_1-C_6)$alkyl]$_2$;

or $R^3$ and $R^4$ together with the adjacent N atom may form a pyrrolidin-1-yl, piperidin-1-yl, morpholin-1-yl, thiomorpholin-1-yl which groups are unsubstituted or substituted by one or more groups selected from halogen, $(C_1-C_6)$alkyl and OH; or form a 4,5-dihydropyrazol-1-yl ring; and m is zero.

A further preferred class of compounds of formula (I) are those in which:

$R^1$ is —C(=U)NR$^3$R$^4$;

U is O;

$R^2$ is $(C_1-C_6)$alkyl, $(C_3-C_6)$alkenyl, $(C_3-C_6)$alkynyl or CH$_2$phenyl; or is $(C_1-C_6)$alkyl substituted by CO$_2(C_1-C_6)$alkyl or CH[O$(C_1-C_6)$alkyl]$_2$;

$R^3$ is $(C_3-C_6)$alkenyloxy, $(C_3-C_6)$alkynyloxy, $CH_2$phenyl or $OCH_2$phenyl; or is $(C_1-C_6)$alkoxy unsubstituted or substituted by one or two $CO_2(C_1-C_6)$alkyl groups;

$R^4$ is H or $(C_1-C_6)$alkyl; and m is zero.

A further preferred class of compounds of formula (I) are those in which:

$R^1$ is —C(=U)NR$^3$R$^4$;

$R^2$ and $R^3$ together with the interconnecting atoms form a heterocyclic ring selected from (A) and (C):

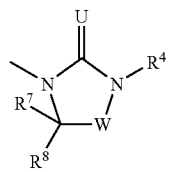
(A)

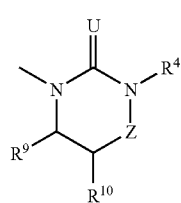
(C)

wherein U is O or S;

and in (A):

W is $CH_2$, CO or CHR$^{19}$ wherein $R^{19}$ is H, $(C_1-C_6)$alkyl or phenyl;

$R^4$ is H, $(C_1-C_6)$alkyl, phenyl, $CH_2$phenyl or $OCH_2$phenyl;

$R^7$ is H, $(C_1-C_6)$alkyl, $(C_1-C_6)$alkoxy or phenyl; and $R^8$ is H or $(C_1-C_6)$alkyl;

and in (C):

Z is O;

$R^4$ is $(C_1-C_6)$alkyl, $(C_3-C_8)$cycloalkyl or $CH_2$phenyl; and $R^9$ and $R^{10}$ are each H; and m is zero.

A further preferred class of compounds of formula (I) are those in which:

$R^1$ is —C(=U)NR$^3$R$^4$;

wherein U is NR$^{18}$;

$R^2$ is H;

$R^3$ is $(C_1-C_6)$alkyl, $(C_3-C_6)$alkenyl, $(C_3-C_8)$cycloalkyl; or is $(C_1-C_6)$alkyl substituted by one or two $(C_1-C_6)$alkoxy or $CH[O(C_1-C_6)alkyl]_2$ groups;

$R^4$ and $R^{18}$ are each the same or different H or $(C_1-C_6)$alkyl; or $R^3$ and $R^4$ together with the adjacent N atom form a morpholin-1-yl or pyrazol-1-yl ring; and m is zero.

A further preferred class of compounds of formula (I) are those in which:

$R^1$ is —C(=V)OR$^{3a}$;

wherein V is O or S;

$R^2$ is H, $(C_3-C_8)$cycloalkyl-$(C_1-C_6)$alkyl, $NHCH_2$phenyl; or is $(C_1-C_6)$alkyl substituted by a group selected from $(C_1-C_6)$alkoxy, CN, OH and $S(O)_nR^{14a}$;

$R^{3a}$ is $(C_3-C_8)$cycloalkyl or $(C_3-C_8)$cycloalkyl-$(C_1-C_6)$alkyl, which cycloalkyl groups are unsubstituted or substituted by one or more $R^6$ groups; or is $(C_1-C_6)$alkyl, $(C_3-C_6)$alkenyl or $(C_3-C_6)$alkynyl which last three mentioned groups are substituted by one or more $R^6$ groups; or is $(C_1-C_6)$alkylamino; or is NH(CHR$^{14}$)$_s$aryl which aryl group is unsubstituted or substituted by one or more $R^6$ groups; and m is zero.

A more preferred class of compounds of formula (I) are those in which:

$R^1$ is —C(=U)NR$^3$R$^4$;

$R^2$ is H;

U is O or S;

$R^3$ is $(C_1-C_6)$alkoxy, $C_1-C_6$)haloalkoxy, $(C_3-C_6)$alkenyloxy, $(C_3-C_6)$alkynyloxy, $CH_2$phenyl or $OCH_2$phenyl, phenyl or 2-pyridyl which last four mentioned phenyl or pyridyl groups are unsubstituted or substituted by one or more groups selected from halogen, $(C_1-C_6)$alkyl, $(C_1-C_6)$alkoxy, CN and NO2;

$R^4$ is H, $(C_1-C_6)$alkyl, $(C_3-C_6)$alkenyl, $(C_3-C_6)$alkynyl or $CH_2$phenyl; and m is zero.

A further more preferred class of compounds of formula (I) are those in which:

$R^1$ is —C(=U)NR$^3$R$^4$;

$R^2$ is H;

U is O;

$R^3$ is $(C_1-C_6)$alkoxy;

$R^4$ is $(C_1-C_6)$alkyl; and m is zero.

The compounds of general formula (I) can be prepared by the application or adaptation of known methods (i.e. methods heretofore used or described in the chemical literature.

In the following description of processes when symbols appearing in formulae are not specifically defined, it is understood that they are "as defined above" in accordance with the first definition of each symbol in the specification.

According to a feature of the invention compounds of formula (I) wherein $R^1$ is —C(=U)NR$^3$R$^4$, m is zero, and $R^2$, U, $R^3$ and $R^4$ are as defined above; or $R^2$ and $R^3$ together with the interconnecting atoms form a heterocyclic ring selected from (A), (B), (C), (D) and (E);

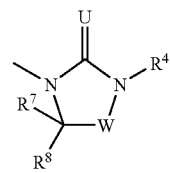
(A)

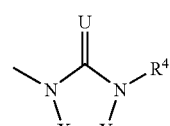
(B)

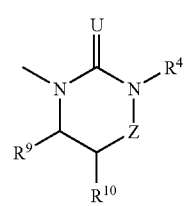
(C)

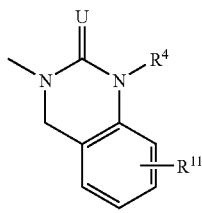
(D)

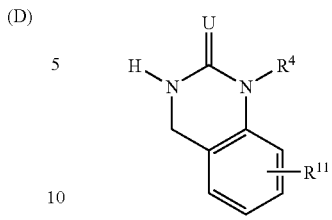
(VII)

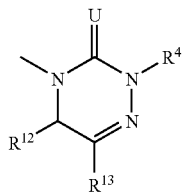
(E)

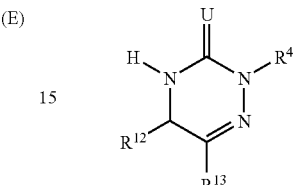
(VIII)

wherein $R^4$, $R^7$, $R^8$, $R^9$, $R^{10}$, $R^{11}$, $R^{12}$, $R^{13}$, W, X, Y and Z are as defined above, may be prepared by the reaction of a compound of formula (II):

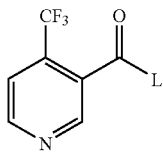
(II)

wherein L is a leaving group, generally halogen and preferably chlorine, with a compound of formula (III):

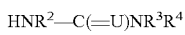
(III)

wherein $R^2$, U, $R^3$ and $R^4$ are as defined above, or with a compound of formula (IV), (V), (VI); (VII) or (VIII):

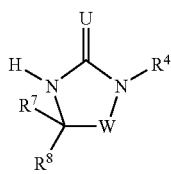
(IV)

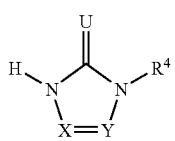
(V)

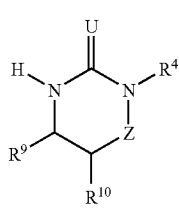
(VI)

wherein $R^4$, $R^7$, $R^8$, $R^9$, $R^{10}$, $R^{11}$, $R^{12}$, $R^{13}$, W, X, Y and Z are as defined above. The reaction is generally performed in the presence of an organic base such as a tertiary amine for example triethylamine, or pyridine, or an inorganic base such as an alkali metal carbonate, for example potassium carbonate, or an alkali metal alkoxide such as sodium ethoxide, or sodium hydride, in a solvent such as dioxan, tetrahydrofuran or N,N-dimethylformamide, at a temperature of from 0° to 100° C. (preferably 0° to 50° C.).

According to a further feature of the present invention compounds of formula (I) wherein $R^1$ is —C(=U)NR$^3$R$^4$, m is zero, $R^2$ is H, U is O, and $R^3$ and $R^4$ are as defined above, may be prepared by the reaction of a compound of formula (IX):

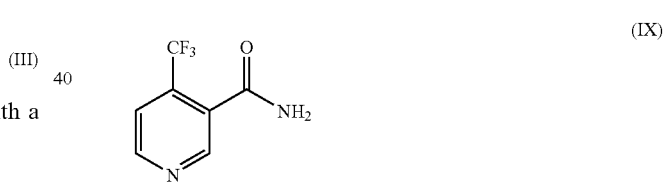
(IX)

with oxalyl chloride or triphosgene, in an inert solvent such as dichloroethane at a temperature of from 0° C. to the reflux temperature of the solvent, followed by removal of the solvent to give the corresponding acylisocyanate intermediate which is generally not isolated, and which is directly reacted with an amine of formula (X):

HNR$^3$R$^4$ (X)

wherein $R^3$ and $R^4$ are as defined above. The reaction is generally performed in an inert solvent such as dichloroethane or tetrahydrofuran at a temperature of from 0° to 60° C.

According to a further feature of the present invention compounds of formula (I) wherein $R^1$ is —C(=V)OR$^{3a}$, m is zero, $R^2$ is H, V is O, and $R^{3a}$ is as defined above, may be prepared by the reaction of a compound of formula (IX) as defined above, with oxalyl chloride to give an acylisocyanate intermediate above which is generally not isolated, and which is directly reacted with an alcohol of formula (XI):

HOR$^{3a}$ (XI)

wherein $R^3$ is as defined above. The reaction is generally performed in an inert solvent such as dichloroethane or tetrahydrofuran at a temperature of from 0° to 60° C.

According to a further feature of the present invention compounds of formula (I) wherein $R^1$ is —C(=U)NR$^3$R$^4$, m is zero, $R^2$ is H, U is O or S, and $R^3$ and $R^4$ are as defined above, may be prepared by the reaction of a compound of formula (XII).

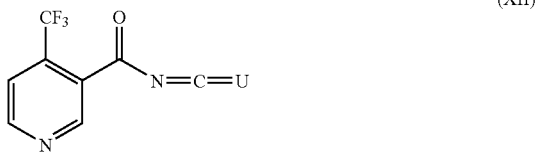

(XII)

wherein U is O or S, with a compound of formula (X) as defined above. The reaction is generally performed in an inert solvent such as dichloroethane or tetrahydrofuran at a temperature of from 0° to 60° C.

According to a further feature of the present invention compounds of formula (I) wherein $R^1$ is —C(=V)OR$^{3a}$, m is zero, $R^2$ is H, V is O or S, and $R^{3a}$ is as defined above, may be prepared by the reaction of a compound of formula (XIII).

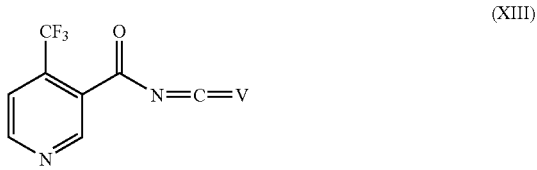

(XIII)

wherein V is O or S, with a compound of formula (XI) as defined above. The reaction is generally performed in an inert solvent such as dichloroethane or tetrahydrofuran at a temperature of from 0° to 60° C.

According to a further feature of the present invention compounds of formula (i) wherein $R^1$ is —C(=U)NR$^3$R$^4$, m is zero, $R^2$ is H, $R^4$ is H, U is O or S, and $R^3$ is as defined above, may be prepared by the reaction of a compound of formula (IX) as defined above, with a strong base such as sodium hydride to form the corresponding salt, which is then reacted with a compound of formula (XIV):

$$R^3N=C=U \qquad (XIV)$$

wherein $R^3$ is as defined above. The reaction is generally performed in an inert solvent such as N,N-dimethylformamide at a temperature of from 0° to 60° C.

According to a further feature of the present invention compounds of formula (I) wherein $R^1$ is —C(=U)NR$^3$R$^4$ or —C(=V)OR$^{3a}$, m is zero, $R^2$ is H, U and V are each S, and $R^3$, $R^{3a}$ and $R^4$ are as defined above, may be prepared in a 1-pot process by the reaction of 4-trifluoromethylnicotinic acid with a suitable halogenating agent, preferably oxalyl chloride, in a solvent such as dichloroethane, optionally in the presence of N,N-dimethylformamide, at a temperature of from 0° C. to the reflux temperature of the solvent, to give the corresponding acid chloride, followed by removal of the solvent, and reaction with an alkali metal thiocyanate or ammonium thiocyanate or a tetraalkylammonium thiocyanate for example tetrabutylammonium thiocyanate, generally in the presence of a base, such as an alkali metal carbonate for example potassium carbonate, in an inert solvent such as toluene or acetone, at a temperature of from 0° to 60° C., to give 4-trifluoromethyl-3-pyridylcarbonyl isothiocyanate, followed by reaction with an amine of formula (X) above or an alcohol of formula (XI) above, at a temperature of from 0° to 60° C.

According to a further feature of the invention compounds of formula (I) wherein $R^1$ is —C(=U)NR$^3$R$^4$, m is zero, U, $R^3$ and $R^4$ are as defined above, and $R^2$ is ($C_1$-$C_6$)alkyl, ($C_3$-$C_6$)alkenyl, ($C_3$-$C_6$)alkynyl, ($C_3$-$C_8$)cycloalkyl or ($C_3$-$C_8$)cycloalkyl-($C_1$-$C_6$)alkyl which groups are unsubstituted or substituted by one or more $R^6$ groups; or is —(CR$^{15}$R$^{16}$)$_p$aryl or —(CR$^{15}$R$^{16}$)$_p$heterocyclyl, which aryl or heterocyclyl groups are optionally substituted by $R^{17}$; wherein $R^6$, $R^{15}$, $R^{16}$ and $R^{17}$ are as defined above, may be prepared by the reaction of the corresponding compound of formula (I) wherein $R^2$ is H, using an alkylatig agent of formula (XV):

$$R^2\text{-}L^1 \qquad (XV)$$

wherein $L^1$ is a leaving group generally halogen and preferably chlorine. The reaction is generally performed in the presence of an organic base such as a tertiary amine for example triethylamine, or pyridine, or an inorganic base such as an alkali metal carbonate, for example potassium carbonate, or an alkali metal alkoxide such as sodium ethoxide, or sodium hydride, in a solvent such as dioxan, tetrahydrofuran or N,N-dimethylformamide, at a temperature of from 0° to 100° C. (preferably 0° to 50° C.).

According to a further feature of the invention compounds of formula (I) wherein $R^1$, and $R^2$ are as defined above, and m is 1 may be prepared by oxidising a corresponding compound in which m is 0. The oxidation is generally performed using hydrogen peroxide in a solvent such as acetic acid, or a peracid such as 3-chloroperbenzoic acid in a solvent such as dichloromethane or 1,2-dichloroethane, at a temperature of from 0° C. to the reflux temperature of the solvent.

Intermediates of formula (II) wherein L is chlorine, may be prepared according to known procedures, for example by the reaction of the corresponding carboxylic acid of formula (II) wherein L is replaced by OH, with a suitable halogenating agent, preferably oxalyl chloride or thionyl chloride, in a solvent such as dichloroethane, optionally in the presence of N,N-dimethylformamide, at a temperature of from 0° C. to the reflux temperature of the solvent.

Intermediates of formula (XII) wherein U is S, and (XIII) wherein V is O, may be prepared according to known procedures, for example by the reaction of a compound of formula (II) as defined above, with an alkali metal thiocyanate or ammonium thiocyanate or a tetraalkylammonium thiocyanate for example tetrabutylammonium thiocyanate, generally in the presence of a base such as an alkali metal carbonate for example potassium carbonate, in an inert solvent solvent such as toluene or acetone, at a temperature of from 0° to 100° C.

Intermediate of formula (XII) wherein U is O, may be prepared according to known procedures, for example by the reaction of a compound of formula (II) as defined above, with an alkali metal cyanate or ammonium cyanate or a tetraalkylammonium cyanate for example tetrabutylammonium cyanate, generally in the presence of a base such as an alkali metal carbonate for example potassium carbonate, in an inert solvent solvent such as toluene, at a temperature of from 0° to 100° C.

Collections of compounds of the formula (I) which can be synthesized by the above mentioned process may also be prepared in a parallel manner, and this may be effected manually or in a semiautomated or fully automated manner. In this case, it is possible, for example, to automate the procedure of the reaction, work-up or purification of the products or of the intermediates. In total, this is to be understood as meaning a procedure as is described, for example, by S. H. DeWitt in "Annual Reports in Combinatorial Chemistry and Molecular Diversity: Automated Synthesis", Volume 1, Verlag Escom 1997, pages 69 to 77.

A series of commercially available apparatuses as are offered by, for example, Stem Corporation, Woodrolfe Road, Tollesbury, Essex, CM9 8SE, England or H+P Labortechnik GmbH, Bruckmannring 28, 85764 Oberschleißheim, Germany or Radleys, Shirehill, Saffron Walden, Essex, England, may be used for the parallel procedure of the reaction and work-up. For the parallel purification of compounds of the formula (I), or of intermediates obtained during the preparation, use may be made, inter alia, of chromatography apparatuses, for example those by ISCO, Inc., 4700 Superior Street, Lincoln, Nebr. 68504, USA.

The apparatuses mentioned lead to a modular procedure in which the individual process steps are automated, but manual operations must be performed between the process steps. This can be prevented by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to what has been described here, compounds of the formula (I) may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131-5135), in which products by IRORI, 11149 North Torrey Pines Road, La Jolla, Calif. 92037, USA, are employed, may be semiautomated. The automation of solid-phase-supported parallel syntheses is performed successfully, for example, by apparatuses by Argonaut Technologies, Inc., 887 Industrial Road, San Carlos, Calif. 94070, USA or MultiSynTech GmbH, Wullener Feld 4, 58454 Witten, Germany.

The preparation of the processes described herein yields compounds of the formula (I) in the form of substance collections which are termed libraries. The present invention also relates to libraries which comprise at least two compounds of the formula (I).

Compounds of formula (II), (III), (IV), (V), (VI), (VII), (VIII), (IX), (X), (XI), (XIV) and (XV) are known or may be prepared by known methods.

The following non-limiting Examples illustrate the preparation of the compounds of formula (I).

CHEMICAL EXAMPLES

NMR spectra were run in deuterochloroform unless stated otherwise. In the Examples which follow, quantities (also percentages) are weight-based, unless stated otherwise.

Example 1

Oxalyl chloride (0.15 ml) was added to a suspension of 4-trifluoromethyl-3-pyridinecarboxamide (0.25 g) in 1,2-dichloroethane at 20° C. and then heated to reflux for 2 hours. The mixture was cooled, evaporated and the residue containing 4-trifluoromethyl-3-pyridylcarbonyl isocyanate was dissolved in tetrahydrofuran. Benzylamine (0.15 ml) was added and the mixture stirred at 20° C. for 2 hours and evaporated. The residue was purified by silica-gel column chromatography, eluting with n-hexane/ethyl acetate (3:2), to give 1-benzyl-3-(4-trifluoromethyl-3-pyridylcarbonyl)urea (0.30 g, Compound A-37).

By proceeding in a similar manner there was prepared 1-benzyl-1-(2-hydroxyethyl)-3-(4-trifluoromethyl-3-pyridylcarbonyl)urea (Compound A-862).

Example 2

Oxalyl chloride (1.50 ml) was added to a suspension of 4-trifluoromethyl-3-pyridinecarboxamide (2.0 g) in 1,2-dichloroethane at 20° C., and stirred under reflux for 2 hours. The mixture was evaporated and dichloromethane added to the residue containing 4-trifluoromethyl-3-pyridylcarbonyl isocyanate. To this was added at 20° C. a suspension of N,O-dimethylhydroxylamine hydrochloride (2.05 g) and triethylamine (3.0 ml) in dichloromethane, which had been prepared in advance. The mixture was stirred for 30 minutes, then water added and the organic layer dried (magnesium sulfate) and evaporated, to give after trituration with ethanol, 1-methyl-1-methoxy-3-(4-trifluoromethyl-3-pyridylcarbonyl)urea (2.2 g) (Compound A-313).

By proceeding in a similar manner there was prepared 1-hydroxyl-1-isopropyl-3-(4-trifluoromethyl-3-pyridylcarbonyl)urea (Compound A-540).

Example 3

Sodium hydride (0.090 g, 60% dispersion in mineral oil) was added to a solution of 4-trifluoromethyl-3-pyridinecarboxamide (0.40 g) in N,N-dimethylformamide at 20° C., and stirred for 1 hour. Benzyl isocyanate (0.31 ml) was added and the mixture stirred at 20° C. for 2 hours, then methyl bromoacetate (0.30 ml) added and stirring continued for 5 hours. Ethyl acetate and water were added to the solution and the organic phase dried (magnesium sulfate), evaporated and the residue purified by column chromatography on silica gel, eluting with n-hexane/ethyl acetate (2:1), to give 3-benzyl-1-(4-trifluoromethyl-3-pyridylcarbonyl)hydantoin (0.50 g, Compound S-132).

Example 4

Methanesulfonyl chloride (0.17 ml) was added to an ice-cooled mixture of 1-benzyl-1-(2-hydroxyethyl)-3-(4-trifluoromethyl-3-pyridylcarbonyl)urea (0.70 g), and triethylamine (0.64 ml) in dichloromethane, then stirred for 3 hours at 20° C. The mixture was washed (water), dried (magnesium sulfate), evaporated and the residue purified by silica-gel chromatography, eluting with n-hexane/ethyl acetate (3:2), to give 1-benzyl-3-(4-trifluoromethyl-3-pyridylcarbonyl)-2-imidazolidinone (0.63 g, Compound S-15).

Example 5

1,2-Dibromoethane (0.06 ml) was added to a suspension of 1-hydroxyl-1-isopropyl-3-(4-trifluoromethyl-3-pyridylcarbonyl)urea (0.20 g) and potassium carbonate (0.20 g) in N,N-dimethylformamide at 20° C., and stirred for 3 hours. Ethyl acetate and water were added and the organic phase dried (magnesium sulfate), evaporated and the residue purified by column chromatography on silica gel, eluting with n-hexane/ ethyl acetate (2:1), to give 2-isopropyl-4-(4-trifluoromethyl-3-pyridylcarbonyl)-perhydro-1,2,4-oxadiazin-3-one (0.25 g, Compound U-3).

Example 6

Oxalyl chloride (3.2 ml, 2M) was added to a suspension of 4-trifluoromethylnicotinic acid (1 g) and a catalytic amount of N,N-dimethylformamide in dichloromethane, and stirred at 20° C. for 1 hour. After evaporation, the residue was dissolved in acetone and potassium thiocyanate (1 g) added with ice bath cooling to give 4-trifluoromethyl-3-pyridylcarbonyl isothiocyanate, then N-methylaniline (0.65 g) was added and the mixture stirred at 20° C. for 1 hour. Ethyl acetate was added and the mixture washed with water, dried (magnesium sulfate), evaporated and the residue purified by silica-gel chromatography, eluting with n-hexane/ethyl acetate=2/1, to give 1-methyl-1-phenyl-3-(4-trifluoromethyl-3-pyridylcarbonyl)thiourea (0.96 g, Compound B-349).

Example 7

Oxalyl chloride (6.4 ml, 2M) was added to a suspension of 4-trifluoromethylnicotinic acid (2 g) and a catalytic amount of N,N-dimethylformamide in dichloromethane, and stirred at 20° C. for 1 hour to give a solution of 4-trifluoromethylnicotinic acid chloride. N,N-Ethylenethiourea (2.23 g) was added to sodium hydride (0.82 g, 60% dispersion in mineral oil) in tetrahydrofuran, and the mixture was stirred at 20° C. for 1 hour, and then added to the above solution of 4-trifluoromethylnicotinic acid chloride with ice bath cooling, then stirred at 20° C. for 1 hour. Ethyl acetate was added and the mixture washed with water, dried (magnesium sulfate), evaporated and the residue crystallized (ethanol) to give N-(4-trifluoromethyl-3-pyridylcarbonyl)-imidazolin-2-thione (1.35 g, Compound S-356).

Example 8

Oxalyl chloride (9.6 ml, 2M) was added to a suspension 4-trifluoromethylnicotinic acid (3 g) and a catalytic amount of N,N-dimethylformamide in dichloromethane, and stirred at 20° C. for 1 hour. The mixture was evaporated, the residue dissolved in toluene and tetrabutylammonium thiocyanate (3 g) and potassium carbonate (1.5 g) added, then stirred at 20° C. for 30 minutes to give 4-trifluoromethyl-3-pyridylcarbonyl isothiocyanate 2,2,2-trifluoroethanol (3.15 g) was then added, and the mixture stirred at 20° C. for 1 hour. Ethyl acetate was added and the mixture washed with water, hydrochloric acid 1(M), saturated sodium bicarbonate and brine, dried (magnesium sulfate), evaporated and recrystallised from ethanol to give 2,2,2-trifluoroethyl N-(4-trifluoromethyl-3-pyridylcarbonyl)thiocarbamate (1.2 g, Compound X-45).

Example 9

Allyl bromide (0.10 ml) was added to a suspension of 1-methyl-1-methoxy-3-(4-trifluoromethyl-3-pyridylcarbonyl)urea (0.25 g) and potassium carbonate (0.16 g) in N,N-dimethylformamide at 20° C., and stirred for 2 hours. Ethyl acetate and water were added and the organic phase dried (magnesium sulfate), evaporated and the residue purified by column chromatography on silica gel, eluting with n-hexane/ethyl acetate (2:1) to give 1-methyl-1-methoxy-3-allyl-3-(4-trifluoromethyl-3-pyridylcarbonyl)urea (0.26 g, Compound E-85).

The following preferred compounds shown in Tables 1 to 9 also form part of the present invention, and were or may be prepared in accordance with, or analogously to, the above-mentioned Examples 1 to 9 or the above-described general methods. In the Tables Ph means phenyl. Where subscripts are omitted after atoms it will be understood that they are intended, for example CH3 means $CH_3$.

Compound numbers are given for reference purposes only.

TABLE I

Compounds of formula (I) in which $R^1$ is $-C(=U)NR^3R^4$; $R^2$ is H and m is zero. In Table 1 compounds A-1 to A-881 represent individual compounds in which U is O, whilst compounds B-1 to B-881 represent individual compounds in which U is S.

| Compound | | $R^3$ | $R^4$ |
|---|---|---|---|
| A-1 | B-1 | $CH_3CH=CH$ | H |
| A-2 | B-2 | $CH_2=CHCH_2$ | H |
| A-3 | B-3 | $CH_3(CH_3)C=CH$ | H |
| A-4 | B-4 | $(CH_3)_2C=CH$ | H |
| A-5 | B-5 | $CH_3CH=CHCH_2$ | H |
| A-6 | B-6 | $CH_2=C(CH_3)CH_2$ | H |
| A-7 | B-7 | $CH_3CH=C(Cl)CH_2$ | H |
| A-8 | B-8 | $CH_2=CHCH_2CH_2$ | H |
| A-9 | B-9 | $CH_3CH_2(CH_3)C=CH$ | H |
| A-10 | B-10 | $(CH_3)_2CHCH=CH$ | H |
| A-11 | B-11 | $CH_3CH_2CH=CHCH_2$ | H |
| A-12 | B-12 | $CH_3CH=C(CH_3)CH_2$ | H |
| A-13 | B-13 | $CH(CH_3)HC=CHCH_3$ | H |
| A-14 | B-14 | $CH_2HC=C(CH_3)_2$ | H |
| A-15 | B-15 | $CH_3CH=CHCH_2CH_2$ | H |
| A-16 | B-16 | $CH_2=CH_2CH_2CH_2CH_2$ | H |
| A-17 | B-17 | $CH_2=CH_2CH_2CH_2CHCH_2$ | H |
| A-18 | B-18 | $CHCCH_2$ | H |
| A-19 | B-19 | $CH_3CCCH_2$ | H |
| A-20 | B-20 | $CHCCH(CH_3)$ | H |
| A-21 | B-21 | $CH_3CCCH(CH_3)$ | H |
| A-22 | B-22 | $CHCC(CH_3)_2$ | H |
| A-23 | B-23 | $CH_3CCC(CH_3)_2$ | H |
| A-24 | B-24 | cyclo-$C_3H_5$ | H |
| A-25 | B-25 | cyclo-$C_3H_4(_1-CH_3)$ | H |
| A-26 | B-26 | cyclo-$C_4H_7$ | H |
| A-27 | B-27 | cyclo-$C_4H_6(_1-CH_3)$ | H |
| A-28 | B-28 | cyclo-$C_5H_9$ | H |
| A-29 | B-29 | cyclo-$C_5H_8(_1-CH_3)$ | H |
| A-30 | B-30 | cyclo-$C_6H_{11}$ | H |
| A-31 | B-31 | cyclo-$C_6H_{10}(_1-CH_3)$ | H |
| A-32 | B-32 | (cyclo-$C_3H_5)CH_2$ | H |
| A-33 | B-33 | (cyclo-$C_3H_4(_1-CH_3))CH_2$ | H |
| A-34 | B-34 | (cyclo-$C_4H_7)CH_2$ | H |
| A-35 | B-35 | (cyclo-$C_5H_9)CH_2$ | H |
| A-36 | B-36 | (cyclo-$C_6H_{11})CH_2$ | H |
| A-37 | B-37 | $PhCH_2$ | H |
| A-38 | B-38 | $PhCH(CH_3)$ | H |
| A-39 | B-39 | $PhCH_2CH_2$ | H |
| A-40 | B-40 | $PhC(CH_3)_2$ | H |
| A-41 | B-41 | $PhCH_2CH_2$ | H |
| A-42 | B-42 | (2-F—Ph)$CH_2$ | H |
| A-43 | B-43 | (3-F—Ph)$CH_2$ | H |
| A-44 | B-44 | (4-F—Ph)$CH_2$ | H |
| A-45 | B-45 | (2-Cl—Ph)$CH_2$ | H |
| A-46 | B-46 | (3-Cl—Ph)$CH_2$ | H |
| A-47 | B-47 | (4-Cl—Ph)$CH_2$ | H |
| A-48 | B-48 | (2-Br—Ph)$CH_2$ | H |
| A-49 | B-49 | (3-Br—Ph)$CH_2$ | H |
| A-50 | B-50 | (4-Br—Ph)$CH_2$ | H |
| A-51 | B-51 | (2-I—Ph)$CH_2$ | H |
| A-52 | B-52 | (3-I—Ph)$CH_2$ | H |
| A-53 | B-53 | (4-I—Ph)$CH_2$ | H |
| A-54 | B-54 | (2-$CF_3$—Ph)$CH_2$ | H |
| A-55 | B-55 | (3-$CF_3$—Ph)$CH_2$ | H |
| A-56 | B-56 | (4-$CF_3$—Ph)$CH_2$ | H |
| A-57 | B-57 | (2-$CH_3$—Ph)$CH_2$ | H |
| A-58 | B-58 | (3-$CH_3$—Ph)$CH_2$ | H |
| A-59 | B-59 | (4-$CH_3$—Ph)$CH_2$ | H |
| A-60 | B-60 | (2-$CH_3O$—Ph)$CH_2$ | H |
| A-61 | B-61 | (3-$CH_3O$—Ph)$CH_2$ | H |
| A-62 | B-62 | (4-$CH_3O$—Ph)$CH_2$ | H |

TABLE I-continued

Compounds of formula (I) in which $R^1$ is —C(=U)NR$^3$R$^4$; $R^2$ is H and m is zero. In Table 1 compounds A-1 to A-881 represent individual compounds in which U is O, whilst compounds B-1 to B-881 represent individual compounds in which U is S.

| Compound | | $R^3$ | $R^4$ |
|---|---|---|---|
| A-63 | B-63 | HO | H |
| A-64 | B-64 | CH$_3$O | H |
| A-65 | B-65 | CH$_3$CH$_2$O | H |
| A-66 | B-66 | n-C$_3$H$_7$O | H |
| A-67 | B-67 | iso-C$_3$H$_7$O | H |
| A-68 | B-68 | n-C$_4$H9O | H |
| A-69 | B-69 | sec-C$_4$H9O | H |
| A-70 | B-70 | iso-C$_4$H9O | H |
| A-71 | B-71 | tert-C$_4$H9O | H |
| A-72 | B-72 | n-C$_5$H$_{11}$O | H |
| A-73 | B-73 | n-C6H$_{13}$O | H |
| A-74 | B-74 | CH$_2$=CHCH$_2$O | H |
| A-75 | B-75 | CH$_2$=C(CH$_3$)CH$_2$O | H |
| A-76 | B-76 | CH$_2$=CHCH(CH$_3$)O | H |
| A-77 | B-77 | CH$_2$=C(Cl)CH$_2$O | H |
| A-78 | B-78 | CH$_2$=CHC(CH$_3$)$_2$O | H |
| A-79 | B-79 | CH$_3$CH=CHCH$_2$O | H |
| A-80 | B-80 | CH$_2$=CH$_2$CH$_2$CH$_2$O | H |
| A-81 | B-81 | CHCCH$_2$O | H |
| A-82 | B-82 | CH$_3$CCCH$_2$O | H |
| A-83 | B-83 | CHCCH(CH$_3$)O | H |
| A-84 | B-84 | CHCC(CH$_3$)$_2$O | H |
| A-85 | B-85 | CH$_3$CH$_2$O$_2$CCH$_2$O | H |
| A-86 | B-86 | PhCH$_2$O | H |
| A-87 | B-87 | 2-CH$_3$O—PhCH$_2$O | H |
| A-88 | B-88 | 3-CH$_3$O—PhCH$_2$O | H |
| A-89 | B-89 | 4-CH$_3$O—PhCH$_2$O | H |
| A-90 | B-90 | PhO | H |
| A-91 | B-91 | 2-Cl—PhO | H |
| A-92 | B-92 | 3-Cl—PhO | H |
| A-93 | B-93 | 4-Cl—PhO | H |
| A-94 | B-94 | 2-CF$_3$—PhO | H |
| A-95 | B-95 | 3-CF$_3$—PhO | H |
| A-96 | B-96 | 4-CF$_3$—PhO | H |
| A-97 | B-97 | 2-CH$_3$O—PhO | H |
| A-98 | B-98 | 3-CH$_3$O—PhO | H |
| A-99 | B-99 | 4-CH$_3$O—PhO | H |
| A-100 | B-100 | NH$_2$ | H |
| A-101 | B-101 | CH$_3$NH | H |
| A-102 | B-102 | C$_2$H$_5$NH | H |
| A-103 | B-103 | n-C$_3$H7NH | H |
| A-104 | B-104 | iso-C$_3$H7NH | H |
| A-105 | B-105 | n-C$_4$H9NH | H |
| A-106 | B-106 | n-C$_5$H$_{11}$NH | H |
| A-107 | B-107 | n-C6H$_{13}$NH | H |
| A-108 | B-108 | PhCH$_2$NH | H |
| A-109 | B-109 | PhNH | H |
| A-110 | B-110 | 2-F—PhNH | H |
| A-111 | B-111 | 3-F—PhNH | H |
| A-112 | B-112 | 4-F—PhNH | H |
| A-113 | B-113 | 2-Cl—PhNH | H |
| A-114 | B-114 | 3-Cl—PhNH | H |
| A-115 | B-115 | 4-Cl—PhNH | H |
| A-116 | B-116 | 2-Br—PhNH | H |
| A-117 | B-117 | 3-Br—PhNH | H |
| A-118 | B-118 | 4-Br—PhNH | H |
| A-119 | B-119 | 2-I—PhNH | H |
| A-120 | B-120 | 3-I—PhNH | H |
| A-121 | B-121 | 4-I—PhNH | H |
| A-122 | B-122 | 2-CF$_3$—PhNH | H |
| A-123 | B-123 | 3-CF$_3$—PhNH | H |
| A-124 | B-124 | 4-CF$_3$—PhNH | H |
| A-125 | B-125 | 2-CH$_3$—PhNH | H |
| A-126 | B-126 | 3-CH$_3$—PhNH | H |
| A-127 | B-127 | 4-CH$_3$—PhNH | H |
| A-128 | B-128 | 2-CH$_3$O—PhNH | H |
| A-129 | B-129 | 3-CH$_3$O—PhNH | H |
| A-130 | B-130 | 4-CH$_3$O—PhNH | H |
| A-131 | B-131 | 2-NO$_2$—PhNH | H |
| A-132 | B-132 | 3-NO$_2$—PhNH | H |
| A-133 | B-133 | 4-NO$_2$—PhNH | H |
| A-134 | B-134 | 2-CN—PhNH | H |
| A-135 | B-135 | 3-CN—PhNH | H |
| A-136 | B-136 | 4-CN—PhNH | H |
| A-137 | B-137 | Ph(Me)N | H |
| A-138 | B-138 | 2-F—Ph(Me)N | H |
| A-139 | B-139 | 3-F—Ph(Me)N | H |
| A-140 | B-140 | 4-F—Ph(Me)N | H |
| A-141 | B-141 | 2-Cl—Ph(Me)N | H |
| A-142 | B-142 | 3-Cl—Ph(Me)N | H |
| A-143 | B-143 | 4-Cl—Ph(Me)N | H |
| A-144 | B-144 | 3-CF$_3$—Ph(Me)N | H |
| A-145 | B-145 | 4-CF$_3$—Ph(Me)N | H |
| A-146 | B-146 | 2-CH$_3$O—Ph(Me)N | H |
| A-147 | B-147 | 3-CH$_3$O—Ph(Me)N | H |
| A-148 | B-148 | 4-CH$_3$O—Ph(Me)N | H |
| A-149 | B-149 | Ph | H |
| A-150 | B-150 | 2-F—Ph | H |
| A-151 | B-151 | 3-F—Ph | H |
| A-152 | B-152 | 4-F—Ph | H |
| A-153 | B-153 | 2-Cl—Ph | H |
| A-154 | B-154 | 3-Cl—Ph | H |
| A-155 | B-155 | 4-Cl—Ph | H |
| A-156 | B-156 | 2-Br—Ph | H |
| A-157 | B-157 | 3-Br—Ph | H |
| A-158 | B-158 | 4-Br—Ph | H |
| A-159 | B-159 | 2-I—Ph | H |
| A-160 | B-160 | 3-I—Ph | H |
| A-161 | B-161 | 4-I—Ph | H |
| A-162 | B-162 | 2-CF$_3$—Ph | H |
| A-163 | B-163 | 3-CF$_3$—Ph | H |
| A-164 | B-164 | 4-CF$_3$—Ph | H |
| A-165 | B-165 | 2-CH$_3$—Ph | H |
| A-166 | B-166 | 3-CH$_3$—Ph | H |
| A-167 | B-167 | 4-CH$_3$—Ph | H |
| A-168 | B-168 | 2-CH$_3$O—Ph | H |
| A-169 | B-169 | 3-CH$_3$O—Ph | H |
| A-170 | B-170 | 4-CH$_3$O—Ph | H |
| A-171 | B-171 | 2-NO$_2$—Ph | H |
| A-172 | B-172 | 3-NO$_2$—Ph | H |
| A-173 | B-173 | 4-NO$_2$—Ph | H |
| A-174 | B-174 | 2-CN—Ph | H |
| A-175 | B-175 | 3-CN—Ph | H |
| A-176 | B-176 | 4-CN—Ph | H |
| A-177 | B-177 | 2-CO$_2$H—Ph | H |
| A-178 | B-178 | 3-CO$_2$H—Ph | H |
| A-179 | B-179 | 4-CO$_2$H—Ph | H |
| A-180 | B-180 | 2-CO$_2$Me—Ph | H |
| A-181 | B-181 | 3-CO$_2$Me—Ph | H |
| A-182 | B-182 | 4-CO$_2$Me—Ph | H |
| A-183 | B-183 | 2-HO—Ph | H |
| A-184 | B-184 | 3-HO—Ph | H |
| A-185 | B-185 | 4-HO—Ph | H |
| A-186 | B-186 | 2-NH$_2$—Ph | H |
| A-187 | B-187 | 3-NH$_2$—Ph | H |
| A-188 | B-188 | 4-NH$_2$—Ph | H |
| A-189 | B-189 | 2-HOCH$_2$—Ph | H |
| A-190 | B-190 | 3-HOCH$_2$—Ph | H |
| A-191 | B-191 | 4-HOCH$_2$—Ph | H |
| A-192 | B-192 | 2-CF$_3$O—Ph | H |
| A-193 | B-193 | 3-CF$_3$O—Ph | H |
| A-194 | B-194 | 4-CF$_3$O—Ph | H |
| A-195 | B-195 | 2-CF$_3$CH$_2$O—Ph | H |
| A-196 | B-196 | 3-CF$_3$CH$_2$O—Ph | H |
| A-197 | B-197 | 4-CF$_3$CH$_2$O—Ph | H |
| A-198 | B-198 | 2-(4-Cl—PhO)—Ph | H |
| A-199 | B-199 | 3-(4-Cl—PhO)—Ph | H |
| A-200 | B-200 | 4-(4-Cl—PhO)—Ph | H |
| A-201 | B-201 | 2-(4-CF$_3$—PhO)—Ph | H |
| A-202 | B-202 | 3-(4-CF$_3$—PhO)—Ph | H |
| A-203 | B-203 | 4-(4-CF$_3$—PhO)—Ph | H |
| A-204 | B-204 | 2,3-diCl—Ph | H |
| A-205 | B-205 | 2,5-diCl—Ph | H |
| A-206 | B-206 | 2,6-diCl—Ph | H |

TABLE I-continued

Compounds of formula (I) in which $R^1$ is —C(=U)NR$^3$R$^4$; $R^2$ is H and m is zero. In Table 1 compounds A-1 to A-881 represent individual compounds in which U is O, whilst compounds B-1 to B-881 represent individual compounds in which U is S.

| Compound | | $R^3$ | $R^4$ |
|---|---|---|---|
| A-207 | B-207 | 3,4-diCl—Ph | H |
| A-208 | B-208 | 3,5-diCl—Ph | H |
| A-209 | B-209 | 2-Pyridyl | H |
| A-210 | B-210 | 3-Pyridyl | H |
| A-211 | B-211 | 4-Pyridyl | H |
| A-212 | B-212 | 2-Pyrimidyl | H |
| A-213 | B-213 | 1-Pyrrolyl | H |
| A-214 | B-214 | 1-Pyrazolyl | H |
| A-215 | B-215 | 3-Pyrazolyl | H |
| A-216 | B-216 | 1,2,4-Triazol-1-yl | H |
| A-217 | B-217 | 1,2,4-Triazol-3-yl | H |
| A-218 | B-218 | 2-Furanyl | H |
| A-219 | B-219 | 3-Furanyl | H |
| A-220 | B-220 | 2-Thienyl | H |
| A-221 | B-221 | 3-Thienyl | H |
| A-222 | B-222 | 2-Thiazolyl | H |
| A-223 | B-223 | 1,3,4-Thiadiazol-2-yl | H |
| A-224 | B-224 | 3-Isoxazolyl | H |
| A-225 | B-225 | CH$_3$CO | H |
| A-226 | B-226 | CH$_3$CH$_2$CO | H |
| A-227 | B-227 | n-C$_3$H$_7$CO | H |
| A-228 | B-228 | iso-C$_3$H$_7$CO | H |
| A-229 | B-229 | n-C$_4$H$_9$CO | H |
| A-230 | B-230 | iso-C$_4$H$_9$CO | H |
| A-231 | B-231 | sec-C$_4$H$_9$CO | H |
| A-232 | B-232 | tert-C$_4$H$_9$CO | H |
| A-233 | B-233 | n-C$_5$H$_{11}$CO | H |
| A-234 | B-234 | n-C$_6$H$_{12}$CO | H |
| A-235 | B-235 | PhCO | H |
| A-236 | B-236 | PhCH$_2$CO | H |
| A-237 | B-237 | CH$_3$SO$_2$ | H |
| A-238 | B-238 | C$_2$H5SO$_2$ | H |
| A-239 | B-239 | n-C$_3$H$_7$SO$_2$ | H |
| A-240 | B-240 | iso-C$_3$H$_7$SO$_2$ | H |
| A-241 | B-241 | PhCH$_2$SO$_2$ | H |
| A-242 | B-242 | PhSO$_2$ | H |
| A-243 | B-243 | 2-Cl—PhSO$_2$ | H |
| A-244 | B-244 | 3-Cl—PhSO$_2$ | H |
| A-245 | B-245 | 4-Cl—PhSO$_2$ | H |
| A-246 | B-246 | CH$_3$SO$_2$NH | H |
| A-247 | B-247 | PhSO$_2$NH | H |
| A-248 | B-248 | CF$_3$CH$_2$ | H |
| A-249 | B-249 | ClCH$_2$CH$_2$ | H |
| A-250 | B-250 | ClCH$_2$CH$_2$CH$_2$ | H |
| A-251 | B-251 | CH$_3$OCH$_2$CH$_2$ | H |
| A-252 | B-252 | CH$_3$CH$_2$OCH$_2$CH$_2$ | H |
| A-253 | B-253 | CH$_3$OCH$_2$CH$_2$CH$_2$ | H |
| A-254 | B-254 | C$_2$H5OCH$_2$CH$_2$CH$_2$ | H |
| A-255 | B-255 | n-C$_4$H9OCH$_2$CH$_2$CH$_2$ | H |
| A-256 | B-256 | (CH$_3$O)$_2$CHCH$_2$ | H |
| A-257 | B-257 | CH$_3$CONH | H |
| A-258 | B-258 | PhCONH | H |
| A-259 | B-259 | Ph$_2$C=N | H |
| A-260 | B-260 | HOCH$_2$CH$_2$ | H |
| A-261 | B-261 | HOCH$_2$CH$_2$CH$_2$ | H |
| A-262 | B-262 | CH$_3$O$_2$CCH$_2$ | H |
| A-263 | B-263 | CH$_3$O$_2$CCH(CH$_3$) | H |
| A-264 | B-264 | CH$_3$O$_2$CC(CH$_3$)$_2$ | H |
| A-265 | B-265 | NCCH$_2$ | H |
| A-266 | B-266 | NCCH(CH$_3$) | H |
| A-267 | B-267 | NCC(CH$_3$)$_2$ | H |
| A-268 | B-268 | NC(CH$_3$)(iso-C$_3$H$_7$)C | H |
| A-269 | B-269 | HOCH$_2$CH$_2$CH$_2$CH$_2$ | H |
| A-270 | B-270 | CHCCH$_2$O | H |
| A-271 | B-271 | CH$_3$O$_2$CCH$_2$O | H |
| A-272 | B-272 | CH$_3$O$_2$CCH(CH$_3$)O | H |
| A-273 | B-273 | CH$_3$O$_2$CC(CH$_3$)$_2$O | H |
| A-274 | B-274 | (1-pyrrolidinyl)CH$_2$CH$_2$ | H |
| A-275 | B-275 | CH$_2$=CHCH$_2$ | CH$_3$ |
| A-276 | B-276 | CH$_3$CH=CHCH$_2$ | CH$_3$ |
| A-277 | B-277 | CH$_2$=C(CH$_3$)CH$_2$ | CH$_3$ |
| A-278 | B-278 | CH$_2$=CH(CH$_3$)CH | CH$_3$ |
| A-279 | B-279 | CH$_2$=CHCH$_2$CH$_2$ | CH$_3$ |
| A-280 | B-280 | CH$_3$CH=C(CH$_3$)CH$_2$ | CH$_3$ |
| A-281 | B-281 | CH(CH$_3$)HC=CHCH$_3$ | CH$_3$ |
| A-282 | B-282 | C(CH$_3$)$_2$HC=CH$_2$ | CH$_3$ |
| A-283 | B-283 | CH$_2$HC=C(CH$_3$)$_2$ | CH$_3$ |
| A-284 | B-284 | CH$_3$CH=CHCH$_2$CH$_2$ | CH$_3$ |
| A-285 | B-285 | CH$_2$=CHCH$_2$CH$_2$CH$_2$ | CH$_3$ |
| A-286 | B-286 | CHCCH$_2$ | CH$_3$ |
| A-287 | B-287 | CH$_3$CCCH$_2$ | CH$_3$ |
| A-288 | B-288 | CHCCH(CH$_3$) | CH$_3$ |
| A-289 | B-289 | CH$_3$CCCH(CH$_3$) | CH$_3$ |
| A-290 | B-290 | cyclo-C$_3$H5 | CH$_3$ |
| A-291 | B-291 | cyclo-C5H9 | CH$_3$ |
| A-292 | B-292 | cyclo-C6H$_{11}$ | CH$_3$ |
| A-293 | B-293 | (cyclo-C$_3$H5)CH$_2$ | CH$_3$ |
| A-294 | B-294 | (cyclo-C5H9)CH$_2$ | CH$_3$ |
| A-295 | B-295 | (cyclo-C6H$_{11}$)CH$_2$ | CH$_3$ |
| A-296 | B-296 | PhCH$_2$ | CH$_3$ |
| A-297 | B-297 | PhCH(CH$_3$) | CH$_3$ |
| A-298 | B-298 | PhC(CH$_3$)$_2$ | CH$_3$ |
| A-299 | B-299 | PhCH$_2$CH$_2$ | CH$_3$ |
| A-300 | B-300 | (2-F—Ph)CH$_2$ | CH$_3$ |
| A-301 | B-301 | (3-F—Ph)CH$_2$ | CH$_3$ |
| A-302 | B-302 | (4-F—Ph)CH$_2$ | CH$_3$ |
| A-303 | B-303 | (2-Cl—Ph)CH$_2$ | CH$_3$ |
| A-304 | B-304 | (3-Cl—Ph)CH$_2$ | CH$_3$ |
| A-305 | B-305 | (4-Cl—Ph)CH$_2$ | CH$_3$ |
| A-306 | B-306 | (2-CF$_3$—Ph)CH$_2$ | CH$_3$ |
| A-307 | B-307 | (3-CF$_3$—Ph)CH$_2$ | CH$_3$ |
| A-308 | B-308 | (4-CF$_3$—Ph)CH$_2$ | CH$_3$ |
| A-309 | B-309 | (2-CH$_3$O—Ph)CH$_2$ | CH$_3$ |
| A-310 | B-310 | (3-CH$_3$O—Ph)CH$_2$ | CH$_3$ |
| A-311 | B-311 | (4-CH$_3$O—Ph)CH$_2$ | CH$_3$ |
| A-312 | B-312 | HO | CH$_3$ |
| A-313 | B-313 | CH$_3$O | CH$_3$ |
| A-314 | B-314 | CH$_3$CH$_2$O | CH$_3$ |
| A-315 | B-315 | n-C$_3$H7O | CH$_3$ |
| A-316 | B-316 | iso-C$_3$H7O | CH$_3$ |
| A-317 | B-317 | CH$_2$=CHCH$_2$O | CH$_3$ |
| A-318 | B-318 | CH$_2$=C(CH$_3$)CH$_2$O | CH$_3$ |
| A-319 | B-319 | CH$_2$=CHCH(CH$_3$)O | CH$_3$ |
| A-320 | B-320 | CH$_2$=CHCH(CH$_3$)O | CH$_3$ |
| A-321 | B-321 | CH$_2$=CHC(CH$_3$)$_2$O | CH$_3$ |
| A-322 | B-322 | CH$_3$CH=CHCH$_2$O | CH$_3$ |
| A-323 | B-323 | CHCCH$_2$O | CH$_3$ |
| A-324 | B-324 | CH$_3$CCCH$_2$O | CH$_3$ |
| A-325 | B-325 | CHCCH(CH$_3$)O | CH$_3$ |
| A-326 | B-326 | CH$_3$O$_2$CCH(CH$_3$)O | CH$_3$ |
| A-327 | B-327 | CH$_3$O$_2$CC(CH$_3$)$_2$O | CH$_3$ |
| A-328 | B-328 | CH$_3$O$_2$CCH$_2$O | CH$_3$ |
| A-329 | B-329 | PhCH$_2$O | CH$_3$ |
| A-330 | B-330 | PhO | CH$_3$ |
| A-331 | B-331 | NH$_2$ | CH$_3$ |
| A-332 | B-332 | CH$_3$NH | CH$_3$ |
| A-333 | B-333 | C$_2$H5NH | CH$_3$ |
| A-334 | B-334 | n-C$_3$H7NH | CH$_3$ |
| A-335 | B-335 | iso-C$_3$H7NH | CH$_3$ |
| A-336 | B-336 | PhCH$_2$NH | CH$_3$ |
| A-337 | B-337 | PhNH | CH$_3$ |
| A-338 | B-338 | 2-F—PhNH | CH$_3$ |
| A-339 | B-339 | 3-F—PhNH | CH$_3$ |
| A-340 | B-340 | 4-F—PhNH | CH$_3$ |
| A-341 | B-341 | 2-Cl—PhNH | CH$_3$ |
| A-342 | B-342 | 3-Cl—PhNH | CH$_3$ |
| A-343 | B-343 | 4-Cl—PhNH | CH$_3$ |
| A-344 | B-344 | 2-CF$_3$—PhNH | CH$_3$ |
| A-345 | B-345 | 3-CF$_3$—PhNH | CH$_3$ |
| A-346 | B-346 | 2-CH$_3$O—PhNH | CH$_3$ |
| A-347 | B-347 | 3-CH$_3$O—PhNH | CH$_3$ |
| A-348 | B-348 | 4-CH$_3$O—PhNH | CH$_3$ |
| A-349 | B-349 | Ph | CH$_3$ |
| A-350 | B-350 | 2-F—Ph | CH$_3$ |

TABLE I-continued

Compounds of formula (I) in which $R^1$ is —C(=U)NR$^3$R$^4$; $R^2$ is H and m is zero. In Table 1 compounds A-1 to A-881 represent individual compounds in which U is O, whilst compounds B-1 to B-881 represent individual compounds in which U is S.

| Compound | | $R^3$ | $R^4$ |
|---|---|---|---|
| A-351 | B-351 | 3-F—Ph | CH$_3$ |
| A-352 | B-352 | 4-F—Ph | CH$_3$ |
| A-353 | B-353 | 2-Cl—Ph | CH$_3$ |
| A-354 | B-354 | 3-Cl—Ph | CH$_3$ |
| A-355 | B-355 | 4-Cl—Ph | CH$_3$ |
| A-356 | B-356 | 2-Br—Ph | CH$_3$ |
| A-357 | B-357 | 3-Br—Ph | CH$_3$ |
| A-358 | B-358 | 4-Br—Ph | CH$_3$ |
| A-359 | B-359 | 2-I—Ph | CH$_3$ |
| A-360 | B-360 | 3-I—Ph | CH$_3$ |
| A-361 | B-361 | 4-I—Ph | CH$_3$ |
| A-362 | B-362 | 2-CF$_3$—Ph | CH$_3$ |
| A-363 | B-363 | 3-CF$_3$—Ph | CH$_3$ |
| A-364 | B-364 | 4-CF$_3$—Ph | CH$_3$ |
| A-365 | B-365 | 2-CH$_3$—Ph | CH$_3$ |
| A-366 | B-366 | 3-CH$_3$—Ph | CH$_3$ |
| A-367 | B-367 | 4-CH$_3$—Ph | CH$_3$ |
| A-368 | B-368 | 2-CH$_3$O—Ph | CH$_3$ |
| A-369 | B-369 | 3-CH$_3$O—Ph | CH$_3$ |
| A-370 | B-370 | 4-CH$_3$O—Ph | CH$_3$ |
| A-371 | B-371 | 2-NO$_2$—Ph | CH$_3$ |
| A-372 | B-372 | 3-NO$_2$—Ph | CH$_3$ |
| A-373 | B-373 | 4-NO$_2$—Ph | CH$_3$ |
| A-374 | B-374 | 2-CN—Ph | CH$_3$ |
| A-375 | B-375 | 3-CN—Ph | CH$_3$ |
| A-376 | B-376 | 4-CN—Ph | CH$_3$ |
| A-377 | B-377 | 2-CO$_2$Me—Ph | CH$_3$ |
| A-378 | B-378 | 3-CO$_2$Me—Ph | CH$_3$ |
| A-379 | B-379 | 4-CO$_2$Me—Ph | CH$_3$ |
| A-380 | B-380 | 2-HO—Ph | CH$_3$ |
| A-381 | B-381 | 3-HO—Ph | CH$_3$ |
| A-382 | B-382 | 4-HO—Ph | CH$_3$ |
| A-383 | B-383 | 2-NH$_2$—Ph | CH$_3$ |
| A-384 | B-384 | 3-NH$_2$—Ph | CH$_3$ |
| A-385 | B-385 | 4-NH$_2$—Ph | CH$_3$ |
| A-386 | B-386 | 2-CF$_3$O—Ph | CH$_3$ |
| A-387 | B-387 | 3-CF$_3$O—Ph | CH$_3$ |
| A-388 | B-388 | 4-CF$_3$O—Ph | CH$_3$ |
| A-389 | B-389 | 4-CF$_3$CH$_2$O—Ph | CH$_3$ |
| A-390 | B-390 | 4-(4-Cl—PhO)—Ph | CH$_3$ |
| A-391 | B-391 | 4-(4-CF$_3$—PhO)—Ph | CH$_3$ |
| A-392 | B-392 | 2,3-diCl—Ph | CH$_3$ |
| A-393 | B-393 | 2,4-diCl—Ph | CH$_3$ |
| A-394 | B-394 | 2,5-diCl—Ph | CH$_3$ |
| A-395 | B-395 | 2,6-diCl—Ph | CH$_3$ |
| A-396 | B-396 | 3,4-diCl—Ph | CH$_3$ |
| A-397 | B-397 | 3,5-diCl—Ph | CH$_3$ |
| A-398 | B-398 | 2-Pyridyl | CH$_3$ |
| A-399 | B-399 | 3-Pyridyl | CH$_3$ |
| A-400 | B-400 | 4-Pyridyl | CH$_3$ |
| A-401 | B-401 | 2-Pyrimidyl | CH$_3$ |
| A-402 | B-402 | 1-Pyrrolyl | CH$_3$ |
| A-403 | B-403 | 1-Pyrazolyl | CH$_3$ |
| A-404 | B-404 | 3-Pyrazolyl | CH$_3$ |
| A-405 | B-405 | 1,2,4-Triazol-1-yl | CH$_3$ |
| A-406 | B-406 | 1,2,4-Triazol-3-yl | CH$_3$ |
| A-407 | B-407 | 2-Furanyl | CH$_3$ |
| A-408 | B-408 | 3-Furanyl | CH$_3$ |
| A-409 | B-409 | 2-Thienyl | CH$_3$ |
| A-410 | B-410 | 3-Thienyl | CH$_3$ |
| A-411 | B-411 | 2-Thiazolyl | CH$_3$ |
| A-412 | B-412 | 1,3,4-Thiadiazol-2-yl | CH$_3$ |
| A-413 | B-413 | 3-Isoxazolyl | CH$_3$ |
| A-414 | B-414 | CH$_3$CO | CH$_3$ |
| A-415 | B-415 | PhCO | CH$_3$ |
| A-416 | B-416 | PhCH$_2$CO | CH$_3$ |
| A-417 | B-417 | CH$_3$SO$_2$NH | CH$_3$ |
| A-418 | B-418 | PhSO$_2$NH | CH$_3$ |
| A-419 | B-419 | CF$_3$CH$_2$ | CH$_3$ |
| A-420 | B-420 | ClCH$_2$CH$_2$ | CH$_3$ |
| A-421 | B-421 | ClCH$_2$CH$_2$CH$_2$ | CH$_3$ |
| A-422 | B-422 | CH$_3$OCH$_2$CH$_2$ | CH$_3$ |
| A-423 | B-423 | CH$_3$CH$_2$OCH$_2$CH$_2$ | CH$_3$ |
| A-424 | B-424 | CH$_3$OCH$_2$CH$_2$CH$_2$ | CH$_3$ |
| A-425 | B-425 | C$_2$H5OCH$_2$CH$_2$CH$_2$ | CH$_3$ |
| A-426 | B-426 | n-C$_4$H9OCH$_2$CH$_2$CH$_2$ | CH$_3$ |
| A-427 | B-427 | (CH$_3$O)$_2$CHCH$_2$ | CH$_3$ |
| A-428 | B-428 | CH$_3$CONH | CH$_3$ |
| A-429 | B-429 | PhCONH | CH$_3$ |
| A-430 | B-430 | Ph$_2$C=N | CH$_3$ |
| A-431 | B-431 | HOCH$_2$CH$_2$ | CH$_3$ |
| A-432 | B-432 | HOCH$_2$CH$_2$CH$_2$ | CH$_3$ |
| A-433 | B-433 | CH$_3$O$_2$CCH$_2$ | CH$_3$ |
| A-434 | B-434 | CH$_3$O$_2$CCH(CH$_3$) | CH$_3$ |
| A-435 | B-435 | CH$_3$O$_2$CC(CH$_3$)$_2$ | CH$_3$ |
| A-436 | B-436 | NCCH$_2$ | CH$_3$ |
| A-437 | B-437 | NC(CH$_3$)(iso-C$_3$H$_7$)C | CH$_3$ |
| A-438 | B-438 | (1-pyrrolidinyl)CH$_2$CH$_2$ | C$_2$H$_5$ |
| A-439 | B-439 | CH$_2$=CHCH$_2$ | C$_2$H$_5$ |
| A-440 | B-440 | CHCCH$_2$ | C$_2$H$_5$ |
| A-441 | B-441 | CH$_3$CCCH$_2$ | C$_2$H$_5$ |
| A-442 | B-442 | (cyclo-C$_3$H5)CH$_2$ | C$_2$H$_5$ |
| A-443 | B-443 | PhCH$_2$ | C$_2$H$_5$ |
| A-444 | B-444 | PhCH$_2$CH$_2$ | C$_2$H$_5$ |
| A-445 | B-445 | (2-Cl—Ph)CH$_2$ | C$_2$H$_5$ |
| A-446 | B-446 | (3-Cl—Ph)CH$_2$ | C$_2$H$_5$ |
| A-447 | B-447 | (4-Cl—Ph)CH$_2$ | C$_2$H$_5$ |
| A-448 | B-448 | (2-CF$_3$—Ph)CH$_2$ | C$_2$H$_5$ |
| A-449 | B-449 | (3-CF$_3$—Ph)CH$_2$ | C$_2$H$_5$ |
| A-450 | B-450 | (4-CF$_3$—Ph)CH$_2$ | C$_2$H$_5$ |
| A-451 | B-451 | (2-CH$_3$O—Ph)CH$_2$ | C$_2$H$_5$ |
| A-452 | B-452 | (3-CH$_3$O—Ph)CH$_2$ | C$_2$H$_5$ |
| A-453 | B-453 | (4-CH$_3$O—Ph)CH$_2$ | C$_2$H$_5$ |
| A-454 | B-454 | HO | C$_2$H$_5$ |
| A-455 | B-455 | CH$_3$O | C$_2$H$_5$ |
| A-456 | B-456 | CH$_3$CH$_2$O | C$_2$H$_5$ |
| A-457 | B-457 | n-C$_3$H7O | C$_2$H$_5$ |
| A-458 | B-458 | iso-C$_3$H7O | C$_2$H$_5$ |
| A-459 | B-459 | CH$_2$=CHCH$_2$O | C$_2$H$_5$ |
| A-460 | B-460 | CHCCH$_2$O | C$_2$H$_5$ |
| A-461 | B-461 | PhCH$_2$O | C$_2$H$_5$ |
| A-462 | B-462 | PhO | C$_2$H$_5$ |
| A-463 | B-463 | NH$_2$ | C$_2$H$_5$ |
| A-464 | B-464 | CH$_3$NH | C$_2$H$_5$ |
| A-465 | B-465 | C$_2$H5NH | C$_2$H$_5$ |
| A-466 | B-466 | n-C$_3$H7NH | C$_2$H$_5$ |
| A-467 | B-467 | iso-C$_3$H7NH | C$_2$H$_5$ |
| A-468 | B-468 | PhCH$_2$NH | C$_2$H$_5$ |
| A-469 | B-469 | PhNH | C$_2$H$_5$ |
| A-470 | B-470 | 2-Cl—PhNH | C$_2$H$_5$ |
| A-471 | B-471 | 3-Cl—PhNH | C$_2$H$_5$ |
| A-472 | B-472 | 4-Cl—PhNH | C$_2$H$_5$ |
| A-473 | B-473 | 2-CF$_3$—PhNH | C$_2$H$_5$ |
| A-474 | B-474 | 3-CF$_3$—PhNH | C$_2$H$_5$ |
| A-475 | B-475 | 2-CH$_3$O—PhNH | C$_2$H$_5$ |
| A-476 | B-476 | 3-CH$_3$O—PhNH | C$_2$H$_5$ |
| A-477 | B-477 | 4-CH$_3$O—PhNH | C$_2$H$_5$ |
| A-478 | B-478 | Ph | C$_2$H$_5$ |
| A-479 | B-479 | 2-Cl—Ph | C$_2$H$_5$ |
| A-480 | B-480 | 3-Cl—Ph | C$_2$H$_5$ |
| A-481 | B-481 | 4-Cl—Ph | C$_2$H$_5$ |
| A-482 | B-482 | 2-CF$_3$—Ph | C$_2$H$_5$ |
| A-483 | B-483 | 3-CF$_3$—Ph | C$_2$H$_5$ |
| A-484 | B-484 | 4-CF$_3$—Ph | C$_2$H$_5$ |
| A-485 | B-485 | 2-CH$_3$O—Ph | C$_2$H$_5$ |
| A-486 | B-486 | 3-CH$_3$O—Ph | C$_2$H$_5$ |
| A-487 | B-487 | 4-CH$_3$O—Ph | C$_2$H$_5$ |
| A-488 | B-488 | 2-HO—Ph | C$_2$H$_5$ |
| A-489 | B-489 | 3-HO—Ph | C$_2$H$_5$ |
| A-490 | B-490 | 4-HO—Ph | C$_2$H$_5$ |
| A-491 | B-491 | 2-NH$_2$—Ph | C$_2$H$_5$ |
| A-492 | B-492 | 3-NH$_2$—Ph | C$_2$H$_5$ |
| A-493 | B-493 | 4-NH$_2$—Ph | C$_2$H$_5$ |
| A-494 | B-494 | 2-HOCH$_2$—Ph | C$_2$H$_5$ |

TABLE I-continued

Compounds of formula (I) in which $R^1$ is —C(=U)NR$^3$R$^4$; $R^2$ is H and m is zero. In Table 1 compounds A-1 to A-881 represent individual compounds in which U is O, whilst compounds B-1 to B-881 represent individual compounds in which U is S.

| Compound | | R$^3$ | R$^4$ |
|---|---|---|---|
| A-495 | B-495 | 4-CF$_3$O—Ph | C$_2$H$_5$ |
| A-496 | B-496 | 4-CF$_3$CH$_2$O—Ph | C$_2$H$_5$ |
| A-497 | B-497 | 4-(4-Cl—PhO)—Ph | C$_2$H$_5$ |
| A-498 | B-498 | 4-(4-CF$_3$—PhO)—Ph | C$_2$H$_5$ |
| A-499 | B-499 | 2,3-diCl—Ph | C$_2$H$_5$ |
| A-500 | B-500 | 1-Pyrrolyl | C$_2$H$_5$ |
| A-501 | B-501 | 1-Pyrazolyl | C$_2$H$_5$ |
| A-502 | B-502 | 1,2,4-Triazol-1-yl | C$_2$H$_5$ |
| A-503 | B-503 | 2-Thiazolyl | C$_2$H$_5$ |
| A-504 | B-504 | 1,3,4-Thiadiazol-2-yl | C$_2$H$_5$ |
| A-505 | B-505 | CH$_3$CO | C$_2$H$_5$ |
| A-506 | B-506 | PhCO | C$_2$H$_5$ |
| A-507 | B-507 | PhSO$_2$NH | C$_2$H$_5$ |
| A-508 | B-508 | CF$_3$CH$_2$ | C$_2$H$_5$ |
| A-509 | B-509 | ClCH$_2$CH$_2$ | C$_2$H$_5$ |
| A-510 | B-510 | ClCH$_2$CH$_2$CH$_2$ | C$_2$H$_5$ |
| A-511 | B-511 | CH$_3$OCH$_2$CH$_2$ | C$_2$H$_5$ |
| A-512 | B-512 | CH$_3$CH$_2$OCH$_2$CH$_2$ | C$_2$H$_5$ |
| A-513 | B-513 | CH$_3$OCH$_2$CH$_2$CH$_2$ | C$_2$H$_5$ |
| A-514 | B-514 | C$_2$H$_5$OCH$_2$CH$_2$CH$_2$ | C$_2$H$_5$ |
| A-515 | B-515 | n-C$_4$H$_9$OCH$_2$CH$_2$CH$_2$ | C$_2$H$_5$ |
| A-516 | B-516 | (CH$_3$O)$_2$CHCH$_2$ | C$_2$H$_5$ |
| A-517 | B-517 | CH$_3$CONH | C$_2$H$_5$ |
| A-518 | B-518 | PhCONH | C$_2$H$_5$ |
| A-519 | B-519 | HOCH$_2$CH$_2$ | C$_2$H$_5$ |
| A-520 | B-520 | HOCH$_2$CH$_2$CH$_2$ | C$_2$H$_5$ |
| A-521 | B-521 | CH$_3$O$_2$CCH$_2$ | C$_2$H$_5$ |
| A-522 | B-522 | CH$_3$O$_2$CCH(CH$_3$) | C$_2$H$_5$ |
| A-523 | B-523 | NCCH$_2$ | n-C$_3$H$_7$ |
| A-524 | B-524 | HOCH$_2$CH$_2$ | n-C$_3$H$_7$ |
| A-525 | B-525 | CH$_2$=CHCH$_2$ | iso-C$_3$H$_7$ |
| A-526 | B-526 | CHCCH$_2$ | iso-C$_3$H$_7$ |
| A-527 | B-527 | CH$_3$CCCH$_2$ | iso-C$_3$H$_7$ |
| A-528 | B-528 | (cyclo-C$_3$H$_5$)CH$_2$ | iso-C$_3$H$_7$ |
| A-529 | B-529 | PhCH$_2$ | iso-C$_3$H$_7$ |
| A-530 | B-530 | PhCH$_2$CH$_2$ | iso-C$_3$H$_7$ |
| A-531 | B-531 | (2-Cl—Ph)CH$_2$ | iso-C$_3$H$_7$ |
| A-532 | B-532 | (3-Cl—Ph)CH$_2$ | iso-C$_3$H$_7$ |
| A-533 | B-533 | (4-Cl—Ph)CH$_2$ | iso-C$_3$H$_7$ |
| A-534 | B-534 | (2-CF$_3$—Ph)CH$_2$ | iso-C$_3$H$_7$ |
| A-535 | B-535 | (3-CF$_3$—Ph)CH$_2$ | iso-C$_3$H$_7$ |
| A-536 | B-536 | (4-CF$_3$—Ph)CH$_2$ | iso-C$_3$H$_7$ |
| A-537 | B-537 | (2-CH$_3$O—Ph)CH$_2$ | iso-C$_3$H$_7$ |
| A-538 | B-538 | (3-CH$_3$O—Ph)CH$_2$ | iso-C$_3$H$_7$ |
| A-539 | B-539 | (4-CH$_3$O—Ph)CH$_2$ | iso-C$_3$H$_7$ |
| A-540 | B-540 | HO | iso-C$_3$H$_7$ |
| A-541 | B-541 | CH$_3$O | iso-C$_3$H$_7$ |
| A-542 | B-542 | CH$_3$CH$_2$O | iso-C$_3$H$_7$ |
| A-543 | B-543 | n-C$_3$H$_7$O | iso-C$_3$H$_7$ |
| A-544 | B-544 | iso-C$_3$H$_7$O | iso-C$_3$H$_7$ |
| A-545 | B-545 | CH$_2$=CHCH$_2$O | iso-C$_3$H$_7$ |
| A-546 | B-546 | CHCCH$_2$O | iso-C$_3$H$_7$ |
| A-547 | B-547 | PhCH$_2$O | iso-C$_3$H$_7$ |
| A-548 | B-548 | PhO | iso-C$_3$H$_7$ |
| A-549 | B-549 | NH$_2$ | iso-C$_3$H$_7$ |
| A-550 | B-550 | CH$_3$NH | iso-C$_3$H$_7$ |
| A-551 | B-551 | C$_2$H$_5$NH | iso-C$_3$H$_7$ |
| A-552 | B-552 | n-C$_3$H$_7$NH | iso-C$_3$H$_7$ |
| A-553 | B-553 | iso-C$_3$H$_7$NH | iso-C$_3$H$_7$ |
| A-554 | B-554 | PhCH$_2$NH | iso-C$_3$H$_7$ |
| A-555 | B-555 | PhNH | iso-C$_3$H$_7$ |
| A-556 | B-556 | 2-Cl—PhNH | iso-C$_3$H$_7$ |
| A-557 | B-557 | 3-Cl—PhNH | iso-C$_3$H$_7$ |
| A-558 | B-558 | 4-Cl—PhNH | iso-C$_3$H$_7$ |
| A-559 | B-559 | 2-CF$_3$—PhNH | iso-C$_3$H$_7$ |
| A-560 | B-560 | 3-CF$_3$—PhNH | iso-C$_3$H$_7$ |
| A-561 | B-561 | 2-CH$_3$O—PhNH | iso-C$_3$H$_7$ |
| A-562 | B-562 | 3-CH$_3$O—PhNH | iso-C$_3$H$_7$ |
| A-563 | B-563 | 4-CH$_3$O—PhNH | iso-C$_3$H$_7$ |
| A-564 | B-564 | Ph | iso-C$_3$H$_7$ |
| A-565 | B-565 | 2-Cl—Ph | iso-C$_3$H$_7$ |
| A-566 | B-566 | 3-Cl—Ph | iso-C$_3$H$_7$ |
| A-567 | B-567 | 4-Cl—Ph | iso-C$_3$H$_7$ |
| A-568 | B-568 | 2-CF$_3$—Ph | iso-C$_3$H$_7$ |
| A-569 | B-569 | 3-CF$_3$—Ph | iso-C$_3$H$_7$ |
| A-570 | B-570 | 4-CF$_3$—Ph | iso-C$_3$H$_7$ |
| A-571 | B-571 | 2-CH$_3$O—Ph | iso-C$_3$H$_7$ |
| A-572 | B-572 | 3-CH$_3$O—Ph | iso-C$_3$H$_7$ |
| A-573 | B-573 | 4-CH$_3$O—Ph | iso-C$_3$H$_7$ |
| A-574 | B-574 | 2-HO—Ph | iso-C$_3$H$_7$ |
| A-575 | B-575 | 3-HO—Ph | iso-C$_3$H$_7$ |
| A-576 | B-576 | 4-HO—Ph | iso-C$_3$H$_7$ |
| A-577 | B-577 | 2-NH$_2$—Ph | iso-C$_3$H$_7$ |
| A-578 | B-578 | 3-NH$_2$—Ph | iso-C$_3$H$_7$ |
| A-579 | B-579 | 4-NH$_2$—Ph | iso-C$_3$H$_7$ |
| A-580 | B-580 | 2-HOCH$_2$—Ph | iso-C$_3$H$_7$ |
| A-581 | B-581 | 4-CF$_3$O—Ph | iso-C$_3$H$_7$ |
| A-582 | B-582 | 4-CF$_3$CH$_2$O—Ph | iso-C$_3$H$_7$ |
| A-583 | B-583 | 4-(4-Cl—PhO)—Ph | iso-C$_3$H$_7$ |
| A-584 | B-584 | 4-(4-CF$_3$—PhO)—Ph | iso-C$_3$H$_7$ |
| A-585 | B-585 | 2,3-diCl—Ph | iso-C$_3$H$_7$ |
| A-586 | B-586 | 1-Pyrrolyl | iso-C$_3$H$_7$ |
| A-587 | B-587 | 1-Pyrazolyl | iso-C$_3$H$_7$ |
| A-588 | B-588 | 1,2,4-Triazol-1-yl | iso-C$_3$H$_7$ |
| A-589 | B-589 | 2-Thiazolyl | iso-C$_3$H$_7$ |
| A-590 | B-590 | 1,3,4-Thiadiazol-2-yl | iso-C$_3$H$_7$ |
| A-591 | B-591 | CH$_3$CO | iso-C$_3$H$_7$ |
| A-592 | B-592 | PhCO | iso-C$_3$H$_7$ |
| A-593 | B-593 | PhSO$_2$NH | iso-C$_3$H$_7$ |
| A-594 | B-594 | CF$_3$CH$_2$ | iso-C$_3$H$_7$ |
| A-595 | B-595 | ClCH$_2$CH$_2$ | iso-C$_3$H$_7$ |
| A-596 | B-596 | ClCH$_2$CH$_2$CH$_2$ | iso-C$_3$H$_7$ |
| A-597 | B-597 | CH$_3$OCH$_2$CH$_2$ | iso-C$_3$H$_7$ |
| A-598 | B-598 | CH$_3$CH$_2$OCH$_2$CH$_2$ | iso-C$_3$H$_7$ |
| A-599 | B-599 | CH$_3$OCH$_2$CH$_2$CH$_2$ | iso-C$_3$H$_7$ |
| A-600 | B-600 | C$_2$H$_5$OCH$_2$CH$_2$CH$_2$ | iso-C$_3$H$_7$ |
| A-601 | B-601 | n-C$_4$H$_9$OCH$_2$CH$_2$CH$_2$ | iso-C$_3$H$_7$ |
| A-602 | B-602 | (CH$_3$O)$_2$CHCH$_2$ | iso-C$_3$H$_7$ |
| A-603 | B-603 | CH$_3$CONH | iso-C$_3$H$_7$ |
| A-604 | B-604 | PhCONH | iso-C$_3$H$_7$ |
| A-605 | B-605 | HOCH$_2$CH$_2$ | iso-C$_3$H$_7$ |
| A-606 | B-606 | HOCH$_2$CH$_2$CH$_2$ | iso-C$_3$H$_7$ |
| A-607 | B-607 | CH$_3$O$_2$CCH$_2$ | iso-C$_3$H$_7$ |
| A-608 | B-608 | CH$_3$O$_2$CCH(CH$_3$) | iso-C$_3$H$_7$ |
| A-609 | B-609 | NCCH$_2$ | iso-C$_3$H$_7$ |
| A-610 | B-610 | NC(CH$_3$)(iso-C$_3$H$_7$) | tert-C$_4$H$_9$ |
| A-611 | B-611 | CH$_2$=CHCH$_2$ | tert-C$_4$H$_9$ |
| A-612 | B-612 | CHCCH$_2$ | tert-C$_4$H$_9$ |
| A-613 | B-613 | CH$_3$CCCH$_2$ | tert-C$_4$H$_9$ |
| A-614 | B-614 | (cyclo-C$_3$H$_5$)CH$_2$ | tert-C$_4$H$_9$ |
| A-615 | B-615 | PhCH$_2$ | tert-C$_4$H$_9$ |
| A-616 | B-616 | PhCH$_2$CH$_2$ | tert-C$_4$H$_9$ |
| A-617 | B-617 | (2-Cl—Ph)CH$_2$ | tert-C$_4$H$_9$ |
| A-618 | B-618 | (3-Cl—Ph)CH$_2$ | tert-C$_4$H$_9$ |
| A-619 | B-619 | (4-Cl—Ph)CH$_2$ | tert-C$_4$H$_9$ |
| A-620 | B-620 | (2-CF$_3$—Ph)CH$_2$ | tert-C$_4$H$_9$ |
| A-621 | B-621 | (3-CF$_3$—Ph)CH$_2$ | tert-C$_4$H$_9$ |
| A-622 | B-622 | (4-CF$_3$—Ph)CH$_2$ | tert-C$_4$H$_9$ |
| A-623 | B-623 | (2-CH$_3$O—Ph)CH$_2$ | tert-C$_4$H$_9$ |
| A-624 | B-624 | (3-CH$_3$O—Ph)CH$_2$ | tert-C$_4$H$_9$ |
| A-625 | B-625 | (4-CH$_3$O—Ph)CH$_2$ | tert-C$_4$H$_9$ |
| A-626 | B-626 | HO | tert-C$_4$H$_9$ |
| A-627 | B-627 | CH$_3$O | tert-C$_4$H$_9$ |
| A-628 | B-628 | CH$_3$CH$_2$O | tert-C$_4$H$_9$ |
| A-629 | B-629 | n-C$_3$H$_7$O | tert-C$_4$H$_9$ |
| A-630 | B-630 | iso-C$_3$H$_7$O | tert-C$_4$H$_9$ |
| A-631 | B-631 | CH$_2$=CHCH$_2$O | tert-C$_4$H$_9$ |
| A-632 | B-632 | CHCCH$_2$O | tert-C$_4$H$_9$ |
| A-633 | B-633 | PhCH$_2$O | tert-C$_4$H$_9$ |
| A-634 | B-634 | PhO | tert-C$_4$H$_9$ |
| A-635 | B-635 | NH$_2$ | tert-C$_4$H$_9$ |
| A-636 | B-636 | CH$_3$NH | tert-C$_4$H$_9$ |
| A-637 | B-637 | C$_2$H$_5$NH | tert-C$_4$H$_9$ |
| A-638 | B-638 | n-C$_3$H$_7$NH | tert-C$_4$H$_9$ |

TABLE I-continued

Compounds of formula (I) in which R¹ is —C(=U)NR³R⁴; R² is H and m is zero. In Table 1 compounds A-1 to A-881 represent individual compounds in which U is O, whilst compounds B-1 to B-881 represent individual compounds in which U is S.

| Compound | | R³ | R⁴ |
|---|---|---|---|
| A-639 | B-639 | iso-C₃H7NH | tert-C₄H₉ |
| A-640 | B-640 | PhCH₂NH | tert-C₄H₉ |
| A-641 | B-641 | PhNH | tert-C₄H₉ |
| A-642 | B-642 | 2-Cl—PhNH | tert-C₄H₉ |
| A-643 | B-643 | 3-Cl—PhNH | tert-C₄H₉ |
| A-644 | B-644 | 4-Cl—PhNH | tert-C₄H₉ |
| A-645 | B-645 | 2-CF₃—PhNH | tert-C₄H₉ |
| A-646 | B-646 | 3-CF₃—PhNH | tert-C₄H₉ |
| A-647 | B-647 | 2-CH₃O—PhNH | tert-C₄H₉ |
| A-648 | B-648 | 3-CH₃O—PhNH | tert-C₄H₉ |
| A-649 | B-649 | 4-CH₃O—PhNH | tert-C₄H₉ |
| A-650 | B-650 | Ph | tert-C₄H₉ |
| A-651 | B-651 | 2-Cl—Ph | tert-C₄H₉ |
| A-652 | B-652 | 3-Cl—Ph | tert-C₄H₉ |
| A-653 | B-653 | 4-Cl—Ph | tert-C₄H₉ |
| A-654 | B-654 | 2-CF₃—Ph | tert-C₄H₉ |
| A-655 | B-655 | 3-CF₃—Ph | tert-C₄H₉ |
| A-656 | B-656 | 4-CF₃—Ph | tert-C₄H₉ |
| A-657 | B-657 | 2-CH₃O—Ph | tert-C₄H₉ |
| A-658 | B-658 | 3-CH₃O—Ph | tert-C₄H₉ |
| A-659 | B-659 | 4-CH₃O—Ph | tert-C₄H₉ |
| A-660 | B-660 | 2-HO—Ph | tert-C₄H₉ |
| A-661 | B-661 | 3-HO—Ph | tert-C₄H₉ |
| A-662 | B-662 | 4-HO—Ph | tert-C₄H₉ |
| A-663 | B-663 | 2-NH₂—Ph | tert-C₄H₉ |
| A-664 | B-664 | 3-NH₂—Ph | tert-C₄H₉ |
| A-665 | B-665 | 4-NH₂—Ph | tert-C₄H₉ |
| A-666 | B-666 | 2-HOCH₂—Ph | tert-C₄H₉ |
| A-667 | B-667 | 4-CF₃O—Ph | tert-C₄H₉ |
| A-668 | B-668 | 4-CF₃CH₂O—Ph | tert-C₄H₉ |
| A-669 | B-669 | 4-(4-Cl—PhO)—Ph | tert-C₄H₉ |
| A-670 | B-670 | 4-(4-CF₃—PhO)—Ph | tert-C₄H₉ |
| A-671 | B-671 | 2,3-diCl—Ph | tert-C₄H₉ |
| A-672 | B-672 | 1-Pyrrolyl | tert-C₄H₉ |
| A-673 | B-673 | 1-Pyrazolyl | tert-C₄H₉ |
| A-674 | B-674 | 1,2,4-Triazol-1-yl | tert-C₄H₉ |
| A-675 | B-675 | 2-Thiazolyl | tert-C₄H₉ |
| A-676 | B-676 | 1,3,4-Thiadiazol-2-yl | tert-C₄H₉ |
| A-677 | B-677 | CH₃CO | tert-C₄H₉ |
| A-678 | B-678 | PhCO | tert-C₄H₉ |
| A-679 | B-679 | PhSO₂NH | tert-C₄H₉ |
| A-680 | B-680 | CF₃CH₂ | tert-C₄H₉ |
| A-681 | B-681 | ClCH₂CH₂ | tert-C₄H₉ |
| A-682 | B-682 | ClCH₂CH₂CH₂ | tert-C₄H₉ |
| A-683 | B-683 | CH₃OCH₂CH₂ | tert-C₄H₉ |
| A-684 | B-684 | CH₃CH₂OCH₂CH₂ | tert-C₄H₉ |
| A-685 | B-685 | CH₃OCH₂CH₂CH₂ | tert-C₄H₉ |
| A-686 | B-686 | C₂H₅OCH₂CH₂CH₂ | tert-C₄H₉ |
| A-687 | B-687 | n-C₄H9OCH₂CH₂CH₂ | tert-C₄H₉ |
| A-688 | B-688 | (CH₃O)₂CHCH₂ | tert-C₄H₉ |
| A-689 | B-689 | CH₃CONH | tert-C₄H₉ |
| A-690 | B-690 | PhCONH | tert-C₄H₉ |
| A-691 | B-691 | HOCH₂CH₂ | tert-C₄H₉ |
| A-692 | B-692 | HOCH₂CH₂CH₂ | tert-C₄H₉ |
| A-693 | B-693 | CH₃O₂CCH₂ | tert-C₄H₉ |
| A-694 | B-694 | CH₃O₂CCH(CH₃) | tert-C₄H₉ |
| A-695 | B-695 | NCCH₂ | tert-C₄H₉ |
| A-696 | B-696 | NC(CH₃)(iso-C₃H7)C | CH₂=CHCH₂ |
| A-697 | B-697 | CH₂=CHCH₂ | CH₂=CHCH₂ |
| A-698 | B-698 | CHCCH₂ | CH₂=CHCH₂ |
| A-699 | B-699 | CH₃CCCH₂ | CH₂=CHCH₂ |
| A-700 | B-700 | (cyclo-C₃H5)CH₂ | CH₂=CHCH₂ |
| A-701 | B-701 | PhCH₂ | CH₂=CHCH₂ |
| A-702 | B-702 | PhCH₂CH₂ | CH₂=CHCH₂ |
| A-703 | B-703 | (2-Cl—Ph)CH₂ | CH₂=CHCH₂ |
| A-704 | B-704 | (3-Cl—Ph)CH₂ | CH₂=CHCH₂ |
| A-705 | B-705 | (4-Cl—Ph)CH₂ | CH₂=CHCH₂ |
| A-706 | B-706 | (2-CF₃—Ph)CH₂ | CH₂=CHCH₂ |
| A-707 | B-707 | (3-CF₃—Ph)CH₂ | CH₂=CHCH₂ |
| A-708 | B-708 | (4-CF₃—Ph)CH₂ | CH₂=CHCH₂ |
| A-709 | B-709 | (2-CH₃O—Ph)CH₂ | CH₂=CHCH₂ |
| A-710 | B-710 | (3-CH₃O—Ph)CH₂ | CH₂=CHCH₂ |
| A-711 | B-711 | (4-CH₃O—Ph)CH₂ | CH₂=CHCH₂ |
| A-712 | B-712 | HO | CH₂=CHCH₂ |
| A-713 | B-713 | CH₃O | CH₂=CHCH₂ |
| A-714 | B-714 | CH₃CH₂O | CH₂=CHCH₂ |
| A-715 | B-715 | n-C₃H7O | CH₂=CHCH₂ |
| A-716 | B-716 | iso-C₃H7O | CH₂=CHCH₂ |
| A-717 | B-717 | CH₂=CHCH₂O | CH₂=CHCH₂ |
| A-718 | B-718 | CHCCH₂O | CH₂=CHCH₂ |
| A-719 | B-719 | PhCH₂O | CH₂=CHCH₂ |
| A-720 | B-720 | PhO | CH₂=CHCH₂ |
| A-721 | B-721 | NH₂ | CH₂=CHCH₂ |
| A-722 | B-722 | CH₃NH | CH₂=CHCH₂ |
| A-723 | B-723 | C₂H5NH | CH₂=CHCH₂ |
| A-724 | B-724 | n-C₃H7NH | CH₂=CHCH₂ |
| A-725 | B-725 | iso-C₃H7NH | CH₂=CHCH₂ |
| A-726 | B-726 | PhCH₂NH | CH₂=CHCH₂ |
| A-727 | B-727 | PhNH | CH₂=CHCH₂ |
| A-728 | B-728 | 2-Cl—PhNH | CH₂=CHCH₂ |
| A-729 | B-729 | 3-Cl—PhNH | CH₂=CHCH₂ |
| A-730 | B-730 | 4-Cl—PhNH | CH₂=CHCH₂ |
| A-731 | B-731 | 2-CF₃—PhNH | CH₂=CHCH₂ |
| A-732 | B-732 | 3-CF₃—PhNH | CH₂=CHCH₂ |
| A-733 | B-733 | 2-CH₃O—PhNH | CH₂=CHCH₂ |
| A-734 | B-734 | 3-CH₃O—PhNH | CH₂=CHCH₂ |
| A-735 | B-735 | 4-CH₃O—PhNH | CH₂=CHCH₂ |
| A-736 | B-736 | Ph | CH₂=CHCH₂ |
| A-737 | B-737 | 2-Cl—Ph | CH₂=CHCH₂ |
| A-738 | B-738 | 3-Cl—Ph | CH₂=CHCH₂ |
| A-739 | B-739 | 4-Cl—Ph | CH₂=CHCH₂ |
| A-740 | B-740 | 2-CF₃—Ph | CH₂=CHCH₂ |
| A-741 | B-741 | 3-CF₃—Ph | CH₂=CHCH₂ |
| A-742 | B-742 | 4-CF₃—Ph | CH₂=CHCH₂ |
| A-743 | B-743 | 2-CH₃O—Ph | CH₂=CHCH₂ |
| A-744 | B-744 | 3-CH₃O—Ph | CH₂=CHCH₂ |
| A-745 | B-745 | 4-CH₃O—Ph | CH₂=CHCH₂ |
| A-746 | B-746 | 2-HO—Ph | CH₂=CHCH₂ |
| A-747 | B-747 | 3-HO—Ph | CH₂=CHCH₂ |
| A-748 | B-748 | 4-HO—Ph | CH₂=CHCH₂ |
| A-749 | B-749 | 2-NH₂—Ph | CH₂=CHCH₂ |
| A-750 | B-750 | 3-NH₂—Ph | CH₂=CHCH₂ |
| A-751 | B-751 | 4-NH₂—Ph | CH₂=CHCH₂ |
| A-752 | B-752 | 2-HOCH₂—Ph | CH₂=CHCH₂ |
| A-753 | B-753 | 4-CF₃O—Ph | CH₂=CHCH₂ |
| A-754 | B-754 | 4-CF₃CH₂O—Ph | CH₂=CHCH₂ |
| A-755 | B-755 | 4-(4-Cl—PhO)—Ph | CH₂=CHCH₂ |
| A-756 | B-756 | 4-(4-CF₃—PhO)—Ph | CH₂=CHCH₂ |
| A-757 | B-757 | 2,3-diCl—Ph | CH₂=CHCH₂ |
| A-758 | B-758 | 1-Pyrrolyl | CH₂=CHCH₂ |
| A-759 | B-759 | 1-Pyrazolyl | CH₂=CHCH₂ |
| A-760 | B-760 | 1,2,4-Triazol-1-yl | CH₂=CHCH₂ |
| A-761 | B-761 | 2-Thiazolyl | CH₂=CHCH₂ |
| A-762 | B-762 | 1,3,4-Thiadiazol-2-yl | CH₂=CHCH₂ |
| A-763 | B-763 | CH₃CO | CH₂=CHCH₂ |
| A-764 | B-764 | PhCO | CH₂=CHCH₂ |
| A-765 | B-765 | PhSO₂NH | CH₂=CHCH₂ |
| A-766 | B-766 | CF₃CH₂ | CH₂=CHCH₂ |
| A-767 | B-767 | ClCH₂CH₂ | CH₂=CHCH₂ |
| A-768 | B-768 | ClCH₂CH₂CH₂ | CH₂=CHCH₂ |
| A-769 | B-769 | CH₃OCH₂CH₂ | CH₂=CHCH₂ |
| A-770 | B-770 | CH₃CH₂OCH₂CH₂ | CH₂=CHCH₂ |
| A-771 | B-771 | CH₃OCH₂CH₂CH₂ | CH₂=CHCH₂ |
| A-772 | B-772 | C₂H5OCH₂CH₂CH₂ | CH₂=CHCH₂ |
| A-773 | B-773 | n-C4H9OCH₂CH₂CH₂ | CH₂=CHCH₂ |
| A-774 | B-774 | (CH₃O)₂CHCH₂ | CH₂=CHCH₂ |
| A-775 | B-775 | CH₃CONH | CH₂=CHCH₂ |
| A-776 | B-776 | PhCONH | CH₂=CHCH₂ |
| A-777 | B-777 | HOCH₂CH₂ | CH₂=CHCH₂ |
| A-778 | B-778 | HOCH₂CH₂CH₂ | CH₂=CHCH₂ |
| A-779 | B-779 | CH₃O₂CCH₂ | CH₂=CHCH₂ |
| A-780 | B-780 | CH₃O₂CCH(CH₃) | CH₂=CHCH₂ |
| A-781 | B-781 | NCCH₂ | CH₂=CHCH₂ |
| A-782 | B-782 | NC(CH₃)(iso-C₃H7)C | PhCH₂ |

TABLE I-continued

Compounds of formula (I) in which $R^1$ is —C(=U)$NR^3R^4$; $R^2$ is H and m is zero. In Table 1 compounds A-1 to A-881 represent individual compounds in which U is O, whilst compounds B-1 to B-881 represent individual compounds in which U is S.

| Compound | | $R^3$ | $R^4$ |
|---|---|---|---|
| A-783 | B-783 | CH$_2$=CHCH$_2$ | PhCH$_2$ |
| A-784 | B-784 | CHCCH$_2$ | PhCH$_2$ |
| A-785 | B-785 | CH$_3$CCCH$_2$ | PhCH$_2$ |
| A-786 | B-786 | (cyclo-C$_3$H$_5$)CH$_2$ | PhCH$_2$ |
| A-787 | B-787 | PhCH$_2$ | PhCH$_2$ |
| A-788 | B-788 | PhCH$_2$CH$_2$ | PhCH$_2$ |
| A-789 | B-789 | (2-Cl—Ph)CH$_2$ | PhCH$_2$ |
| A-790 | B-790 | (3-Cl—Ph)CH$_2$ | PhCH$_2$ |
| A-791 | B-791 | (4-Cl—Ph)CH$_2$ | PhCH$_2$ |
| A-792 | B-792 | (2-CF$_3$—Ph)CH$_2$ | PhCH$_2$ |
| A-793 | B-793 | (3-CF$_3$—Ph)CH$_2$ | PhCH$_2$ |
| A-794 | B-794 | (4-CF$_3$—Ph)CH$_2$ | PhCH$_2$ |
| A-795 | B-795 | (2-CH$_3$O—Ph)CH$_2$ | PhCH$_2$ |
| A-796 | B-796 | (3-CH$_3$O—Ph)CH$_2$ | PhCH$_2$ |
| A-797 | B-797 | (4-CH$_3$O—Ph)CH$_2$ | PhCH$_2$ |
| A-798 | B-798 | HO | PhCH$_2$ |
| A-799 | B-799 | CH$_3$O | PhCH$_2$ |
| A-800 | B-800 | CH$_3$CH$_2$O | PhCH$_2$ |
| A-801 | B-801 | n-C$_3$H$_7$O | PhCH$_2$ |
| A-802 | B-802 | iso-C$_3$H$_7$O | PhCH$_2$ |
| A-803 | B-803 | CH$_2$=CHCH$_2$O | PhCH$_2$ |
| A-804 | B-804 | CHCCH$_2$O | PhCH$_2$ |
| A-805 | B-805 | PhCH$_2$O | PhCH$_2$ |
| A-806 | B-806 | PhO | PhCH$_2$ |
| A-807 | B-807 | NH$_2$ | PhCH$_2$ |
| A-808 | B-808 | CH$_3$NH | PhCH$_2$ |
| A-809 | B-809 | C$_2$H$_5$NH | PhCH$_2$ |
| A-810 | B-810 | n-C$_3$H$_7$NH | PhCH$_2$ |
| A-811 | B-811 | iso-C$_3$H$_7$NH | PhCH$_2$ |
| A-812 | B-812 | PhCH$_2$NH | PhCH$_2$ |
| A-813 | B-813 | PhNH | PhCH$_2$ |
| A-814 | B-814 | 2-Cl—PhNH | PhCH$_2$ |
| A-815 | B-815 | 3-Cl—PhNH | PhCH$_2$ |
| A-816 | B-816 | 4-Cl—PhNH | PhCH$_2$ |
| A-817 | B-817 | 2-CF$_3$—PhNH | PhCH$_2$ |
| A-818 | B-818 | 3-CF$_3$—PhNH | PhCH$_2$ |
| A-819 | B-819 | 2-CH$_3$O—PhNH | PhCH$_2$ |
| A-820 | B-820 | 3-CH$_3$O—PhNH | PhCH$_2$ |
| A-821 | B-821 | 4-CH$_3$O—PhNH | PhCH$_2$ |
| A-822 | B-822 | Ph | PhCH$_2$ |
| A-823 | B-823 | 2-Cl—Ph | PhCH$_2$ |
| A-824 | B-824 | 3-Cl—Ph | PhCH$_2$ |
| A-825 | B-825 | 4-Cl—Ph | PhCH$_2$ |
| A-826 | B-826 | 2-CF$_3$—Ph | PhCH$_2$ |
| A-827 | B-827 | 3-CF$_3$—Ph | PhCH$_2$ |
| A-828 | B-828 | 4-CF$_3$—Ph | PhCH$_2$ |
| A-829 | B-829 | 2-CH$_3$O—Ph | PhCH$_2$ |
| A-830 | B-830 | 3-CH$_3$O—Ph | PhCH$_2$ |
| A-831 | B-831 | 4-CH$_3$O—Ph | PhCH$_2$ |
| A-832 | B-832 | 2-HO—Ph | PhCH$_2$ |
| A-833 | B-833 | 3-HO—Ph | PhCH$_2$ |
| A-834 | B-834 | 4-HO—Ph | PhCH$_2$ |
| A-835 | B-835 | 2-NH$_2$—Ph | PhCH$_2$ |
| A-836 | B-836 | 3-NH$_2$—Ph | PhCH$_2$ |
| A-837 | B-837 | 4-NH$_2$—Ph | PhCH$_2$ |
| A-838 | B-838 | 2-HOCH$_2$—Ph | PhCH$_2$ |
| A-839 | B-839 | 4-CF$_3$O—Ph | PhCH$_2$ |
| A-840 | B-840 | 4-CF$_3$CH$_2$O—Ph | PhCH$_2$ |
| A-841 | B-841 | 4-(4-Cl—PhO)—Ph | PhCH$_2$ |
| A-842 | B-842 | 4-(4-CF$_3$—PhO)—Ph | PhCH$_2$ |
| A-843 | B-843 | 2,3-diCl—Ph | PhCH$_2$ |
| A-844 | B-844 | 1-Pyrrolyl | PhCH$_2$ |
| A-845 | B-845 | 1-Pyrazolyl | PhCH$_2$ |
| A-846 | B-846 | 1,2,4-Triazol-1-yl | PhCH$_2$ |
| A-847 | B-847 | 2-Thiazolyl | PhCH$_2$ |
| A-848 | B-848 | 1,3,4-Thiadiazol-2-yl | PhCH$_2$ |
| A-849 | B-849 | CH$_3$CO | PhCH$_2$ |
| A-850 | B-850 | PhCO | PhCH$_2$ |
| A-851 | B-851 | PhSO$_2$NH | PhCH$_2$ |
| A-852 | B-852 | CF$_3$CH$_2$ | PhCH$_2$ |
| A-853 | B-853 | ClCH$_2$CH$_2$ | PhCH$_2$ |
| A-854 | B-854 | ClCH$_2$CH$_2$CH$_2$ | PhCH$_2$ |
| A-855 | B-855 | CH$_3$OCH$_2$CH$_2$ | PhCH$_2$ |
| A-856 | B-856 | CH$_3$CH$_2$OCH$_2$CH$_2$ | PhCH$_2$ |
| A-857 | B-857 | CH$_3$OCH$_2$CH$_2$ | PhCH$_2$ |
| A-858 | B-858 | C$_2$H$_5$OCH$_2$CH$_2$ | PhCH$_2$ |
| A-859 | B-859 | n-C$_4$H$_9$OCH$_2$CH$_2$ | PhCH$_2$ |
| A-860 | B-860 | (CH$_3$O)$_2$CHCH$_2$ | PhCH$_2$ |
| A-861 | B-861 | | CH(CH$_3$)CH$_2$CH$_2$CH$_2$ |
| A-862 | B-862 | HOCH$_2$CH$_2$ | PhCH$_2$ |
| A-863 | B-863 | | CH$_2$CHBrCH$_2$CH$_2$ |
| A-864 | B-864 | | CH$_2$CH(OH)CH$_2$CH$_2$ |
| A-865 | B-865 | | CH$_2$CH=CHCH$_2$ |
| A-866 | B-866 | benzothiazol-2-yl | H |
| A-867 | B-867 | Ph | Ph |
| A-868 | B-868 | CH$_3$CONH | Ph |
| A-869 | B-869 | HOCH$_2$CH$_2$ | Ph |
| A-870 | B-870 | CH$_3$SO$_2$OCH$_2$CH$_2$CH$_2$ | H |
| A-871 | B-871 | | CH$_2$CH$_2$CH$_2$CH$_2$ |
| A-872 | B-872 | | CH$_2$CH$_2$CH$_2$CH$_2$CH$_2$ |
| A-873 | B-873 | | CH$_2$CH$_2$OCH$_2$CH$_2$ |
| A-874 | B-874 | | CH$_2$CH$_2$SCH$_2$CH$_2$ |
| A-875 | B-875 | | CH$_2$CH$_2$NHCH$_2$CH$_2$ |
| A-876 | B-876 | | CH$_2$CH$_2$N(CH$_3$)CH$_2$CH$_2$ |
| A-877 | B-877 | | N=CHCH$_2$CH$_2$ |
| A-878 | B-878 | Ph | NH$_2$ |
| A-879 | B-879 | PhCH$_2$ | (CH$_3$)$_2$C=N |
| A-880 | B-880 | Ph | (CH$_3$)$_2$C=N |
| A-881 | B-881 | PhCH$_2$ | H |

TABLE 2

Compounds of formula (I) in which $R^1$ is —C(=U)$NR^3R^4$; U is O, m is zero and $R^2$ is as defined hereafter. In Table 2 compounds C-1 to C-151 represent individual compounds in which $R^2$ is methyl; compounds D-1 to D-151 represent individual compounds in which $R^2$ is ethyl; compounds E-1 to E-151 represent individual compounds in which $R^2$ is allyl; compounds F-1 to F-151 represent individual compounds in which $R^2$ is propargyl; compounds G-1 to G-151 represent individual compounds in which $R^2$ is benzyl; compounds H-1 to H-151 represent individual compounds in which $R^2$ is —CH$_2$CO$_2$CH$_3$; compounds I-1 to I-151 represent individual compounds in which $R^2$ is —CH(CH$_3$)CO$_2$CH$_3$; compounds J-1 to J-151 represent individual compounds in which $R^2$ is —CH$_2$CH(OCH$_3$)$_2$.

| Compound | | | | | | | | $R^3$ | $R^4$ |
|---|---|---|---|---|---|---|---|---|---|
| C-1 | D-1 | E-1 | F-1 | G-1 | H-1 | I-1 | J-1 | CH2=CHCH2 | H |
| C-2 | D-2 | E-2 | F-2 | G-2 | H-2 | I-2 | J-2 | CH3CH=CHCH2 | H |
| C-3 | D-3 | E-3 | F-3 | G-3 | H-3 | I-3 | J-3 | CH2=CHCH2CH2 | H |

TABLE 2-continued

Compounds of formula (I) in which $R^1$ is —C(=U)NR$^3$R$^4$; U is O, m is zero and $R^2$ is as defined hereafter. In Table 2 compounds C-1 to C-151 represent individual compounds in which $R^2$ is methyl; compounds D-1 to D-151 represent individual compounds in which $R^2$ is ethyl; compounds E-1 to E-151 represent individual compounds in which $R^2$ is allyl; compounds F-1 to F-151 represent individual compounds in which $R^2$ is propargyl; compounds G-1 to G-151 represent individual compounds in which $R^2$ is benzyl; compounds H-1 to H-151 represent individual compounds in which $R^2$ is —CH$_2$CO$_2$CH$_3$; compounds I-1 to I-151 represent individual compounds in which $R^2$ is —CH(CH$_3$)CO$_2$CH$_3$; compounds J-1 to J-151 represent individual compounds in which $R^2$ is —CH$_2$CH(OCH$_3$)$_2$.

| Compound | | | | | | | | $R^3$ | $R^4$ |
|---|---|---|---|---|---|---|---|---|---|
| C-4 | D-4 | E-4 | F-4 | G-4 | H-4 | I-4 | J-4 | CHCCH2 | H |
| C-5 | D-5 | E-5 | F-5 | G-5 | H-5 | I-5 | J-5 | CH3CCCH2 | H |
| C-6 | D-6 | E-6 | F-6 | G-6 | H-6 | I-6 | J-6 | CHCCH(CH3) | H |
| C-7 | D-7 | E-7 | F-7 | G-7 | H-7 | I-7 | J-7 | cyclo-C3H5 | H |
| C-8 | D-8 | E-8 | F-8 | G-8 | H-8 | I-8 | J-8 | cyclo-C5H9 | H |
| C-9 | D-9 | E-9 | F-9 | G-9 | H-9 | I-9 | J-9 | cyclo-C6H11 | H |
| C-10 | D-10 | E-10 | F-10 | G-10 | H-10 | I-10 | J-10 | PhCH2 | H |
| C-11 | D-11 | E-11 | F-11 | G-11 | H-11 | I-11 | J-11 | PhCH(CH3) | H |
| C-12 | D-12 | E-12 | F-12 | G-12 | H-12 | I-12 | J-12 | NH2 | H |
| C-13 | D-13 | E-13 | F-13 | G-13 | H-13 | I-13 | J-13 | CH3NH | H |
| C-14 | D-14 | E-14 | F-14 | G-14 | H-14 | I-14 | J-14 | C2H5NH | H |
| C-15 | D-15 | E-15 | F-15 | G-15 | H-15 | I-15 | J-15 | n-C3H7NH | H |
| C-16 | D-16 | E-16 | F-16 | G-16 | H-16 | I-16 | J-16 | iso-C3H7NH | H |
| C-17 | D-17 | E-17 | F-17 | G-17 | H-17 | I-17 | J-17 | n-C4H9NH | H |
| C-18 | D-18 | E-18 | F-18 | G-18 | H-18 | I-18 | J-18 | tert-C4H9NH | H |
| C-19 | D-19 | E-19 | F-19 | G-19 | H-19 | I-19 | J-19 | n-C5H11NH | H |
| C-20 | D-20 | E-20 | F-20 | G-20 | H-20 | I-20 | J-20 | n-C6H13NH | H |
| C-21 | D-21 | E-21 | F-21 | G-21 | H-21 | I-21 | J-21 | PhCH2NH | H |
| C-22 | D-22 | E-22 | F-22 | G-22 | H-22 | I-22 | J-22 | PhNH | H |
| C-23 | D-23 | E-23 | F-23 | G-23 | H-23 | I-23 | J-23 | HO | H |
| C-24 | D-24 | E-24 | F-24 | G-24 | H-24 | I-24 | J-24 | CH3O | H |
| C-25 | D-25 | E-25 | F-25 | G-25 | H-25 | I-25 | J-25 | C2H5O | H |
| C-26 | D-26 | E-26 | F-26 | G-26 | H-26 | I-26 | J-26 | n-C3H7O | H |
| C-27 | D-27 | E-27 | F-27 | G-27 | H-27 | I-27 | J-27 | iso-C3H7O | H |
| C-28 | D-28 | E-28 | F-28 | G-28 | H-28 | I-28 | J-28 | n-C4H9O | H |
| C-29 | D-29 | E-29 | F-29 | G-29 | H-29 | I-29 | J-29 | tert-C4H9O | H |
| C-30 | D-30 | E-30 | F-30 | G-30 | H-30 | I-30 | J-30 | CH2=CHCH2O | H |
| C-31 | D-31 | E-31 | F-31 | G-31 | H-31 | I-31 | J-31 | CHCCH2O | H |
| C-32 | D-32 | E-32 | F-32 | G-32 | H-32 | I-32 | J-32 | CH3O2CCH2O | H |
| C-33 | D-33 | E-33 | F-33 | G-33 | H-33 | I-33 | J-33 | CH3O2CCH(CH3)O | H |
| C-34 | D-34 | E-34 | F-34 | G-34 | H-34 | I-34 | J-34 | CH3O2CC(CH3)2O | H |
| C-35 | D-35 | E-35 | F-35 | G-35 | H-35 | I-35 | J-35 | PhCH2O | H |
| C-36 | D-36 | E-36 | F-36 | G-36 | H-36 | I-36 | J-36 | Ph | H |
| C-37 | D-37 | E-37 | F-37 | G-37 | H-37 | I-37 | J-37 | 2-F—Ph | H |
| C-38 | D-38 | E-38 | F-38 | G-38 | H-38 | I-38 | J-38 | 3-F—Ph | H |
| C-39 | D-39 | E-39 | F-39 | G-39 | H-39 | I-39 | J-39 | 4-F—Ph | H |
| C-40 | D-40 | E-40 | F-40 | G-40 | H-40 | I-40 | J-40 | 2-Cl—Ph | H |
| C-41 | D-41 | E-41 | F-41 | G-41 | H-41 | I-41 | J-41 | 3-Cl—Ph | H |
| C-42 | D-42 | E-42 | F-42 | G-42 | H-42 | I-42 | J-42 | 4-Cl—Ph | H |
| C-43 | D-43 | E-43 | F-43 | G-43 | H-43 | I-43 | J-43 | 2-CF3—Ph | H |
| C-44 | D-44 | E-44 | F-44 | G-44 | H-44 | I-44 | J-44 | 3-CF3—Ph | H |
| C-45 | D-45 | E-45 | F-45 | G-45 | H-45 | I-45 | J-45 | 4-CF3—Ph | H |
| C-46 | D-46 | E-46 | F-46 | G-46 | H-46 | I-46 | J-46 | 2-CH3—Ph | H |
| C-47 | D-47 | E-47 | F-47 | G-47 | H-47 | I-47 | J-47 | 3-CH3—Ph | H |
| C-48 | D-48 | E-48 | F-48 | G-48 | H-48 | I-48 | J-48 | 4-CH3—Ph | H |
| C-49 | D-49 | E-49 | F-49 | G-49 | H-49 | I-49 | J-49 | 2-CH3O—Ph | H |
| C-50 | D-50 | E-50 | F-50 | G-50 | H-50 | I-50 | J-50 | 3-CH3O—Ph | H |
| C-51 | D-51 | E-51 | F-51 | G-51 | H-51 | I-51 | J-51 | 4-CH3O—Ph | H |
| C-52 | D-52 | E-52 | F-52 | G-52 | H-52 | I-52 | J-52 | 4-CF3O—Ph | H |
| C-53 | D-53 | E-53 | F-53 | G-53 | H-53 | I-53 | J-53 | 4-CF3CH2O—Ph | H |
| C-54 | D-54 | E-54 | F-54 | G-54 | H-54 | I-54 | J-54 | 4-PhO—Ph | H |
| C-55 | D-55 | E-55 | F-55 | G-55 | H-55 | I-55 | J-55 | 4-(4-Cl—PhO)-Ph | H |
| C-56 | D-56 | E-56 | F-56 | G-56 | H-56 | I-56 | J-56 | 4-(4-CF3—PhO)-Ph | H |
| C-57 | D-57 | E-57 | F-57 | G-57 | H-57 | I-57 | J-57 | CF3CH2 | H |
| C-58 | D-58 | E-58 | F-58 | G-58 | H-58 | I-58 | J-58 | ClCH2CH2 | H |
| C-59 | D-59 | E-59 | F-59 | G-59 | H-59 | I-59 | J-59 | ClCH2CH2CH2 | H |
| C-60 | D-60 | E-60 | F-60 | G-60 | H-60 | I-60 | J-60 | CH3OCH2CH2 | H |
| C-61 | D-61 | E-61 | F-61 | G-61 | H-61 | I-61 | J-61 | CH3CH2OCH2CH2 | H |
| C-62 | D-62 | E-62 | F-62 | G-62 | H-62 | I-62 | J-62 | CH3OCH2CH2CH2 | H |
| C-63 | D-63 | E-63 | F-63 | G-63 | H-63 | I-63 | J-63 | C2H5OCH2CH2CH2 | H |
| C-64 | D-64 | E-64 | F-64 | G-64 | H-64 | I-64 | J-64 | n-C4H9OCH2CH2CH2 | H |
| C-65 | D-65 | E-65 | F-65 | G-65 | H-65 | I-65 | J-65 | CH3OCH(CH3)CH2CH2 | H |
| C-66 | D-66 | E-66 | F-66 | G-66 | H-66 | I-66 | J-66 | (CH3O)2CHCH2 | H |
| C-67 | D-67 | E-67 | F-67 | G-67 | H-67 | I-67 | J-67 | HOCH2CH2 | H |
| C-68 | D-68 | E-68 | F-68 | G-68 | H-68 | I-68 | J-68 | HOCH2CH2CH2 | H |
| C-69 | D-69 | E-69 | F-69 | G-69 | H-69 | I-69 | J-69 | CH3SCH2CH2 | H |

TABLE 2-continued

Compounds of formula (I) in which $R^1$ is —C(=U)NR$^3$R$^4$; U is O, m is zero and $R^2$ is as defined hereafter. In Table 2 compounds C-1 to C-151 represent individual compounds in which $R^2$ is methyl; compounds D-1 to D-151 represent individual compounds in which $R^2$ is ethyl; compounds E-1 to E-151 represent individual compounds in which $R^2$ is allyl; compounds F-1 to F-151 represent individual compounds in which $R^2$ is propargyl; compounds G-1 to G-151 represent individual compounds in which $R^2$ is benzyl; compounds H-1 to H-151 represent individual compounds in which $R^2$ is —CH$_2$CO$_2$CH$_3$; compounds I-1 to I-151 represent individual compounds in which $R^2$ is —CH(CH$_3$)CO$_2$CH$_3$; compounds J-1 to J-151 represent individual compounds in which $R^2$ is —CH$_2$CH(OCH$_3$)$_2$.

| Compound | | | | | | | | $R^3$ | $R^4$ |
|---|---|---|---|---|---|---|---|---|---|
| C-70 | D-70 | E-70 | F-70 | G-70 | H-70 | I-70 | J-70 | CH3CH2SCH2CH2 | H |
| C-71 | D-71 | E-71 | F-71 | G-71 | H-71 | I-71 | J-71 | CH3SCH2CH2CH2 | H |
| C-72 | D-72 | E-72 | F-72 | G-72 | H-72 | I-72 | J-72 | C2H5SCH2CH2CH2 | H |
| C-73 | D-73 | E-73 | F-73 | G-73 | H-73 | I-73 | J-73 | CH2=CHCH2 | CH3 |
| C-74 | D-74 | E-74 | F-74 | G-74 | H-74 | I-74 | J-74 | CHCCH2 | CH3 |
| C-75 | D-75 | E-75 | F-75 | G-75 | H-75 | I-75 | J-75 | cyclo-C3H5 | CH3 |
| C-76 | D-76 | E-76 | F-76 | G-76 | H-76 | I-76 | J-76 | cyclo-C5H9 | CH3 |
| C-77 | D-77 | E-77 | F-77 | G-77 | H-77 | I-77 | J-77 | cyclo-C6H11 | CH3 |
| C-78 | D-78 | E-78 | F-78 | G-78 | H-78 | I-78 | J-78 | PhCH2 | CH3 |
| C-79 | D-79 | E-79 | F-79 | G-79 | H-79 | I-79 | J-79 | NH2 | CH3 |
| C-80 | D-80 | E-80 | F-80 | G-80 | H-80 | I-80 | J-80 | CH3NH | CH3 |
| C-81 | D-81 | E-81 | F-81 | G-81 | H-81 | I-81 | J-81 | C2H5NH | CH3 |
| C-82 | D-82 | E-82 | F-82 | G-82 | H-82 | I-82 | J-82 | PhCH2NH | CH3 |
| C-83 | D-83 | E-83 | F-83 | G-83 | H-83 | I-83 | J-83 | PhNH | CH3 |
| C-84 | D-84 | E-84 | F-84 | G-84 | H-84 | I-84 | J-84 | HO | CH3 |
| C-85 | D-85 | E-85 | F-85 | G-85 | H-85 | I-85 | J-85 | CH3O | CH3 |
| C-86 | D-86 | E-86 | F-86 | G-86 | H-86 | I-86 | J-86 | C2H5O | CH3 |
| C-87 | D-87 | E-87 | F-87 | G-87 | H-87 | I-87 | J-87 | CH2=CHCH2O | CH3 |
| C-88 | D-88 | E-88 | F-88 | G-88 | H-88 | I-88 | J-88 | CHCCH2O | CH3 |
| C-89 | D-89 | E-89 | F-89 | G-89 | H-89 | I-89 | J-89 | CH3O2CCH2O | CH3 |
| C-90 | D-90 | E-90 | F-90 | G-90 | H-90 | I-90 | J-90 | CH3O2CCH(CH3)O | CH3 |
| C-91 | D-91 | E-91 | F-91 | G-91 | H-91 | I-91 | J-91 | PhCH2O | CH3 |
| C-92 | D-92 | E-92 | F-92 | G-92 | H-92 | I-92 | J-92 | Ph | CH3 |
| C-93 | D-93 | E-93 | F-93 | G-93 | H-93 | I-93 | J-93 | 4-CF3O—Ph | CH3 |
| C-94 | D-94 | E-94 | F-94 | G-94 | H-94 | I-94 | J-94 | 4-(4-CF3O)-Ph | CH3 |
| C-95 | D-95 | E-95 | F-95 | G-95 | H-95 | I-95 | J-95 | CF3CH2 | CH3 |
| C-96 | D-96 | E-96 | F-96 | G-96 | H-96 | I-96 | J-96 | CH3OCH2CH2 | CH3 |
| C-97 | D-97 | E-97 | F-97 | G-97 | H-97 | I-97 | J-97 | CH3CH2OCH2CH2 | CH3 |
| C-98 | D-98 | E-98 | F-98 | G-98 | H-98 | I-98 | J-98 | CH3OCH2CH2CH2 | CH3 |
| C-99 | D-99 | E-99 | F-99 | G-99 | H-99 | I-99 | J-99 | C2H5OCH2CH2CH2 | CH3 |
| C-100 | D-100 | E-100 | F-100 | G-100 | H-100 | I-100 | J-100 | n-C4H9OCH2CH2CH2 | CH3 |
| C-101 | D-101 | E-101 | F-101 | G-101 | H-101 | I-101 | J-101 | (CH3O)2CHCH2 | CH3 |
| C-102 | D-102 | E-102 | F-102 | G-102 | H-102 | I-102 | J-102 | HOCH2CH2 | CH3 |
| C-103 | D-103 | E-103 | F-103 | G-103 | H-103 | I-103 | J-103 | HOCH2CH2CH2 | CH3 |
| C-104 | D-104 | E-104 | F-104 | G-104 | H-104 | I-104 | J-104 | CH3OCH2CH2CH2 | CH3 |
| C-105 | D-105 | E-105 | F-105 | G-105 | H-105 | I-105 | J-105 | C2H5OCH2CH2CH2 | CH3 |
| C-106 | D-106 | E-106 | F-106 | G-106 | H-106 | I-106 | J-106 | n-C4H9OCH2CH2CH2 | CH3 |
| C-107 | D-107 | E-107 | F-107 | G-107 | H-107 | I-107 | J-107 | (CH3O)2CHCH2 | CH3 |
| C-108 | D-108 | E-108 | F-108 | G-108 | H-108 | I-108 | J-108 | HOCH2CH2 | CH3 |
| C-109 | D-109 | E-109 | F-109 | G-109 | H-109 | I-109 | J-109 | HOCH2CH2 | CH3 |
| C-110 | D-110 | E-110 | F-110 | G-110 | H-110 | I-110 | J-110 | CH2=CHCH2 | PhCH2 |
| C-111 | D-111 | E-111 | F-111 | G-111 | H-111 | I-111 | J-111 | CHCCH2 | PhCH2 |
| C-112 | D-112 | E-112 | F-112 | G-112 | H-112 | I-112 | J-112 | cyclo-C3H5 | PhCH2 |
| C-113 | D-113 | E-113 | F-113 | G-113 | H-113 | I-113 | J-113 | cyclo-C5H9 | PhCH2 |
| C-114 | D-114 | E-114 | F-114 | G-114 | H-114 | I-114 | J-114 | cyclo-C6H11 | PhCH2 |
| C-115 | D-115 | E-115 | F-115 | G-115 | H-115 | I-115 | J-115 | NH2 | PhCH2 |
| C-116 | D-116 | E-116 | F-116 | G-116 | H-116 | I-116 | J-116 | CH3NH | PhCH2 |
| C-117 | D-117 | E-117 | F-117 | G-117 | H-117 | I-117 | J-117 | C2H5NH | PhCH2 |
| C-118 | D-118 | E-118 | F-118 | G-118 | H-118 | I-118 | J-118 | PhNH | PhCH2 |
| C-119 | D-119 | E-119 | F-119 | G-119 | H-119 | I-119 | J-119 | HO | PhCH2 |
| C-120 | D-120 | E-120 | F-120 | G-120 | H-120 | I-120 | J-120 | CH3O | PhCH2 |
| C-121 | D-121 | E-121 | F-121 | G-121 | H-121 | I-121 | J-121 | C2H5O | PhCH2 |
| C-122 | D-122 | E-122 | F-122 | G-122 | H-122 | I-122 | J-122 | CH2=CHCH2O | PhCH2 |
| C-123 | D-123 | E-123 | F-123 | G-123 | H-123 | I-123 | J-123 | CHCCH2O | PhCH2 |
| C-124 | D-124 | E-124 | F-124 | G-124 | H-124 | I-124 | J-124 | CH3O2CCH2O | PhCH2 |
| C-125 | D-125 | E-125 | F-125 | G-125 | H-125 | I-125 | J-125 | CH3O2CCH(CH3)O | PhCH2 |
| C-126 | D-126 | E-126 | F-126 | G-126 | H-126 | I-126 | J-126 | PhCH2O | PhCH2 |
| C-127 | D-127 | E-127 | F-127 | G-127 | H-127 | I-127 | J-127 | Ph | PhCH2 |
| C-128 | D-128 | E-128 | F-128 | G-128 | H-128 | I-128 | J-128 | 4-CF3O—Ph | PhCH2 |
| C-129 | D-129 | E-129 | F-129 | G-129 | H-129 | I-129 | J-129 | 4-(4-CF3O)-Ph | PhCH2 |
| C-130 | D-130 | E-130 | F-130 | G-130 | H-130 | I-130 | J-130 | CF3CH2 | PhCH2 |
| C-131 | D-131 | E-131 | F-131 | G-131 | H-131 | I-131 | J-131 | CH3OCH2CH2 | PhCH2 |
| C-132 | D-132 | E-132 | F-132 | G-132 | H-132 | I-132 | J-132 | CH3CH2OCH2CH2 | PhCH2 |
| C-133 | D-133 | E-133 | F-133 | G-133 | H-133 | I-133 | J-133 | CH3OCH2CH2CH2 | PhCH2 |
| C-134 | D-134 | E-134 | F-134 | G-134 | H-134 | I-134 | J-134 | C2H5OCH2CH2CH2 | PhCH2 |
| C-135 | D-135 | E-135 | F-135 | G-135 | H-135 | I-135 | J-135 | n-C4H9OCH2CH2CH2 | PhCH2 |

TABLE 2-continued

Compounds of formula (I) in which $R^1$ is —C(=U)NR$^3$R$^4$; U is O, m is zero and $R^2$ is as defined hereafter. In Table 2 compounds C-1 to C-151 represent individual compounds in which $R^2$ is methyl; compounds D-1 to D-151 represent individual compounds in which $R^2$ is ethyl; compounds E-1 to E-151 represent individual compounds in which $R^2$ is allyl; compounds F-1 to F-151 represent individual compounds in which $R^2$ is propargyl; compounds G-1 to G-151 represent individual compounds in which $R^2$ is benzyl; compounds H-1 to H-151 represent individual compounds in which $R^2$ is —CH$_2$CO$_2$CH$_3$; compounds I-1 to I-151 represent individual compounds in which $R^2$ is —CH(CH$_3$)CO$_2$CH$_3$; compounds J-1 to J-151 represent individual compounds in which $R^2$ is —CH$_2$CH(OCH$_3$)$_2$.

| Compound | | | | | | | | R$^3$ | R$^4$ |
|---|---|---|---|---|---|---|---|---|---|
| C-136 | D-136 | E-136 | F-136 | G-136 | H-136 | I-136 | J-136 | (CH3O)2CHCH2 | PhCH2 |
| C-137 | D-137 | E-137 | F-137 | G-137 | H-137 | I-137 | J-137 | HOCH2CH2 | PhCH2 |
| C-138 | D-138 | E-138 | F-138 | G-138 | H-138 | I-138 | J-138 | HOCH2CH2CH2 | PhCH2 |
| C-139 | D-139 | E-139 | F-139 | G-139 | H-139 | I-139 | J-139 | CH3OCH2CH2CH2 | PhCH2 |
| C-140 | D-140 | E-140 | F-140 | G-140 | H-140 | I-140 | J-140 | C2H5OCH2CH2CH2 | PhCH2 |
| C-141 | D-141 | E-141 | F-141 | G-141 | H-141 | I-141 | J-141 | n-C4H9OCH2CH2CH2 | PhCH2 |
| C-142 | D-142 | E-142 | F-142 | G-142 | H-142 | I-142 | J-142 | (CH3O)2CHCH2 | PhCH2 |
| C-143 | D-143 | E-143 | F-143 | G-143 | H-143 | I-143 | J-143 | HOCH2CH2 | PhCH2 |
| C-144 | D-144 | E-144 | F-144 | G-144 | H-144 | I-144 | J-144 | HOCH2CH2CH2 | PhCH2 |
| C-145 | D-145 | E-145 | F-145 | G-145 | H-145 | I-145 | J-145 | CH2CH2CH2CH2 | |
| C-146 | D-146 | E-146 | F-146 | G-146 | H-146 | I-146 | J-146 | CH2CH2CH2CH2CH2 | |
| C-147 | D-147 | E-147 | F-147 | G-147 | H-147 | I-147 | J-147 | CH2CH2OCH2CH2 | |
| C-148 | D-148 | E-148 | F-148 | G-148 | H-148 | I-148 | J-148 | CH2CH2SCH2CH2 | |
| C-149 | D-149 | E-149 | F-149 | G-149 | H-149 | I-149 | J-149 | CH2CH2NHCH2CH2 | |
| C-150 | D-150 | E-150 | F-150 | G-150 | H-150 | I-150 | J-150 | CH2CH2N(CH3)CH2CH2 | |
| C-151 | D-151 | E-151 | F-151 | G-151 | H-151 | I-151 | J-151 | N=CHCH2CH2 | |

TABLE 3

Compounds of formula (I) in which $R^1$ is —C(=U)NR$^3$R$^4$; U is S and m is zero. In Table 3 compounds K-1 to K-151 represent individual compounds in which $R^2$ is methyl; compounds L-1 to L-151 represent individual compounds in which $R^2$ is ethyl; compounds M-1 to M-151 represent individual compounds in which $R^2$ is allyl; compounds N-1 to N-151 represent individual compounds in which $R^2$ is propargyl; compounds O-1 to O-151 represent individual compounds in which $R^2$ is benzyl; compounds P-1 to P-151 represent individual compounds in which $R^2$ is —CH$_2$CO$_2$CH$_3$; compounds Q-1 to Q-151 represent individual compounds in which $R^2$ is —CH(CH$_3$)CO$_2$CH$_3$; compounds R-1 to R-151 represent individual compounds in which $R^2$ is —CH$_2$CH(OCH$_3$)$_2$.

| Compound | | | | | | | | R$^3$ | R$^4$ |
|---|---|---|---|---|---|---|---|---|---|
| K-1 | L-1 | M-1 | N-1 | O-1 | P-1 | Q-1 | R-1 | CH2=CHCH2 | H |
| K-2 | L-2 | M-2 | N-2 | O-2 | P-2 | Q-2 | R-2 | CH3CH=CHCH2 | H |
| K-3 | L-3 | M-3 | N-3 | O-3 | P-3 | Q-3 | R-3 | CH2=CHCH2CH2 | H |
| K-4 | L-4 | M-4 | N-4 | O-4 | P-4 | Q-4 | R-4 | CHCCH2 | H |
| K-5 | L-5 | M-5 | N-5 | O-5 | P-5 | Q-1 | R-5 | CH3CCCH2 | H |
| K-6 | L-6 | M-6 | N-6 | O-6 | P-6 | Q-2 | R-6 | CHCCH(CH3) | H |
| K-7 | L-7 | M-7 | N-7 | O-7 | P-7 | Q-3 | R-7 | cyclo-C3H5 | H |
| K-8 | L-8 | M-8 | N-8 | O-8 | P-8 | Q-4 | R-8 | cyclo-C5H9 | H |
| K-9 | L-9 | M-9 | N-9 | O-9 | P-9 | Q-1 | R-9 | cyclo-C6H11 | H |
| K-10 | L-10 | M-10 | N-10 | O-10 | P-10 | Q-2 | R-10 | PhCH2 | H |
| K-11 | L-11 | M-11 | N-11 | O-11 | P-11 | Q-3 | R-11 | PhCH(CH3) | H |
| K-12 | L-12 | M-12 | N-12 | O-12 | P-12 | Q-4 | R-12 | NH2 | H |
| K-13 | L-13 | M-13 | N-13 | O-13 | P-13 | Q-1 | R-13 | CH3NH | H |
| K-14 | L-14 | M-14 | N-14 | O-14 | P-14 | Q-2 | R-14 | C2H5NH | H |
| K-15 | L-15 | M-15 | N-15 | O-15 | P-15 | Q-3 | R-15 | n-C3H7NH | H |
| K-16 | L-16 | M-16 | N-16 | O-16 | P-16 | Q-4 | R-16 | iso-C3H7NH | H |
| K-17 | L-17 | M-17 | N-17 | O-17 | P-17 | Q-1 | R-17 | n-C4H9NH | H |
| K-18 | L-18 | M-18 | N-18 | O-18 | P-18 | Q-2 | R-18 | tert-C4H9NH | H |
| K-19 | L-19 | M-19 | N-19 | O-19 | P-19 | Q-3 | R-19 | n-C5H11NH | H |
| K-20 | L-20 | M-20 | N-20 | O-20 | P-20 | Q-4 | R-20 | n-C6H13NH | H |
| K-21 | L-21 | M-21 | N-21 | O-21 | P-21 | Q-1 | R-21 | PhCH2NH | H |
| K-22 | L-22 | M-22 | N-22 | O-22 | P-22 | Q-2 | R-22 | PhNH | H |
| K-23 | L-23 | M-23 | N-23 | O-23 | P-23 | Q-3 | R-23 | HO | H |
| K-24 | L-24 | M-24 | N-24 | O-24 | P-24 | Q-4 | R-24 | CH3O | H |
| K-25 | L-25 | M-25 | N-25 | O-25 | P-25 | Q-1 | R-25 | C2H5O | H |
| K-26 | L-26 | M-26 | N-26 | O-26 | P-26 | Q-2 | R-26 | n-C3H7O | H |
| K-27 | L-27 | M-27 | N-27 | O-27 | P-27 | Q-3 | R-27 | iso-C3H7O | H |
| K-28 | L-28 | M-28 | N-28 | O-28 | P-28 | Q-4 | R-28 | n-C4H9O | H |
| K-29 | L-29 | M-29 | N-29 | O-29 | P-29 | Q-1 | R-29 | tert-C4H9O | H |
| K-30 | L-30 | M-30 | N-30 | O-30 | P-30 | Q-2 | R-30 | CH2=CHCH2O | H |
| K-31 | L-31 | M-31 | N-31 | O-31 | P-31 | Q-3 | R-31 | CHCCH2O | H |

TABLE 3-continued

Compounds of formula (I) in which $R^1$ is —C(=U)NR$^3$R$^4$; U is S and m is zero. In Table 3 compounds K-1 to K-151 represent individual compounds in which $R^2$ is methyl; compounds L-1 to L-151 represent individual compounds in which $R^2$ is ethyl; compounds M-1 to M-151 represent individual compounds in which $R^2$ is allyl; compounds N-1 to N-151 represent individual compounds in which $R^2$ is propargyl; compounds O-1 to O-151 represent individual compounds in which $R^2$ is benzyl; compounds P-1 to P-151 represent individual compounds in which $R^2$ is —CH$_2$CO$_2$CH$_3$; compounds Q-1 to Q-151 represent individual compounds in which $R^2$ is —CH(CH$_3$)CO$_2$CH$_3$; compounds R-1 to R-151 represent individual compounds in which $R^2$ is —CH$_2$CH(OCH$_3$)$_2$.

| Compound | | | | | | | | R$^3$ | R$^4$ |
|---|---|---|---|---|---|---|---|---|---|
| K-32 | L-32 | M-32 | N-32 | O-32 | P-32 | Q-4 | R-32 | CH3O2CCH2O | H |
| K-33 | L-33 | M-33 | N-33 | O-33 | P-33 | Q-1 | R-33 | CH3O2CCH(CH3)O | H |
| K-34 | L-34 | M-34 | N-34 | O-34 | P-34 | Q-2 | R-34 | CH3O2CC(CH3)2O | H |
| K-35 | L-35 | M-35 | N-35 | O-35 | P-35 | Q-3 | R-35 | PhCH2O | H |
| K-36 | L-36 | M-36 | N-36 | O-36 | P-36 | Q-4 | R-36 | Ph | H |
| K-37 | L-37 | M-37 | N-37 | O-37 | P-37 | Q-1 | R-37 | 2-F—Ph | H |
| K-38 | L-38 | M-38 | N-38 | O-38 | P-38 | Q-2 | R-38 | 3-F—Ph | H |
| K-39 | L-39 | M-39 | N-39 | O-39 | P-39 | Q-3 | R-39 | 4-F—Ph | H |
| K-40 | L-40 | M-40 | N-40 | O-40 | P-40 | Q-4 | R-40 | 2-Cl—Ph | H |
| K-41 | L-41 | M-41 | N-41 | O-41 | P-41 | Q-1 | R-41 | 3-Cl—Ph | H |
| K-42 | L-42 | M-42 | N-42 | O-42 | P-42 | Q-2 | R-42 | 4-Cl—Ph | H |
| K-43 | L-43 | M-43 | N-43 | O-43 | P-43 | Q-3 | R-43 | 2-CF3—Ph | H |
| K-44 | L-44 | M-44 | N-44 | O-44 | P-44 | Q-4 | R-44 | 3-CF3—Ph | H |
| K-45 | L-45 | M-45 | N-45 | O-45 | P-45 | Q-1 | R-45 | 4-CF3—Ph | H |
| K-46 | L-46 | M-46 | N-46 | O-46 | P-46 | Q-2 | R-46 | 2-CH3—Ph | H |
| K-47 | L-47 | M-47 | N-47 | O-47 | P-47 | Q-3 | R-47 | 3-CH3—Ph | H |
| K-48 | L-48 | M-48 | N-48 | O-48 | P-48 | Q-4 | R-48 | 4-CH3—Ph | H |
| K-49 | L-49 | M-49 | N-49 | O-49 | P-49 | Q-1 | R-49 | 2-CH3O—Ph | H |
| K-50 | L-50 | M-50 | N-50 | O-50 | P-50 | Q-2 | R-50 | 3-CH3O—Ph | H |
| K-51 | L-51 | M-51 | N-51 | O-51 | P-51 | Q-3 | R-51 | 4-CH3O—Ph | H |
| K-52 | L-52 | M-52 | N-52 | O-52 | P-52 | Q-4 | R-52 | 4-CF3O—Ph | H |
| K-53 | L-53 | M-53 | N-53 | O-53 | P-53 | Q-1 | R-53 | 4-CF3CH2O—Ph | H |
| K-54 | L-54 | M-54 | N-54 | O-54 | P-54 | Q-2 | R-54 | 4-PhO—Ph | H |
| K-55 | L-55 | M-55 | N-55 | O-55 | P-55 | Q-3 | R-55 | 4-(4-Cl—PhO)-Ph | H |
| K-56 | L-56 | M-56 | N-56 | O-56 | P-56 | Q-4 | R-56 | 4-(4-CF3—PhO)-Ph | H |
| K-57 | L-57 | M-57 | N-57 | O-57 | P-57 | Q-1 | R-57 | CF3CH2 | H |
| K-58 | L-58 | M-58 | N-58 | O-58 | P-58 | Q-2 | R-58 | ClCH2CH2 | H |
| K-59 | L-59 | M-59 | N-59 | O-59 | P-59 | Q-3 | R-59 | ClCH2CH2CH2 | H |
| K-60 | L-60 | M-60 | N-60 | O-60 | P-60 | Q-4 | R-60 | CH3OCH2CH2 | H |
| K-61 | L-61 | M-61 | N-61 | O-61 | P-61 | Q-1 | R-61 | CH3CH2OCH2CH2 | H |
| K-62 | L-62 | M-62 | N-62 | O-62 | P-62 | Q-2 | R-62 | CH3OCH2CH2CH2 | H |
| K-63 | L-63 | M-63 | N-63 | O-63 | P-63 | Q-3 | R-63 | C2H5OCH2CH2CH2 | H |
| K-64 | L-64 | M-64 | N-64 | O-64 | P-64 | Q-4 | R-64 | n-C4H9OCH2CH2CH2 | H |
| K-65 | L-65 | M-65 | N-65 | O-65 | P-65 | Q-1 | R-65 | CH3OCH(CH3)CH2CH2 | H |
| K-66 | L-66 | M-66 | N-66 | O-66 | P-66 | Q-2 | R-66 | (CH3O)2CHCH2 | H |
| K-67 | L-67 | M-67 | N-67 | O-67 | P-67 | Q-3 | R-67 | HOCH2CH2 | H |
| K-68 | L-68 | M-68 | N-68 | O-68 | P-68 | Q-4 | R-68 | HOCH2CH2CH2 | H |
| K-69 | L-69 | M-69 | N-69 | O-69 | P-69 | Q-1 | R-69 | CH3SCH2CH2 | H |
| K-70 | L-70 | M-70 | N-70 | O-70 | P-70 | Q-2 | R-70 | CH3CH2SCH2CH2 | H |
| K-71 | L-71 | M-71 | N-71 | O-71 | P-71 | Q-3 | R-71 | CH3SCH2CH2CH2 | H |
| K-72 | L-72 | M-72 | N-72 | O-72 | P-72 | Q-4 | R-72 | C2H5SCH2CH2CH2 | H |
| K-73 | L-73 | M-73 | N-73 | O-73 | P-73 | Q-1 | R-73 | CH2=CHCH2 | CH3 |
| K-74 | L-74 | M-74 | N-74 | O-74 | P-74 | Q-2 | R-74 | CHCCH2 | CH3 |
| K-75 | L-75 | M-75 | N-75 | O-75 | P-75 | Q-3 | R-75 | cyclo-C3H5 | CH3 |
| K-76 | L-76 | M-76 | N-76 | O-76 | P-76 | Q-4 | R-76 | cyclo-C5H9 | CH3 |
| K-77 | L-77 | M-77 | N-77 | O-77 | P-77 | Q-1 | R-77 | cyclo-C6H11 | CH3 |
| K-78 | L-78 | M-78 | N-78 | O-78 | P-78 | Q-2 | R-78 | PhCH2 | CH3 |
| K-79 | L-79 | M-79 | N-79 | O-79 | P-79 | Q-3 | R-79 | NH2 | CH3 |
| K-80 | L-80 | M-80 | N-80 | O-80 | P-80 | Q-4 | R-80 | CH3NH | CH3 |
| K-81 | L-81 | M-81 | N-81 | O-81 | P-81 | Q-1 | R-81 | C2H5NH | CH3 |
| K-82 | L-82 | M-82 | N-82 | O-82 | P-82 | Q-2 | R-82 | PhCH2NH | CH3 |
| K-83 | L-83 | M-83 | N-83 | O-83 | P-83 | Q-3 | R-83 | PhNH | CH3 |
| K-84 | L-84 | M-84 | N-84 | O-84 | P-84 | Q-4 | R-84 | HO | CH3 |
| K-85 | L-85 | M-85 | N-85 | O-85 | P-85 | Q-1 | R-85 | CH3O | CH3 |
| K-86 | L-86 | M-86 | N-86 | O-86 | P-86 | Q-2 | R-86 | C2H5O | CH3 |
| K-87 | L-87 | M-87 | N-87 | O-87 | P-87 | Q-3 | R-87 | CH2=CHCH2O | CH3 |
| K-88 | L-88 | M-88 | N-88 | O-88 | P-88 | Q-4 | R-88 | CHCCH2O | CH3 |
| K-89 | L-89 | M-89 | N-89 | O-89 | P-89 | Q-1 | R-89 | CH3O2CCH2O | CH3 |
| K-90 | L-90 | M-90 | N-90 | O-90 | P-90 | Q-2 | R-90 | CH3O2CCH(CH3)O | CH3 |
| K-91 | L-91 | M-91 | N-91 | O-91 | P-91 | Q-3 | R-91 | PhCH2O | CH3 |
| K-92 | L-92 | M-92 | N-92 | O-92 | P-92 | Q-4 | R-92 | Ph | CH3 |
| K-93 | L-93 | M-93 | N-93 | O-93 | P-93 | Q-1 | R-93 | 4-CF3O—Ph | CH3 |
| K-94 | L-94 | M-94 | N-94 | O-94 | P-94 | Q-2 | R-94 | 4-(4-CF3O)-Ph | CH3 |
| K-95 | L-95 | M-95 | N-95 | O-95 | P-95 | Q-3 | R-95 | CF3CH2 | CH3 |
| K-96 | L-96 | M-96 | N-96 | O-96 | P-96 | Q-4 | R-96 | CH3OCH2CH2 | CH3 |
| K-97 | L-97 | M-97 | N-97 | O-97 | P-97 | Q-1 | R-97 | CH3CH2OCH2CH2 | CH3 |

TABLE 3-continued

Compounds of formula (I) in which $R^1$ is —C(=U)NR$^3$R$^4$; U is S and m is zero. In Table 3 compounds K-1 to K-151 represent individual compounds in which $R^2$ is methyl; compounds L-1 to L-151 represent individual compounds in which $R^2$ is ethyl; compounds M-1 to M-151 represent individual compounds in which $R^2$ is allyl; compounds N-1 to N-151 represent individual compounds in which $R^2$ is propargyl; compounds O-1 to O-151 represent individual compounds in which $R^2$ is benzyl; compounds P-1 to P-151 represent individual compounds in which $R^2$ is —CH$_2$CO$_2$CH$_3$; compounds Q-1 to Q-151 represent individual compounds in which $R^2$ is —CH(CH$_3$)CO$_2$CH$_3$; compounds R-1 to R-151 represent individual compounds in which $R^2$ is —CH$_2$CH(OCH$_3$)$_2$.

| Compound | | | | | | | | $R^3$ | $R^4$ |
|---|---|---|---|---|---|---|---|---|---|
| K-98 | L-98 | M-98 | N-98 | O-98 | P-98 | Q-2 | R-98 | CH3OCH2CH2CH2 | CH3 |
| K-99 | L-99 | M-99 | N-99 | O-99 | P-99 | Q-3 | R-99 | C2H5OCH2CH2CH2 | CH3 |
| K-100 | L-100 | M-100 | N-100 | O-100 | P-100 | Q-4 | R-100 | n-C4H9OCH2CH2CH2 | CH3 |
| K-101 | L-101 | M-101 | N-101 | O-101 | P-101 | Q-1 | R-101 | (CH3O)2CHCH2 | CH3 |
| K-102 | L-102 | M-102 | N-102 | O-102 | P-102 | Q-2 | R-102 | HOCH2CH2 | CH3 |
| K-103 | L-103 | M-103 | N-103 | O-103 | P-103 | Q-3 | R-103 | HOCH2CH2CH2 | CH3 |
| K-104 | L-104 | M-104 | N-104 | O-104 | P-104 | Q-4 | R-104 | CH3OCH2CH2CH2 | CH3 |
| K-105 | L-105 | M-105 | N-105 | O-105 | P-105 | Q-1 | R-105 | C2H5OCH2CH2CH2 | CH3 |
| K-106 | L-106 | M-106 | N-106 | O-106 | P-106 | Q-2 | R-106 | n-C4H9OCH2CH2CH2 | CH3 |
| K-107 | L-107 | M-107 | N-107 | O-107 | P-107 | Q-3 | R-107 | (CH3O)2CHCH2 | CH3 |
| K-108 | L-108 | M-108 | N-108 | O-108 | P-108 | Q-4 | R-108 | HOCH2CH2 | CH3 |
| K-109 | L-109 | M-109 | N-109 | O-109 | P-109 | Q-1 | R-109 | HOCH2CH2CH2 | CH3 |
| K-110 | L-110 | M-110 | N-110 | O-110 | P-110 | Q-2 | R-110 | CH2=CHCH2 | PhCH2 |
| K-111 | L-111 | M-111 | N-111 | O-111 | P-111 | Q-3 | R-111 | CHCCH2 | PhCH2 |
| K-112 | L-112 | M-112 | N-112 | O-112 | P-112 | Q-4 | R-112 | cyclo-C3H5 | PhCH2 |
| K-113 | L-113 | M-113 | N-113 | O-113 | P-113 | Q-1 | R-113 | cyclo-C5H9 | PhCH2 |
| K-114 | L-114 | M-114 | N-114 | O-114 | P-114 | Q-2 | R-114 | cyclo-C6H11 | PhCH2 |
| K-115 | L-115 | M-115 | N-115 | O-115 | P-115 | Q-3 | R-115 | NH2 | PhCH2 |
| K-116 | L-116 | M-116 | N-116 | O-116 | P-116 | Q-4 | R-116 | CH3NH | PhCH2 |
| K-117 | L-117 | M-117 | N-117 | O-117 | P-117 | Q-1 | R-117 | C2H5NH | PhCH2 |
| K-118 | L-118 | M-118 | N-118 | O-118 | P-118 | Q-2 | R-118 | PhNH | PhCH2 |
| K-119 | L-119 | M-119 | N-119 | O-119 | P-119 | Q-3 | R-119 | HO | PhCH2 |
| K-120 | L-120 | M-120 | N-120 | O-120 | P-120 | Q-4 | R-120 | CH3O | PhCH2 |
| K-121 | L-121 | M-121 | N-121 | O-121 | P-121 | Q-1 | R-121 | C2H5O | PhCH2 |
| K-122 | L-122 | M-122 | N-122 | O-122 | P-122 | Q-2 | R-122 | CH2=CHCH2O | PhCH2 |
| K-123 | L-123 | M-123 | N-123 | O-123 | P-123 | Q-3 | R-123 | CHCCH2O | PhCH2 |
| K-124 | L-124 | M-124 | N-124 | O-124 | P-124 | Q-4 | R-124 | CH3O2CCH2O | PhCH2 |
| K-125 | L-125 | M-125 | N-125 | O-125 | P-125 | Q-1 | R-125 | CH3O2CCH(CH3)O | PhCH2 |
| K-126 | L-126 | M-126 | N-126 | O-126 | P-126 | Q-2 | R-126 | PhCH2O | PhCH2 |
| K-127 | L-127 | M-127 | N-127 | O-127 | P-127 | Q-3 | R-127 | Ph | PhCH2 |
| K-128 | L-128 | M-128 | N-128 | O-128 | P-128 | Q-4 | R-128 | 4-CF3O—Ph | PhCH2 |
| K-129 | L-129 | M-129 | N-129 | O-129 | P-129 | Q-1 | R-129 | 4-(4-CF3O)-Ph | PhCH2 |
| K-130 | L-130 | M-130 | N-130 | O-130 | P-130 | Q-2 | R-130 | CF3CH2 | PhCH2 |
| K-131 | L-131 | M-131 | N-131 | O-131 | P-131 | Q-3 | R-131 | CH3OCH2CH2 | PhCH2 |
| K-132 | L-132 | M-132 | N-132 | O-132 | P-132 | Q-4 | R-132 | CH3CH2OCH2CH2 | PhCH2 |
| K-133 | L-133 | M-133 | N-133 | O-133 | P-133 | Q-1 | R-133 | CH3OCH2CH2CH2 | PhCH2 |
| K-134 | L-134 | M-134 | N-134 | O-134 | P-134 | Q-2 | R-134 | C2H5OCH2CH2CH2 | PhCH2 |
| K-135 | L-135 | M-135 | N-135 | O-135 | P-135 | Q-3 | R-135 | n-C4H9OCH2CH2CH2 | PhCH2 |
| K-136 | L-136 | M-136 | N-136 | O-136 | P-136 | Q-4 | R-136 | (CH3O)2CHCH2 | PhCH2 |
| K-137 | L-137 | M-137 | N-137 | O-137 | P-137 | Q-1 | R-137 | HOCH2CH2 | PhCH2 |
| K-138 | L-138 | M-138 | N-138 | O-138 | P-138 | Q-2 | R-138 | HOCH2CH2CH2 | PhCH2 |
| K-139 | L-139 | M-139 | N-139 | O-139 | P-139 | Q-3 | R-139 | CH3OCH2CH2CH2 | PhCH2 |
| K-140 | L-140 | M-140 | N-140 | O-140 | P-140 | Q-4 | R-140 | C2H5OCH2CH2CH2 | PhCH2 |
| K-141 | L-141 | M-141 | N-141 | O-141 | P-141 | Q-1 | R-141 | n-C4H9OCH2CH2CH2 | PhCH2 |
| K-142 | L-142 | M-142 | N-142 | O-142 | P-142 | Q-2 | R-142 | (CH3O)2CHCH2 | PhCH2 |
| K-143 | L-143 | M-143 | N-143 | O-143 | P-143 | Q-3 | R-143 | HOCH2CH2 | PhCH2 |
| K-144 | L-144 | M-144 | N-144 | O-144 | P-144 | Q-4 | R-144 | HOCH2CH2CH2 | PhCH2 |
| K-145 | L-145 | M-145 | N-145 | O-145 | P-145 | Q-1 | R-145 | CH2CH2CH2CH2 | |
| K-146 | L-146 | M-146 | N-146 | O-146 | P-146 | Q-2 | R-146 | CH2CH2CH2CH2CH2 | |
| K-147 | L-147 | M-147 | N-147 | O-147 | P-147 | Q-3 | R-147 | CH2CH2OCH2CH2 | |
| K-148 | L-148 | M-148 | N-148 | O-148 | P-148 | Q-4 | R-148 | CH2CH2SCH2CH2 | |
| K-149 | L-149 | M-149 | N-149 | O-149 | P-149 | Q-1 | R-149 | CH2CH2NHCH2CH2 | |
| K-150 | L-150 | M-150 | N-150 | O-150 | P-150 | Q-2 | R-150 | CH2CH2N(CH3)CH2CH2 | |
| K-151 | L-151 | M-151 | N-151 | O-151 | P-151 | Q-3 | R-151 | N=CHCH2CH2 | |

TABLE 4

Compounds of formula (IA):

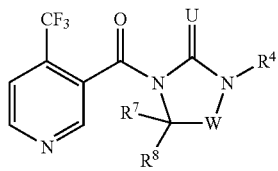

(IA)

| Compound | U | R⁷ | R⁸ | W | R⁴ |
|---|---|---|---|---|---|
| S-1 | O | H | H | CH2 | H |
| S-2 | O | H | H | CH2 | n-C3H7 |
| S-3 | O | H | H | CH2 | iso-C3H7 |
| S-4 | O | H | H | CH2 | n-C4H9 |
| S-5 | O | H | H | CH2 | iso-C4H9 |
| S-6 | O | H | H | CH2 | sec-C4H9 |
| S-7 | O | H | H | CH2 | tert-C4H9 |
| S-8 | O | H | H | CH2 | n-C5H11 |
| S-9 | O | H | H | CH2 | n-C6H13 |
| S-10 | O | H | H | CH2 | cyclo-C3H5 |
| S-11 | O | H | H | CH2 | cyclo-C5H9 |
| S-12 | O | H | H | CH2 | cyclo-C6H11 |
| S-13 | O | H | H | CH2 | CH2=CHCH2 |
| S-14 | O | H | H | CH2 | CHCCH2 |
| S-15 | O | H | H | CH2 | PhCH2 |
| S-16 | O | H | H | CH2 | Ph(CH3)CH |
| S-17 | O | H | H | CH2 | Ph(CH3)2C |
| S-18 | O | H | H | CH2 | Ph |
| S-19 | O | H | H | CH2 | 2-Cl—Ph |
| S-20 | O | H | H | CH2 | 3-Cl—Ph |
| S-21 | O | H | H | CH2 | 4-Cl—Ph |
| S-22 | O | H | H | CH2 | 4-CF3O—Ph |
| S-23 | O | H | H | CH2 | 4-(4-CF3—PhO)—Ph |
| S-24 | O | CH3 | H | CH2 | C2H5 |
| S-25 | O | CH3 | H | CH2 | n-C3H7 |
| S-26 | O | CH3 | H | CH2 | iso-C3H7 |
| S-27 | O | CH3 | H | CH2 | n-C4H9 |
| S-28 | O | CH3 | H | CH2 | iso-C4H9 |
| S-29 | O | CH3 | H | CH2 | sec-C4H9 |
| S-30 | O | CH3 | H | CH2 | tert-C4H9 |
| S-31 | O | CH3 | H | CH2 | n-C5H11 |
| S-32 | O | CH3 | H | CH2 | n-C6H13 |
| S-33 | O | CH3 | H | CH2 | cyclo-C3H5 |
| S-34 | O | CH3 | H | CH2 | cyclo-C5H9 |
| S-35 | O | CH3 | H | CH2 | cyclo-C6H11 |
| S-36 | O | CH3 | H | CH2 | CH2=CHCH2 |
| S-37 | O | CH3 | H | CH2 | CHCCH2 |
| S-38 | O | CH3 | H | CH2 | PhCH2 |
| S-39 | O | CH3 | H | CH2 | Ph(CH3)CH |
| S-40 | O | CH3 | H | CH2 | Ph(CH3)2C |
| S-41 | O | CH3 | H | CH2 | Ph |
| S-42 | O | CH3 | H | CH2 | 2-Cl—Ph |
| S-43 | O | CH3 | H | CH2 | 3-Cl—Ph |
| S-44 | O | CH3 | H | CH2 | 4-Cl—Ph |
| S-45 | O | CH3 | H | CH2 | 4-CF3O—Ph |
| S-46 | O | CH3 | H | CH2 | 4-(4-CF3—PhO)—Ph |
| S-47 | O | CH3 | CH3 | CH2 | CH3 |
| S-48 | O | CH3 | CH3 | CH2 | C2H5 |
| S-49 | O | CH3 | CH3 | CH2 | n-C3H7 |
| S-50 | O | CH3 | CH3 | CH2 | iso-C3H7 |
| S-51 | O | CH3 | CH3 | CH2 | n-C4H9 |
| S-52 | O | CH3 | CH3 | CH2 | iso-C4H9 |
| S-53 | O | CH3 | CH3 | CH2 | sec-C4H9 |
| S-54 | O | CH3 | CH3 | CH2 | tert-C4H9 |
| S-55 | O | CH3 | CH3 | CH2 | n-C5H11 |
| S-56 | O | CH3 | CH3 | CH2 | n-C6H13 |
| S-57 | O | CH3 | CH3 | CH2 | cyclo-C3H5 |
| S-58 | O | CH3 | CH3 | CH2 | cyclo-C5H9 |
| S-59 | O | CH3 | CH3 | CH2 | cyclo-C6H11 |
| S-60 | O | CH3 | CH3 | CH2 | CH2=CHCH2 |
| S-61 | O | CH3 | CH3 | CH2 | CHCCH2 |
| S-62 | O | CH3 | CH3 | CH2 | PhCH2 |
| S-63 | O | CH3 | CH3 | CH2 | Ph(CH3)CH |
| S-64 | O | CH3 | CH3 | CH2 | Ph(CH3)2C |
| S-65 | O | CH3 | CH3 | CH2 | Ph |
| S-66 | O | CH3 | CH3 | CH2 | 2-Cl—Ph |
| S-67 | O | CH3 | CH3 | CH2 | 3-Cl—Ph |
| S-68 | O | CH3 | CH3 | CH2 | 4-Cl—Ph |
| S-69 | O | CH3 | CH3 | CH2 | 4-CF3O—Ph |
| S-70 | O | CH3 | CH3 | CH2 | 4-(4-CF3—PhO)—Ph |
| S-71 | O | OCH3 | H | CH2 | C2H5 |
| S-72 | O | OCH3 | H | CH2 | n-C3H7 |
| S-73 | O | OCH3 | H | CH2 | iso-C3H7 |
| S-74 | O | OCH3 | H | CH2 | n-C4H9 |
| S-75 | O | OCH3 | H | CH2 | iso-C4H9 |
| S-76 | O | OCH3 | H | CH2 | sec-C4H9 |
| S-77 | O | OCH3 | H | CH2 | tert-C4H9 |
| S-78 | O | OCH3 | H | CH2 | n-C5H11 |
| S-79 | O | OCH3 | H | CH2 | n-C6H13 |
| S-80 | O | OCH3 | H | CH2 | cyclo-C3H5 |
| S-81 | O | OCH3 | H | CH2 | cyclo-C5H9 |
| S-82 | O | OCH3 | H | CH2 | cyclo-C6H11 |
| S-83 | O | OCH3 | H | CH2 | CH2=CHCH2 |
| S-84 | O | OCH3 | H | CH2 | CHCCH2 |
| S-85 | O | OCH3 | H | CH2 | PhCH2 |
| S-86 | O | OCH3 | H | CH2 | Ph(CH3)CH |
| S-87 | O | OCH3 | H | CH2 | Ph(CH3)2C |
| S-88 | O | OCH3 | H | CH2 | Ph |
| S-89 | O | OCH3 | H | CH2 | 2-Cl—Ph |
| S-90 | O | OCH3 | H | CH2 | 3-Cl—Ph |
| S-91 | O | OCH3 | H | CH2 | 4-Cl—Ph |
| S-92 | O | OCH3 | H | CH2 | 4-CF3O—Ph |
| S-93 | O | OCH3 | H | CH2 | 4-(4-CF3—PhO)—Ph |
| S-94 | O | OCH2CH3 | H | CH2 | CH3 |
| S-95 | O | OCH2CH3 | H | CH2 | C2H5 |
| S-96 | O | OCH2CH3 | H | CH2 | n-C3H7 |
| S-97 | O | OCH2CH3 | H | CH2 | iso-C3H7 |
| S-98 | O | OCH2CH3 | H | CH2 | n-C4H9 |
| S-99 | O | OCH2CH3 | H | CH2 | iso-C4H9 |
| S-100 | O | OCH2CH3 | H | CH2 | sec-C4H9 |
| S-101 | O | OCH2CH3 | H | CH2 | tert-C4H9 |
| S-102 | O | OCH2CH3 | H | CH2 | n-C5H11 |
| S-103 | O | OCH2CH3 | H | CH2 | n-C6H13 |
| S-104 | O | OCH2CH3 | H | CH2 | cyclo-C3H5 |
| S-105 | O | OCH2CH3 | H | CH2 | cyclo-C5H9 |
| S-106 | O | OCH2CH3 | H | CH2 | cyclo-C6H11 |
| S-107 | O | OCH2CH3 | H | CH2 | CH2=CHCH2 |
| S-108 | O | OCH2CH3 | H | CH2 | CHCCH2 |
| S-109 | O | OCH2CH3 | H | CH2 | PhCH2 |
| S-110 | O | OCH2CH3 | H | CH2 | Ph(CH3)CH |
| S-111 | O | OCH2CH3 | H | CH2 | Ph(CH3)2C |
| S-112 | O | OCH2CH3 | H | CH2 | Ph |
| S-113 | O | OCH2CH3 | H | CH2 | 2-Cl—Ph |
| S-114 | O | OCH2CH3 | H | CH2 | 3-Cl—Ph |
| S-115 | O | OCH2CH3 | H | CH2 | 4-Cl—Ph |
| S-116 | O | OCH2CH3 | H | CH2 | 4-CF3O—Ph |
| S-117 | O | OCH2CH3 | H | CH2 | 4-(4-CF3—PhO)—Ph |
| S-118 | O | H | H | C=O | H |
| S-119 | O | H | H | C=O | n-C3H7 |
| S-120 | O | H | H | C=O | iso-C3H7 |
| S-121 | O | H | H | C=O | n-C4H9 |
| S-122 | O | H | H | C=O | iso-C4H9 |
| S-123 | O | H | H | C=O | sec-C4H9 |
| S-124 | O | H | H | C=O | tert-C4H9 |
| S-125 | O | H | H | C=O | n-C5H11 |
| S-126 | O | H | H | C=O | n-C6H13 |
| S-127 | O | H | H | C=O | cyclo-C3H5 |
| S-128 | O | H | H | C=O | cycto-C5H9 |
| S-129 | O | H | H | C=O | cyclo-C6H11 |
| S-130 | O | H | H | C=O | CH2=CHCH2 |

TABLE 4-continued

Compounds of formula (IA):

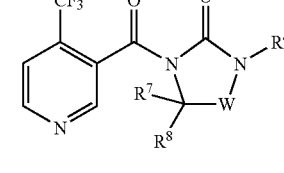

| Compound | U | R⁷ | R⁸ | W | R⁴ |
|---|---|---|---|---|---|
| S-131 | O | H | H | C=O | CHCCH2 |
| S-132 | O | H | H | C=O | PhCH2 |
| S-133 | O | H | H | C=O | Ph(CH3)CH |
| S-134 | O | H | H | C=O | Ph(CH3)2C |
| S-135 | O | H | H | C=O | Ph |
| S-136 | O | H | H | C=O | 2-Cl—Ph |
| S-137 | O | H | H | C=O | 3-Cl—Ph |
| S-138 | O | H | H | C=O | 4-Cl—Ph |
| S-139 | O | H | H | C=O | 4-CF3O—Ph |
| S-140 | O | H | H | C=O | 4-(4-CF3—PhO)—Ph |
| S-141 | O | CH3 | H | C=O | C2H5 |
| S-142 | O | CH3 | H | C=O | n-C3H7 |
| S-143 | O | CH3 | H | C=O | iso-C3H7 |
| S-144 | O | CH3 | H | C=O | n-C4H9 |
| S-145 | O | CH3 | H | C=O | iso-C4H9 |
| S-146 | O | CH3 | H | C=O | sec-C4H9 |
| S-147 | O | CH3 | H | C=O | tert-C4H9 |
| S-148 | O | CH3 | H | C=O | n-C5H11 |
| S-149 | O | CH3 | H | C=O | n-C6H13 |
| S-150 | O | CH3 | H | C=O | cyclo-C3H5 |
| S-151 | O | CH3 | H | C=O | cyclo-C5H9 |
| S-152 | O | CH3 | H | C=O | cyclo-C6H11 |
| S-153 | O | CH3 | H | C=O | CH2=CHCH2 |
| S-154 | O | CH3 | H | C=O | CHCCH2 |
| S-155 | O | CH3 | H | C=O | PhCH2 |
| S-156 | O | CH3 | H | C=O | Ph(CH3)CH |
| S-157 | O | CH3 | H | C=O | Ph(CH3)2C |
| S-158 | O | CH3 | H | C=O | Ph |
| S-159 | O | CH3 | H | C=O | 2-Cl—Ph |
| S-160 | O | CH3 | H | C=O | 3-Cl—Ph |
| S-161 | O | CH3 | H | C=O | 4-Cl—Ph |
| S-162 | O | CH3 | H | C=O | 4-CF3O—Ph |
| S-163 | O | CH3 | H | C=O | 4-(4-CF3—PhO)—Ph |
| S-164 | O | CH3 | CH3 | C=O | CH3 |
| S-165 | O | CH3 | CH3 | C=O | C2H5 |
| S-166 | O | CH3 | CH3 | C=O | n-C3H7 |
| S-167 | O | CH3 | CH3 | C=O | iso-C3H7 |
| S-168 | O | CH3 | CH3 | C=O | n-C4H9 |
| S-169 | O | CH3 | CH3 | C=O | iso-C4H9 |
| S-170 | O | CH3 | CH3 | C=O | sec-C4H9 |
| S-171 | O | CH3 | CH3 | C=O | tert-C4H9 |
| S-172 | O | CH3 | CH3 | C=O | n-C5H11 |
| S-173 | O | CH3 | CH3 | C=O | n-C6H13 |
| S-174 | O | CH3 | CH3 | C=O | cyclo-C3H5 |
| S-175 | O | CH3 | CH3 | C=O | cyclo-C5H9 |
| S-176 | O | CH3 | CH3 | C=O | cyclo-C6H11 |
| S-177 | O | CH3 | CH3 | C=O | CH2=CHCH2 |
| S-178 | O | CH3 | CH3 | C=O | CHCCH2 |
| S-179 | O | CH3 | CH3 | C=O | PhCH2 |
| S-180 | O | CH3 | CH3 | C=O | Ph(CH3)CH |
| S-181 | O | CH3 | CH3 | C=O | Ph(CH3)2C |
| S-182 | O | CH3 | CH3 | C=O | Ph |
| S-183 | O | CH3 | CH3 | C=O | 2-Cl—Ph |
| S-184 | O | CH3 | CH3 | C=O | 3-Cl—Ph |
| S-185 | O | CH3 | CH3 | C=O | 4-Cl—Ph |
| S-186 | O | CH3 | CH3 | C=O | 4-CF3O—Ph |
| S-187 | O | CH3 | CH3 | C=O | 4-(4-CF3—PhO)—Ph |
| S-188 | O | OCH3 | H | C=O | C2H5 |
| S-189 | O | OCH3 | H | C=O | n-C3H7 |
| S-190 | O | OCH3 | H | C=O | iso-C3H7 |
| S-191 | O | OCH3 | H | C=O | n-C4H9 |
| S-192 | O | OCH3 | H | C=O | iso-C4H9 |
| S-193 | O | OCH3 | H | C=O | sec-C4H9 |
| S-194 | O | OCH3 | H | C=O | tert-C4H9 |
| S-195 | O | OCH3 | H | C=O | n-C5H11 |
| S-196 | O | OCH3 | H | C=O | n-C6H13 |
| S-197 | O | OCH3 | H | C=O | cyclo-C3H5 |
| S-198 | O | OCH3 | H | C=O | cyclo-C5H9 |
| S-199 | O | OCH3 | H | C=O | cyclo-C6H11 |
| S-200 | O | OCH3 | H | C=O | CH2=CHCH2 |
| S-201 | O | OCH3 | H | C=O | CHCCH2 |
| S-202 | O | OCH3 | H | C=O | PhCH2 |
| S-203 | O | OCH3 | H | C=O | Ph(CH3)CH |
| S-204 | O | OCH3 | H | C=O | Ph(CH3)2C |
| S-205 | O | OCH3 | H | C=O | Ph |
| S-206 | O | OCH3 | H | C=O | 2-Cl—Ph |
| S-207 | O | OCH3 | H | C=O | 3-Cl—Ph |
| S-208 | O | OCH3 | H | C=O | 4-Cl—Ph |
| S-209 | O | OCH3 | H | C=O | 4-CF3O—Ph |
| S-210 | O | OCH3 | H | C=O | 4-(4-CF3—PhO)—Ph |
| S-211 | O | OCH2CH3 | H | C=O | CH3 |
| S-212 | O | OCH2CH3 | H | C=O | C2H5 |
| S-213 | O | OCH2CH3 | H | C=O | n-C3H7 |
| S-214 | O | OCH2CH3 | H | C=O | iso-C3H7 |
| S-215 | O | OCH2CH3 | H | C=O | n-C4H9 |
| S-216 | O | OCH2CH3 | H | C=O | iso-C4H9 |
| S-217 | O | OCH2CH3 | H | C=O | sec-C4H9 |
| S-218 | O | OCH2CH3 | H | C=O | tert-C4H9 |
| S-219 | O | OCH2CH3 | H | C=O | n-C5H11 |
| S-220 | O | OCH2CH3 | H | C=O | n-C6H13 |
| S-221 | O | OCH2CH3 | H | C=O | cyclo-C3H5 |
| S-222 | O | OCH2CH3 | H | C=O | cyclo-C5H9 |
| S-223 | O | OCH2CH3 | H | C=O | cyclo-C6H11 |
| S-224 | O | OCH2CH3 | H | C=O | CH2=CHCH2 |
| S-225 | O | OCH2CH3 | H | C=O | CHCCH2 |
| S-226 | O | OCH2CH3 | H | C=O | PhCH2 |
| S-227 | O | OCH2CH3 | H | C=O | Ph(CH3)CH |
| S-228 | O | OCH2CH3 | H | C=O | Ph(CH3)2C |
| S-229 | O | OCH2CH3 | H | C=O | Ph |
| S-230 | O | OCH2CH3 | H | C=O | 2-Cl—Ph |
| S-231 | O | OCH2CH3 | H | C=O | 3-Cl—Ph |
| S-232 | O | OCH2CH3 | H | C=O | 4-Cl—Ph |
| S-233 | O | OCH2CH3 | H | C=O | 4-CF3O—Ph |
| S-234 | O | OCH2CH3 | H | C=O | 4-(4-CF3—PhO)—Ph |
| S-235 | O | H | H | CH2CH2 | C2H5 |
| S-236 | O | H | H | CH2CH2 | n-C3H7 |
| S-237 | O | H | H | CH2CH2 | iso-C3H7 |
| S-238 | O | H | H | CH2CH2 | n-C4H9 |
| S-239 | O | H | H | CH2CH2 | iso-C4H9 |
| S-240 | O | H | H | CH2CH2 | sec-C4H9 |
| S-241 | O | H | H | CH2CH2 | tert-C4H9 |
| S-242 | O | H | H | CH2CH2 | n-C5H11 |
| S-243 | O | H | H | CH2CH2 | n-C6H13 |
| S-244 | O | H | H | CH2CH2 | cyclo-C3H5 |
| S-245 | O | H | H | CH2CH2 | cyclo-C5H9 |
| S-246 | O | H | H | CH2CH2 | cyclo-C6H11 |
| S-247 | O | H | H | CH2CH2 | CH2=CHCH2 |
| S-248 | O | H | H | CH2CH2 | CHCCH2 |
| S-249 | O | H | H | CH2CH2 | PhCH2 |
| S-250 | O | H | H | CH2CH2 | Ph(CH3)CH |
| S-251 | O | H | H | CH2CH2 | Ph(CH3)2C |
| S-252 | O | H | H | CH2CH2 | Ph |
| S-253 | O | H | H | CH2CH2 | 2-Cl—Ph |
| S-254 | O | H | H | CH2CH2 | 3-Cl—Ph |
| S-255 | O | H | H | CH2CH2 | 4-Cl—Ph |
| S-256 | O | H | H | CH2CH2 | 4-CF3O—Ph |
| S-257 | O | H | H | CH2CH2 | 4-(4-CF3—PhO)—Ph |
| S-258 | O | CH3 | H | CH2CH2 | CH3 |
| S-259 | O | CH3 | H | CH2CH2 | C2H5 |
| S-260 | O | CH3 | H | CH2CH2 | n-C3H7 |

TABLE 4-continued

Compounds of formula (IA):

| Compound | U | R⁷ | R⁸ | W | R⁴ |
|---|---|---|---|---|---|
| S-261 | O | CH3 | H | CH2CH2 | iso-C3H7 |
| S-262 | O | CH3 | H | CH2CH2 | n-C4H9 |
| S-263 | O | CH3 | H | CH2CH2 | iso-C4H9 |
| S-264 | O | CH3 | H | CH2CH2 | sec-C4H9 |
| S-265 | O | CH3 | H | CH2CH2 | tert-C4H9 |
| S-266 | O | CH3 | H | CH2CH2 | n-C5H11 |
| S-267 | O | CH3 | H | CH2CH2 | n-C6H13 |
| S-268 | O | CH3 | H | CH2CH2 | cyclo-C3H5 |
| S-269 | O | CH3 | H | CH2CH2 | cyclo-C5H9 |
| S-270 | O | CH3 | H | CH2CH2 | cyclo-C6H11 |
| S-271 | O | CH3 | H | CH2CH2 | CH2=CHCH2 |
| S-272 | O | CH3 | H | CH2CH2 | CHCCH2 |
| S-273 | O | CH3 | H | CH2CH2 | PhCH2 |
| S-274 | O | CH3 | H | CH2CH2 | Ph(CH3)CH |
| S-275 | O | CH3 | H | CH2CH2 | Ph(CH3)2C |
| S-276 | O | CH3 | H | CH2CH2 | Ph |
| S-277 | O | CH3 | H | CH2CH2 | 2-Cl—Ph |
| S-278 | O | CH3 | H | CH2CH2 | 3-Cl—Ph |
| S-279 | O | CH3 | H | CH2CH2 | 4-Cl—Ph |
| S-280 | O | CH3 | H | CH2CH2 | 4-CF3O—Ph |
| S-281 | O | CH3 | H | CH2CH2 | 4-(4-CF3—PhO)—Ph |
| S-282 | O | CH3 | CH3 | CH2CH2 | H |
| S-283 | O | CH3 | CH3 | CH2CH2 | CH3 |
| S-284 | O | CH3 | CH3 | CH2CH2 | C2H5 |
| S-285 | O | CH3 | CH3 | CH2CH2 | n-C3H7 |
| S-286 | O | CH3 | CH3 | CH2CH2 | iso-C3H7 |
| S-287 | O | CH3 | CH3 | CH2CH2 | n-C4H9 |
| S-288 | O | CH3 | CH3 | CH2CH2 | iso-C4H9 |
| S-289 | O | CH3 | CH3 | CH2CH2 | sec-C4H9 |
| S-290 | O | CH3 | CH3 | CH2CH2 | tert-C4H9 |
| S-291 | O | CH3 | CH3 | CH2CH2 | n-C5H11 |
| S-292 | O | CH3 | CH3 | CH2CH2 | n-C6H13 |
| S-293 | O | CH3 | CH3 | CH2CH2 | cyclo-C3H5 |
| S-294 | O | CH3 | CH3 | CH2CH2 | cyclo-C5H9 |
| S-295 | O | CH3 | CH3 | CH2CH2 | cyclo-C6H11 |
| S-296 | O | CH3 | CH3 | CH2CH2 | CH2=CHCH2 |
| S-297 | O | CH3 | CH3 | CH2CH2 | CHCCH2 |
| S-298 | O | CH3 | CH3 | CH2CH2 | PhCH2 |
| S-299 | O | CH3 | CH3 | CH2CH2 | Ph(CH3)CH |
| S-300 | O | CH3 | CH3 | CH2CH2 | Ph(CH3)2C |
| S-301 | O | CH3 | CH3 | CH2CH2 | Ph |
| S-302 | O | CH3 | CH3 | CH2CH2 | 2-Cl—Ph |
| S-303 | O | CH3 | CH3 | CH2CH2 | 3-Cl—Ph |
| S-304 | O | CH3 | CH3 | CH2CH2 | 4-Cl—Ph |
| S-305 | O | CH3 | CH3 | CH2CH2 | 4-CF3O—Ph |
| S-306 | O | CH3 | CH3 | CH2CH2 | 4-(4-CF3—PhO)—Ph |
| S-307 | O | OCH3 | H | CH2CH2 | CH3 |
| S-308 | O | OCH3 | H | CH2CH2 | C2H5 |
| S-309 | O | OCH3 | H | CH2CH2 | n-C3H7 |
| S-310 | O | OCH3 | H | CH2CH2 | iso-C3H7 |
| S-311 | O | OCH3 | H | CH2CH2 | n-C4H9 |
| S-312 | O | OCH3 | H | CH2CH2 | iso-C4H9 |
| S-313 | O | OCH3 | H | CH2CH2 | sec-C4H9 |
| S-314 | O | OCH3 | H | CH2CH2 | tert-C4H9 |
| S-315 | O | OCH3 | H | CH2CH2 | n-C5H11 |
| S-316 | O | OCH3 | H | CH2CH2 | n-C6H13 |
| S-317 | O | OCH3 | H | CH2CH2 | cyclo-C3H5 |
| S-318 | O | OCH3 | H | CH2CH2 | cyclo-C5H9 |
| S-319 | O | OCH3 | H | CH2CH2 | cyclo-C6H11 |
| S-320 | O | OCH3 | H | CH2CH2 | CH2=CHCH2 |
| S-321 | O | OCH3 | H | CH2CH2 | CHCCH2 |
| S-322 | O | OCH3 | H | CH2CH2 | PhCH2 |
| S-323 | O | OCH3 | H | CH2CH2 | Ph(CH3)CH |
| S-324 | O | OCH3 | H | CH2CH2 | Ph(CH3)2C |
| S-325 | O | OCH3 | H | CH2CH2 | Ph |
| S-326 | O | OCH3 | H | CH2CH2 | 2-Cl—Ph |
| S-327 | O | OCH3 | H | CH2CH2 | 3-Cl—Ph |
| S-328 | O | OCH3 | H | CH2CH2 | 4-Cl—Ph |
| S-329 | O | OCH3 | H | CH2CH2 | 4-CF3O—Ph |
| S-330 | O | OCH3 | H | CH2CH2 | 4-(4-CF3—PhO)—Ph |
| S-331 | O | OCH2CH3 | H | CH2CH2 | H |
| S-332 | O | OCH2CH3 | H | CH2CH2 | CH3 |
| S-333 | O | OCH2CH3 | H | CH2CH2 | C2H5 |
| S-334 | O | OCH2CH3 | H | CH2CH2 | n-C3H7 |
| S-335 | O | OCH2CH3 | H | CH2CH2 | iso-C3H7 |
| S-336 | O | OCH2CH3 | H | CH2CH2 | n-C4H9 |
| S-337 | O | OCH2CH3 | H | CH2CH2 | iso-C4H9 |
| S-338 | O | OCH2CH3 | H | CH2CH2 | sec-C4H9 |
| S-339 | O | OCH2CH3 | H | CH2CH2 | tert-C4H9 |
| S-340 | O | OCH2CH3 | H | CH2CH2 | n-C5H11 |
| S-341 | O | OCH2CH3 | H | CH2CH2 | n-C6H13 |
| S-342 | O | OCH2CH3 | H | CH2CH2 | cyclo-C3H5 |
| S-343 | O | OCH2CH3 | H | CH2CH2 | cyclo-C5H9 |
| S-344 | O | OCH2CH3 | H | CH2CH2 | cyclo-C6H11 |
| S-345 | O | OCH2CH3 | H | CH2CH2 | CH2=CHCH2 |
| S-346 | O | OCH2CH3 | H | CH2CH2 | CHCCH2 |
| S-347 | O | OCH2CH3 | H | CH2CH2 | PhCH2 |
| S-348 | O | OCH2CH3 | H | CH2CH2 | Ph(CH3)CH |
| S-349 | O | OCH2CH3 | H | CH2CH2 | Ph(CH3)2C |
| S-350 | O | OCH2CH3 | H | CH2CH2 | Ph |
| S-351 | O | OCH2CH3 | H | CH2CH2 | 2-Cl—Ph |
| S-352 | O | OCH2CH3 | H | CH2CH2 | 3-Cl—Ph |
| S-353 | O | OCH2CH3 | H | CH2CH2 | 4-Cl—Ph |
| S-354 | O | OCH2CH3 | H | CH2CH2 | 4-CF3O—Ph |
| S-355 | O | OCH2CH3 | H | CH2CH2 | 4-(4-CF3—PhO)—Ph |
| S-356 | S | H | H | CH2 | H |
| S-357 | S | H | H | CH2 | n-C3H7 |
| S-358 | S | H | H | CH2 | iso-C3H7 |
| S-359 | S | H | H | CH2 | n-C4H9 |
| S-360 | S | H | H | CH2 | iso-C4H9 |
| S-361 | S | H | H | CH2 | sec-C4H9 |
| S-362 | S | H | H | CH2 | tert-C4H9 |
| S-363 | S | H | H | CH2 | n-C5H11 |
| S-364 | S | H | H | CH2 | n-C6H13 |
| S-365 | S | H | H | CH2 | cyclo-C3H5 |
| S-366 | S | H | H | CH2 | cyclo-C5H9 |
| S-367 | S | H | H | CH2 | cyclo-C6H11 |
| S-368 | S | H | H | CH2 | CH2=CHCH2 |
| S-369 | S | H | H | CH2 | CHCCH2 |
| S-370 | S | H | H | CH2 | PhCH2 |
| S-371 | S | H | H | CH2 | Ph(CH3)CH |
| S-372 | S | H | H | CH2 | Ph(CH3)2C |
| S-373 | S | H | H | CH2 | Ph |
| S-374 | S | H | H | CH2 | 2-Cl—Ph |
| S-375 | S | H | H | CH2 | 3-Cl—Ph |
| S-376 | S | H | H | CH2 | 4-Cl—Ph |
| S-377 | S | H | H | CH2 | 4-CF3O—Ph |
| S-378 | S | H | H | CH2 | 4-(4-CF3—PhO)—Ph |
| S-379 | S | CH3 | H | CH2 | C2H5 |
| S-380 | S | CH3 | H | CH2 | n-C3H7 |
| S-381 | S | CH3 | H | CH2 | iso-C3H7 |
| S-382 | S | CH3 | H | CH2 | n-C4H9 |
| S-383 | S | CH3 | H | CH2 | iso-C4H9 |
| S-384 | S | CH3 | H | CH2 | sec-C4H9 |
| S-385 | S | CH3 | H | CH2 | tert-C4H9 |
| S-386 | S | CH3 | H | CH2 | n-C5H11 |
| S-387 | S | CH3 | H | CH2 | n-C6H13 |
| S-388 | S | CH3 | H | CH2 | cyclo-C3H5 |
| S-389 | S | CH3 | H | CH2 | cyclo-C5H9 |
| S-390 | S | CH3 | H | CH2 | cyclo-C6H11 |

TABLE 4-continued

Compounds of formula (IA):

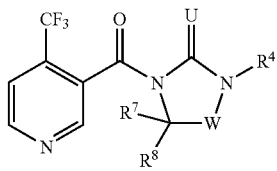
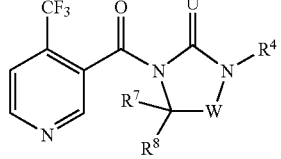

(IA)

| Compound | U | R⁷ | R⁸ | W | R⁴ |
|---|---|---|---|---|---|
| S-391 | S | CH3 | H | CH2 | CH2=CHCH2 |
| S-392 | S | CH3 | H | CH2 | CHCCH2 |
| S-393 | S | CH3 | H | CH2 | PhCH2 |
| S-394 | S | CH3 | H | CH2 | Ph(CH3)CH |
| S-395 | S | CH3 | H | CH2 | Ph(CH3)2C |
| S-396 | S | CH3 | H | CH2 | Ph |
| S-397 | S | CH3 | H | CH2 | 2-Cl—Ph |
| S-398 | S | CH3 | H | CH2 | 3-Cl—Ph |
| S-399 | S | CH3 | H | CH2 | 4-Cl—Ph |
| S-400 | S | CH3 | H | CH2 | 4-CF3O—Ph |
| S-401 | S | CH3 | H | CH2 | 4-(4-CF3—PhO)—Ph |
| S-402 | S | CH3 | CH3 | CH2 | CH3 |
| S-403 | S | CH3 | CH3 | CH2 | C2H5 |
| S-404 | S | CH3 | CH3 | CH2 | n-C3H7 |
| S-405 | S | CH3 | CH3 | CH2 | iso-C3H7 |
| S-406 | S | CH3 | CH3 | CH2 | n-C4H9 |
| S-407 | S | CH3 | CH3 | CH2 | iso-C4H9 |
| S-408 | S | CH3 | CH3 | CH2 | sec-C4H9 |
| S-409 | S | CH3 | CH3 | CH2 | tert-C4H9 |
| S-410 | S | CH3 | CH3 | CH2 | n-C5H11 |
| S-411 | S | CH3 | CH3 | CH2 | n-C6H13 |
| S-412 | S | CH3 | CH3 | CH2 | cyclo-C3H5 |
| S-413 | S | CH3 | CH3 | CH2 | cyclo-C5H9 |
| S-414 | S | CH3 | CH3 | CH2 | cyclo-C6H11 |
| S-415 | S | CH3 | CH3 | CH2 | CH2=CHCH2 |
| S-416 | S | CH3 | CH3 | CH2 | CHCCH2 |
| S-417 | S | CH3 | CH3 | CH2 | PhCH2 |
| S-418 | S | CH3 | CH3 | CH2 | Ph(CH3)CH |
| S-419 | S | CH3 | CH3 | CH2 | Ph(CH3)2C |
| S-420 | S | CH3 | CH3 | CH2 | Ph |
| S-421 | S | CH3 | CH3 | CH2 | 2-Cl—Ph |
| S-422 | S | CH3 | CH3 | CH2 | 3-Cl—Ph |
| S-423 | S | CH3 | CH3 | CH2 | 4-Cl—Ph |
| S-424 | S | CH3 | CH3 | CH2 | 4-CF3O—Ph |
| S-425 | S | CH3 | CH3 | CH2 | 4-(4-CF3—PhO)—Ph |
| S-426 | S | OCH3 | H | CH2 | C2H5 |
| S-427 | S | OCH3 | H | CH2 | n-C3H7 |
| S-428 | S | OCH3 | H | CH2 | iso-C3H7 |
| S-429 | S | OCH3 | H | CH2 | n-C4H9 |
| S-430 | S | OCH3 | H | CH2 | iso-C4H9 |
| S-431 | S | OCH3 | H | CH2 | sec-C4H9 |
| S-432 | S | OCH3 | H | CH2 | tert-C4H9 |
| S-433 | S | OCH3 | H | CH2 | n-C5H11 |
| S-434 | S | OCH3 | H | CH2 | n-C6H13 |
| S-435 | S | OCH3 | H | CH2 | cyclo-C3H5 |
| S-436 | S | OCH3 | H | CH2 | cyclo-C5H9 |
| S-437 | S | OCH3 | H | CH2 | cyclo-C6H11 |
| S-438 | S | OCH3 | H | CH2 | CH2=CHCH2 |
| S-439 | S | OCH3 | H | CH2 | CHCCH2 |
| S-440 | S | OCH3 | H | CH2 | PhCH2 |
| S-441 | S | OCH3 | H | CH2 | Ph(CH3)CH |
| S-442 | S | OCH3 | H | CH2 | Ph(CH3)2C |
| S-443 | S | OCH3 | H | CH2 | Ph |
| S-444 | S | OCH3 | H | CH2 | 2-Cl—Ph |
| S-445 | S | OCH3 | H | CH2 | 3-Cl—Ph |
| S-446 | S | OCH3 | H | CH2 | 4-Cl—Ph |
| S-447 | S | OCH3 | H | CH2 | 4-CF3O—Ph |
| S-448 | S | OCH3 | H | CH2 | 4-(4-CF3—PhO)—Ph |
| S-449 | S | H | H | CH2CH2 | C2H5 |
| S-450 | S | H | H | CH2CH2 | n-C3H7 |
| S-451 | S | H | H | CH2CH2 | iso-C3H7 |
| S-452 | S | H | H | CH2CH2 | n-C4H9 |
| S-453 | S | H | H | CH2CH2 | iso-C4H9 |
| S-454 | S | H | H | CH2CH2 | sec-C4H9 |
| S-455 | S | H | H | CH2CH2 | tert-C4H9 |
| S-456 | S | H | H | CH2CH2 | n-C5H11 |
| S-457 | S | H | H | CH2CH2 | n-C6H13 |
| S-458 | S | H | H | CH2CH2 | cyclo-C3H5 |
| S-459 | S | H | H | CH2CH2 | cyclo-C5H9 |
| S-460 | S | H | H | CH2CH2 | cyclo-C6H11 |
| S-461 | S | H | H | CH2CH2 | CH2=CHCH2 |
| S-462 | S | H | H | CH2CH2 | CHCCH2 |
| S-463 | S | H | H | CH2CH2 | PhCH2 |
| S-464 | S | H | H | CH2CH2 | Ph(CH3)CH |
| S-465 | S | H | H | CH2CH2 | Ph(CH3)2C |
| S-466 | S | H | H | CH2CH2 | Ph |
| S-467 | S | H | H | CH2CH2 | 2-Cl—Ph |
| S-468 | S | H | H | CH2CH2 | 3-Cl—Ph |
| S-469 | S | H | H | CH2CH2 | 4-Cl—Ph |
| S-470 | S | H | H | CH2CH2 | 4-CF3O—Ph |
| S-471 | S | H | H | CH2CH2 | 4-(4-CF3—PhO)—Ph |
| S-472 | S | CH3 | H | CH2CH2 | CH3 |
| S-473 | S | CH3 | H | CH2CH2 | C2H5 |
| S-474 | S | CH3 | H | CH2CH2 | n-C3H7 |
| S-475 | S | CH3 | H | CH2CH2 | iso-C3H7 |
| S-476 | S | CH3 | H | CH2CH2 | n-C4H9 |
| S-477 | S | CH3 | H | CH2CH2 | iso-C4H9 |
| S-478 | S | CH3 | H | CH2CH2 | sec-C4H9 |
| S-479 | S | CH3 | H | CH2CH2 | tert-C4H9 |
| S-480 | S | CH3 | H | CH2CH2 | n-C5H11 |
| S-481 | S | CH3 | H | CH2CH2 | n-C6H13 |
| S-482 | S | CH3 | H | CH2CH2 | cyclo-C3H5 |
| S-483 | S | CH3 | H | CH2CH2 | cyclo-C5H9 |
| S-484 | S | CH3 | H | CH2CH2 | cyclo-C6H11 |
| S-485 | S | CH3 | H | CH2CH2 | CH2=CHCH2 |
| S-486 | S | CH3 | H | CH2CH2 | CHCCH2 |
| S-487 | S | CH3 | H | CH2CH2 | PhCH2 |
| S-488 | S | CH3 | H | CH2CH2 | Ph(CH3)CH |
| S-489 | S | CH3 | H | CH2CH2 | Ph(CH3)2C |
| S-490 | S | CH3 | H | CH2CH2 | Ph |
| S-491 | S | CH3 | H | CH2CH2 | 2-Cl—Ph |
| S-492 | S | CH3 | H | CH2CH2 | 3-Cl—Ph |
| S-493 | S | CH3 | H | CH2CH2 | 4-Cl—Ph |
| S-494 | S | CH3 | H | CH2CH2 | 4-CF3O—Ph |
| S-495 | S | CH3 | H | CH2CH2 | 4-(4-CF3—PhO)—Ph |
| S-496 | S | CH3 | CH3 | CH2CH2 | H |
| S-497 | S | CH3 | CH3 | CH2CH2 | CH3 |
| S-498 | S | CH3 | CH3 | CH2CH2 | C2H5 |
| S-499 | S | CH3 | CH3 | CH2CH2 | n-C3H7 |
| S-500 | S | CH3 | CH3 | CH2CH2 | iso-C3H7 |
| S-501 | S | CH3 | CH3 | CH2CH2 | n-C4H9 |
| S-502 | S | CH3 | CH3 | CH2CH2 | iso-C4H9 |
| S-503 | S | CH3 | CH3 | CH2CH2 | sec-C4H9 |
| S-504 | S | CH3 | CH3 | CH2CH2 | n-C4H9 |
| S-505 | S | CH3 | CH3 | CH2CH2 | iso-C4H9 |
| S-506 | S | CH3 | CH3 | CH2CH2 | seo-C4H9 |
| S-507 | S | CH3 | CH3 | CH2CH2 | tert-C4H9 |
| S-508 | S | CH3 | CH3 | CH2CH2 | n-C5H11 |
| S-509 | S | CH3 | CH3 | CH2CH2 | n-C6H13 |
| S-510 | S | CH3 | CH3 | CH2CH2 | cyclo-C3H5 |
| S-511 | S | CH3 | CH3 | CH2CH2 | cyclo-C5H9 |
| S-512 | S | CH3 | CH3 | CH2CH2 | cyclo-C6H11 |
| S-513 | S | CH3 | CH3 | CH2CH2 | CH2=CHCH2 |
| S-514 | S | CH3 | CH3 | CH2CH2 | CHCCH2 |
| S-515 | S | CH3 | CH3 | CH2CH2 | PhCH2 |
| S-516 | S | CH3 | CH3 | CH2CH2 | Ph(CH3)CH |
| S-517 | S | CH3 | CH3 | CH2CH2 | Ph(CH3)2C |
| S-518 | S | CH3 | CH3 | CH2CH2 | Ph |
| S-519 | S | CH3 | CH3 | CH2CH2 | 2-Cl—Ph |
| S-520 | S | CH3 | CH3 | CH2CH2 | 3-Cl—Ph |

TABLE 4-continued

Compounds of formula (IA):

(IA)

| Compound | U | R⁷ | R⁸ | W | R⁴ |
|---|---|---|---|---|---|
| S-521 | S | CH3 | CH3 | CH2CH2 | 4-Cl—Ph |
| S-522 | S | CH3 | CH3 | CH2CH2 | 4-CF3O—Ph |
| S-523 | S | CH3 | CH3 | CH2CH2 | 4-(4-CF3—PhO)—Ph |
| S-524 | S | OCH3 | H | CH2CH2 | CH3 |
| S-525 | S | OCH3 | H | CH2CH2 | C2H5 |
| S-526 | S | OCH3 | H | CH2CH2 | n-C3H7 |
| S-527 | S | OCH3 | H | CH2CH2 | iso-C3H7 |
| S-528 | S | OCH3 | H | CH2CH2 | n-C4H9 |
| S-529 | S | OCH3 | H | CH2CH2 | iso-C4H9 |
| S-530 | S | OCH3 | H | CH2CH2 | sec-C4H9 |
| S-531 | S | OCH3 | H | CH2CH2 | tert-C4H9 |
| S-532 | S | OCH3 | H | CH2CH2 | n-C5H11 |
| S-533 | S | OCH3 | H | CH2CH2 | n-C6H13 |
| S-534 | S | OCH3 | H | CH2CH2 | cyclo-C3H5 |
| S-535 | S | OCH3 | H | CH2CH2 | cyclo-C5H9 |
| S-536 | S | OCH3 | H | CH2CH2 | cyclo-C6H11 |
| S-537 | S | OCH3 | H | CH2CH2 | CH2=CHCH2 |
| S-538 | S | OCH3 | H | CH2CH2 | CHCCH2 |
| S-539 | S | OCH3 | H | CH2CH2 | PhCH2 |
| S-540 | S | OCH3 | H | CH2CH2 | Ph(CH3)CH |
| S-541 | S | OCH3 | H | CH2CH2 | Ph(CH3)2C |
| S-542 | S | OCH3 | H | CH2CH2 | Ph |
| S-543 | S | OCH3 | H | CH2CH2 | 2-Cl—Ph |
| S-544 | S | OCH3 | H | CH2CH2 | 3-Cl—Ph |
| S-545 | S | OCH3 | H | CH2CH2 | 4-Cl—Ph |
| S-546 | S | OCH3 | H | CH2CH2 | 4-CF3O—Ph |
| S-547 | S | OCH3 | H | CH2CH2 | 4-(4-CF3—PhO)—Ph |
| S-548 | O | H | H | CH2 | CH3O |
| S-549 | O | H | H | CH2 | PhCH2O |
| S-550 | O | H | H | CH(CH3) | H |
| S-551 | O | H | H | CH(C2H5) | H |
| S-552 | O | H | H | CH(C2H5) | PhCH2 |
| S-553 | O | H | H | CHPh | H |
| S-554 | O | H | H | CHPh | CH3 |
| S-555 | O | H | H | CHPh | PhCH2 |
| S-556 | O | CH3 | H | CH2 | H |
| S-557 | O | Ph | H | CH2 | H |
| S-558 | O | Ph | H | CH2 | CH3 |
| S-559 | O | Ph | H | CH2 | PhCH2 |

TABLE 5

Compounds of formula (IB):

(1B)

| Compound | U | X | Y | R⁴ |
|---|---|---|---|---|
| T-1 | O | CH | CH | H |
| T-2 | O | CH | CH | n-C3H7 |
| T-3 | O | CH | CH | iso-C3H7 |
| T-4 | O | CH | CH | n-C4H9 |
| T-5 | O | CH | CH | iso-C4H9 |
| T-6 | O | CH | CH | sec-C4H9 |
| T-7 | O | CH | CH | tert-C4H9 |
| T-8 | O | CH | CH | n-C5H11 |
| T-9 | O | CH | CH | n-C6H13 |
| T-10 | O | CH | CH | cyclo-C3H5 |
| T-11 | O | CH | CH | cyclo-C5H9 |
| T-12 | O | CH | CH | cyclo-C6H11 |
| T-13 | O | CH | CH | CH2=CHCH2 |
| T-14 | O | CH | CH | CH2CCH |
| T-15 | O | CH | CH | PhCH2 |
| T-16 | O | CH | CH | Ph(CH3)OH |
| T-17 | O | CH | CH | Ph |
| T-18 | O | CH | CH | 2-Cl—Ph |
| T-19 | O | CH | CH | 3-Cl—Ph |
| T-20 | O | CH | CH | 4-Cl—Ph |
| T-21 | O | CH | CH | 4-CF3O—Ph |
| T-22 | O | CH | CH | 4-(4-CF3—PhO)—Ph |
| T-23 | O | CH | N | H |
| T-24 | O | CH | N | CH3 |
| T-25 | O | CH | N | n-C4H9 |
| T-26 | O | CH | N | iso-C4H9 |
| T-27 | O | CH | N | sec-C4H9 |
| T-28 | O | CH | N | tert-C4H9 |
| T-29 | O | CH | N | n-C5H11 |
| T-30 | O | CH | N | n-C6H13 |
| T-31 | O | CH | N | cyclo-C3H5 |
| T-32 | O | CH | N | cyclo-C5H9 |
| T-33 | O | CH | N | cyclo-C6H11 |
| T-34 | O | CH | N | CH2=CHCH2 |
| T-35 | O | CH | N | CH2CCH |
| T-36 | O | CH | N | PhCH2 |
| T-37 | O | CH | N | Ph(CH3)CH |
| T-38 | O | CH | N | Ph |
| T-39 | O | CH | N | 2-Cl—Ph |
| T-40 | O | CH | N | 3-Cl—Ph |
| T-41 | O | CH | N | 4-Cl—Ph |
| T-42 | O | CH | N | 4-CF3O—Ph |
| T-43 | O | CH | N | 4-(4-CF3—PhO)—Ph |
| T-44 | O | CH | N | H |
| T-45 | O | N | N | CH3 |
| T-46 | O | N | N | C2H5 |
| T-47 | O | N | N | n-C5H11 |
| T-48 | O | N | N | n-C6H13 |
| T-49 | O | N | N | cyclo-C3H5 |
| T-50 | O | N | N | cyclo-C5H9 |
| T-51 | O | N | N | cyclo-C6H11 |
| T-52 | O | N | N | CH2=CHCH2 |
| T-53 | O | N | N | CH2CCH |
| T-54 | O | N | N | PhCH2 |
| T-55 | O | N | N | Ph(CH3)CH |
| T-56 | O | N | N | Ph |
| T-57 | O | N | N | 2-Cl—Ph |
| T-58 | O | N | N | 3-Cl—Ph |
| T-59 | O | N | N | 4-Cl—Ph |
| T-60 | O | N | N | 4-CF3O—Ph |
| T-61 | O | N | N | 4-(4-CF3—PhO)—Ph |
| T-62 | S | CH | CH | H |
| T-63 | S | CH | CH | n-C3H7 |
| T-64 | S | CH | CH | iso-C3H7 |
| T-65 | S | CH | CH | n-C4H9 |
| T-66 | S | CH | CH | iso-C4H9 |
| T-67 | S | CH | CH | sec-C4H9 |
| T-68 | S | CH | CH | tert-C4H9 |
| T-69 | S | CH | CH | n-C5H11 |
| T-70 | S | CH | CH | n-C6H13 |
| T-71 | S | CH | CH | cyclo-C3H5 |
| T-72 | S | CH | CH | cyclo-C5H9 |
| T-73 | S | CH | CH | cyclo-C6H11 |
| T-74 | S | CH | CH | CH2=CHCH2 |

TABLE 5-continued

Compounds of formula (IB):

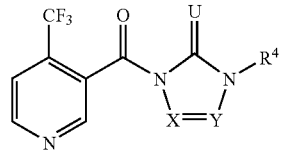

(1B)

| Compound | U | X | Y | R⁴ |
|---|---|---|---|---|
| T-75 | S | CH | CH | CH2CCH |
| T-76 | S | CH | CH | PhCH2 |
| T-77 | S | CH | CH | Ph(CH3)CH |
| T-78 | S | CH | CH | Ph |
| T-79 | S | CH | CH | 2-Cl—Ph |
| T-80 | S | CH | CH | 3-Cl—Ph |
| T-81 | S | CH | CH | 4-Cl—Ph |
| T-82 | S | CH | CH | 4-CF3O—Ph |
| T-83 | S | CH | CH | 4-(4-CF3—PhO)—Ph |
| T-84 | S | CH | N | H |
| T-85 | S | CH | N | CH3 |
| T-86 | S | CH | N | n-C4H9 |
| T-87 | S | CH | N | iso-C4H9 |
| T-88 | S | CH | N | sec-C4H9 |
| T-89 | S | CH | N | tert-C4H9 |
| T-90 | S | CH | N | n-C5H11 |
| T-91 | S | CH | N | n-C6H13 |
| T-92 | S | CH | N | cyclo-C3H5 |
| T-93 | S | CH | N | cyclo-C5H9 |
| T-94 | S | CH | N | cyclo-C6H11 |
| T-95 | S | CH | N | CH2=CHCH2 |
| T-96 | S | CH | N | CH2CCH |
| T-97 | S | CH | N | PhCH2 |
| T-98 | S | CH | N | Ph(CH3)OH |
| T-99 | S | CH | N | Ph |
| T-100 | S | CH | N | 2-Cl—Ph |
| T-101 | S | CH | N | 3-Cl—Ph |
| T-102 | S | CH | N | 4-Cl—Ph |
| T-103 | S | CH | N | 4-CF3O—Ph |
| T-104 | S | CH | N | 4-(4-CF3—PhO)—Ph |
| T-105 | S | N | N | H |
| T-106 | S | N | N | CH3 |
| T-107 | S | N | N | C2H5 |
| T-108 | S | N | N | n-C5H11 |
| T-109 | S | N | N | n-C6H13 |
| T-110 | S | N | N | cyclo-C3H5 |
| T-111 | S | N | N | cyclo-C5H9 |
| T-112 | S | N | N | cyclo-C6H11 |
| T-113 | S | N | N | CH2=CHCH2 |
| T-114 | S | N | N | CH2CCH |
| T-115 | S | N | N | PhCH2 |
| T-116 | S | N | N | Ph(CH3)CH |
| T-117 | S | N | N | Ph |
| T-118 | S | N | N | 2-Cl—Ph |
| T-119 | S | N | N | 3-Cl—Ph |
| T-120 | S | N | N | 4-Cl—Ph |
| T-121 | S | N | N | 4-CF3O—Ph |
| T-122 | S | N | N | 4-(4-CF3—PhO)—Ph |
| T-123 | S | N | N | Ph |

TABLE 6

Compounds of formula (IC):

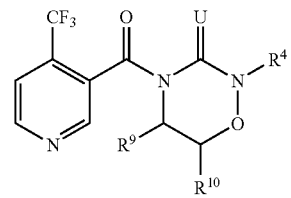

(1C)

| Compound | U | R⁴ | R⁹ | R¹⁰ |
|---|---|---|---|---|
| U-1 | O | H | H | H |
| U-2 | O | n-C3H7 | H | H |
| U-3 | O | iso-C3H7 | H | H |
| U-4 | O | n-C4H9 | H | H |
| U-5 | O | iso-C4H9 | H | H |
| U-6 | O | sec-C4H9 | H | H |
| U-7 | O | tert-C4H9 | H | H |
| U-8 | O | n-C5H11 | H | H |
| U-9 | O | n-C6H13 | H | H |
| U-10 | O | cyclo-C3H5 | H | H |
| U-11 | O | cyclo-C5H9 | H | H |
| U-12 | O | cyclo-C6H11 | H | H |
| U-13 | O | CH2CH=CH2 | H | H |
| U-14 | O | CH2C(CH3)=CH2 | H | H |
| U-15 | O | CH(CH3)CH=CH2 | H | H |
| U-16 | O | CH2CH=CHCH3 | H | H |
| U-17 | O | CH2CCH | H | H |
| U-18 | O | CH2CCCH3 | H | H |
| U-19 | O | CH(CH3)CCH | H | H |
| U-20 | O | PhCH2 | H | H |
| U-21 | O | Ph(CH3)CH | H | H |
| U-22 | O | Ph(CH3)2C | H | H |
| U-23 | O | Ph | H | H |
| U-24 | O | 2-Cl—Ph | H | H |
| U-25 | O | 3-Cl—Ph | H | H |
| U-26 | O | 4-Cl—Ph | H | H |
| U-27 | S | H | H | H |
| U-28 | S | n-C3H7 | H | H |
| U-29 | S | iso-C3H7 | H | H |
| U-30 | S | n-C4H9 | H | H |
| U-31 | S | iso-C4H9 | H | H |
| U-32 | S | sec-C4H9 | H | H |
| U-33 | S | tert-C4H9 | H | H |
| U-34 | S | n-C5H11 | H | H |
| U-35 | S | n-C6H13 | H | H |
| U-36 | S | cyclo-C3H5 | H | H |
| U-37 | S | cyclo-C5H9 | H | H |
| U-38 | S | cyclo-C6H11 | H | H |
| U-39 | S | CH2CH=CH2 | H | H |
| U-40 | S | CH2C(CH3)=CH2 | H | H |
| U-41 | S | CH(CH3)CH=CH2 | H | H |
| U-42 | S | CH2CH=CHCH3 | H | H |
| U-43 | S | CH2CCH | H | H |
| U-44 | S | CH2CCCH3 | H | H |
| U-45 | S | CH(CH3)CCH | H | H |
| U-46 | S | PhCH2 | H | H |
| U-47 | S | Ph(CH3)CH | H | H |
| U-48 | S | Ph(CH3)2C | H | H |
| U-49 | S | Ph | H | H |
| U-50 | S | 2-Cl—Ph | H | H |
| U-51 | S | 3-Cl—Ph | H | H |
| U-52 | S | 4-Cl—Ph | H | H |

TABLE 7

Compounds of formula (ID):

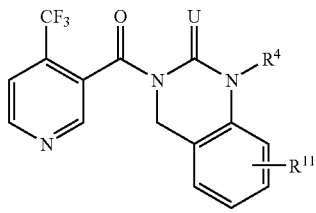

(1D)

| Compound | U | R⁴ | R¹¹ |
|---|---|---|---|
| V-1 | O | H | H |
| V-2 | O | CH3 | H |
| V-3 | O | C2H5 | H |
| V-4 | O | n-C3H7 | H |
| V-5 | O | iso-C3H7 | H |
| V-6 | O | n-C4H9 | H |
| V-7 | O | iso-C4H9 | H |
| V-8 | O | sec-C4H9 | H |
| V-9 | O | tert-C4H9 | H |
| V-10 | O | n-C5H11 | H |
| V-11 | O | n-C6H13 | H |
| V-12 | O | cyclo-C3H5 | H |
| V-13 | O | cyclo-C5H9 | H |
| V-14 | O | cyclo-C6H11 | H |
| V-15 | O | CH2CH=CH2 | H |
| V-16 | O | CH2C(CH3)=CH2 | H |
| V-17 | O | CH(CH3)CH=CH2 | H |
| V-18 | O | CH2CH=CHCH3 | H |
| V-19 | O | CH2CCH | H |
| V-20 | O | CH2CCCH3 | H |
| V-21 | O | CH(CH3)CCH | H |
| V-22 | O | PhCH2 | H |
| V-23 | O | Ph(CH3)CH | H |
| V-24 | O | Ph(CH3)2C | H |
| V-25 | O | Ph | H |
| V-26 | O | 2-Cl—Ph | H |
| V-27 | O | 3-Cl—Ph | H |
| V-28 | O | 4-Cl—Ph | H |
| V-29 | S | H | H |
| V-30 | S | CH3 | H |
| V-31 | S | C2H5 | H |
| V-32 | S | n-C3H7 | H |
| V-33 | S | iso-C3H7 | H |
| V-34 | S | n-C4H9 | H |
| V-35 | S | iso-C4H9 | H |
| V-36 | S | sec-C4H9 | H |
| V-37 | S | tert-C4H9 | H |
| V-38 | S | n-C5H11 | H |
| V-39 | S | n-C6H13 | H |
| V-40 | S | cyclo-C3H5 | H |
| V-41 | S | cyclo-C5H9 | H |
| V-42 | S | cyclo-C6H11 | H |
| V-43 | S | CH2CH=CH2 | H |
| V-44 | S | CH2C(CH3)=CH2 | H |
| V-45 | S | CH(CH3)CH=CH2 | H |
| V-46 | S | CH2CH=CHCH3 | H |
| V-47 | S | CH2CCH | H |
| V-48 | S | CH2CCCH3 | H |
| V-49 | S | CH(CH3)CCH | H |
| V-50 | S | PhCH2 | H |
| V-51 | S | Ph(CH3)CH | H |
| V-52 | S | Ph(CH3)2C | H |
| V-53 | S | Ph | H |
| V-54 | S | 2-Cl—Ph | H |
| V-55 | S | 3-Cl—Ph | H |
| V-56 | S | 4-Cl—Ph | H |

TABLE 8

Compounds of formula (I) wherein R¹ is —C(=U)NR³R⁴, U is NR¹⁸ and m is zero.

| Compound | R³ | R⁴ | R² | R¹⁸ |
|---|---|---|---|---|
| W-1 | CH3 | H | H | H |
| W-2 | C2H5 | H | H | H |
| W-3 | n-C3H7 | H | H | H |
| W-4 | iso-C3H7 | H | H | H |
| W-5 | n-C4H9 | H | H | H |
| W-6 | iso-C4H9 | H | H | H |
| W-7 | tert-C4H9 | H | H | H |
| W-8 | n-C5H11 | H | H | H |
| W-9 | (CH3)3CCH2 | H | H | H |
| W-10 | n-C6H13 | H | H | H |
| W-11 | CH2=CHCH2 | H | H | H |
| W-12 | CHCCH2 | H | H | H |
| W-13 | cyclo-C3H5 | H | H | H |
| W-14 | cyclo-C5H9 | H | H | H |
| W-15 | cyclo-C6H11 | H | H | H |
| W-16 | PhCH2 | H | H | H |
| W-17 | PhCH(CH3) | H | H | H |
| W-18 | CH3NH | H | H | H |
| W-19 | C2H5NH | H | H | H |
| W-20 | n-C3H7NH | H | H | H |
| W-21 | iso-C3H7NH | H | H | H |
| W-22 | n-C4H9NH | H | H | H |
| W-23 | tert-C4H9NH | H | H | H |
| W-24 | n-C5H11NH | H | H | H |
| W-25 | n-C6H13NH | H | H | H |
| W-26 | PhCH2NH | H | H | H |
| W-27 | PhNH | H | H | H |
| W-28 | Ph | H | H | H |
| W-29 | 2-F—Ph | H | H | H |
| W-30 | 3-F—Ph | H | H | H |
| W-31 | 4-F—Ph | H | H | H |
| W-32 | 2-Cl—Ph | H | H | H |
| W-33 | 3-Cl—Ph | H | H | H |
| W-34 | 4-Cl—Ph | H | H | H |
| W-35 | 2-CF3—Ph | H | H | H |
| W-36 | 3-CF3—Ph | H | H | H |
| W-37 | 4-CF3—Ph | H | H | H |
| W-38 | 2-CH3—Ph | H | H | H |
| W-39 | 3-CH3—Ph | H | H | H |
| W-40 | 4-CH3—Ph | H | H | H |
| W-41 | 2-CH3O—Ph | H | H | H |
| W-42 | 3-CH3O—Ph | H | H | H |
| W-43 | 4-CH3O—Ph | H | H | H |
| W-44 | CF3CH2 | H | H | H |
| W-45 | ClCH2CH2 | H | H | H |
| W-46 | ClCH2CH2CH2 | H | H | H |
| W-47 | CH3OCH2CH2 | H | H | H |
| W-48 | CH3CH2OCH2CH2 | H | H | H |
| W-49 | CH3OCH2CH2CH2 | H | H | H |
| W-50 | C2H5OCH2CH2CH2 | H | H | H |
| W-51 | n-C4H9OCH2CH2CH2 | H | H | H |
| W-52 | CH3OCH(CH3)CH2CH2 | H | H | H |
| W-53 | (CH3O)2CHCH2 | H | H | H |
| W-54 | HOCH2CH2 | H | H | H |
| W-55 | HOCH2CH2CH2 | H | H | H |
| W-56 | CH3SCH2CH2 | H | H | H |
| W-57 | CH3CH2SCH2CH2 | H | H | H |
| W-58 | CH3SCH2CH2CH2 | H | H | H |
| W-59 | C2H5SCH2CH2CH2 | H | H | H |
| W-60 | CH2CH2CH2CH2 | | H | H |
| W-61 | CH2CH2CH2CH2CH2 | | H | H |
| W-62 | CH2CH2OCH2CH2 | | H | H |
| W-63 | CH2CH2SCH2CH2 | | H | H |
| W-64 | CH2CH2NHCH2CH2 | | H | H |
| W-65 | CH2CH2N(CH3)CH2CH2 | | H | H |
| W-66 | N=CHCH2CH2 | | H | H |
| W-67 | N=CHCH=CH | | H | H |
| W-68 | CH3 | CH3 | H | H |
| W-69 | C2H5 | CH3 | H | H |
| W-70 | n-C3H7 | CH3 | H | H |
| W-71 | iso-C3H7 | CH3 | H | H |
| W-72 | n-C4H9 | CH3 | H | H |
| W-73 | iso-C4H9 | CH3 | H | H |
| W-74 | tert-C4H9 | CH3 | H | H |

TABLE 8-continued

Compounds of formula (I) wherein $R^1$ is —C(=U)NR$^3$R$^4$, U is NR$^{18}$ and m is zero.

| Compound | R$^3$ | R$^4$ | R$^2$ | R$^{18}$ |
|---|---|---|---|---|
| W-75 | n-C5H11 | CH3 | H | H |
| W-76 | n-C6H13 | CH3 | H | H |
| W-77 | CH2=CHCH2 | CH3 | H | H |
| W-78 | CHCCH2 | CH3 | H | H |
| W-79 | cyclo-C3H5 | CH3 | H | H |
| W-80 | cyclo-C5H9 | CH3 | H | H |
| W-81 | cyclo-C6H11 | CH3 | H | H |
| W-82 | PhCH2 | CH3 | H | H |
| W-83 | CH3NH | CH3 | H | H |
| W-84 | C2H5NH | CH3 | H | H |
| W-85 | n-C3H7NH | CH3 | H | H |
| W-86 | iso-C3H7NH | CH3 | H | H |
| W-87 | n-C4H9NH | CH3 | H | H |
| W-88 | tert-C4H9NH | CH3 | H | H |
| W-89 | n-C5H11NH | CH3 | H | H |
| W-90 | n-C6H13NH | CH3 | H | H |
| W-91 | PhCH2NH | CH3 | H | H |
| W-92 | PhNH | CH3 | H | H |
| W-93 | Ph | CH3 | H | H |
| W-94 | 2-F—Ph | CH3 | H | H |
| W-95 | 3-F—Ph | CH3 | H | H |
| W-96 | 4-F—Ph | CH3 | H | H |
| W-97 | 2-Cl—Ph | CH3 | H | H |
| W-98 | 3-Cl—Ph | CH3 | H | H |
| W-99 | 4-Cl—Ph | CH3 | H | H |
| W-100 | 2-CF3—Ph | CH3 | H | H |
| W-101 | 3-CF3—Ph | CH3 | H | H |
| W-102 | 4-CF3—Ph | CH3 | H | H |
| W-103 | 2-CH3—Ph | CH3 | H | H |
| W-104 | 3-CH3—Ph | CH3 | H | H |
| W-105 | 4-CH3—Ph | CH3 | H | H |
| W-106 | 2-CH3O—Ph | CH3 | H | H |
| W-107 | 3-CH3O—Ph | CH3 | H | H |
| W-108 | 4-CH3O—Ph | CH3 | H | H |
| W-109 | CF3CH2 | CH3 | H | H |
| W-110 | ClCH2CH2 | CH3 | H | H |
| W-111 | ClCH2CH2CH2 | CH3 | H | H |
| W-112 | CH3OCH2CH2 | CH3 | H | H |
| W-113 | CH3CH2OCH2CH2 | CH3 | H | H |
| W-114 | CH3OCH2CH2CH2 | CH3 | H | H |
| W-115 | C2H5OCH2CH2CH2 | CH3 | H | H |
| W-116 | n-C4H9OCH2CH2CH2 | CH3 | H | H |
| W-117 | CH3OCH(CH3)CH2CH2 | CH3 | H | H |
| W-118 | (CH3O)2CHCH2 | CH3 | H | H |
| W-119 | HOCH2CH2 | CH3 | H | H |
| W-120 | HOCH2CH2CH2 | CH3 | H | H |
| W-121 | CH3 | C2H5 | H | H |
| W-122 | C2H5 | C2H5 | H | H |
| W-123 | n-C3H7 | C2H5 | H | H |
| W-124 | iso-C3H7 | C2H5 | H | H |
| W-125 | CH2=CHCH2 | C2H5 | H | H |
| W-126 | CHCCH2 | C2H5 | H | H |
| W-127 | cyclo-C3H5 | C2H5 | H | H |
| W-128 | PhCH2 | C2H5 | H | H |
| W-129 | CH3NH | C2H5 | H | H |
| W-130 | C2H5NH | C2H5 | H | H |
| W-131 | PhCH2NH | C2H5 | H | H |
| W-132 | PhNH | C2H5 | H | H |
| W-133 | Ph | C2H5 | H | H |
| W-134 | 2-Cl—Ph | C2H5 | H | H |
| W-135 | 3-Cl—Ph | C2H5 | H | H |
| W-136 | 4-Cl—Ph | C2H5 | H | H |
| W-137 | 2-CF3—Ph | C2H5 | H | H |
| W-138 | 3-CF3—Ph | C2H5 | H | H |
| W-139 | 4-CF3—Ph | C2H5 | H | H |
| W-140 | 2-CH3O—Ph | C2H5 | H | H |
| W-141 | 3-CH3O—Ph | C2H5 | H | H |
| W-142 | 4-CH3O—Ph | C2H5 | H | H |
| W-143 | CF3CH2 | C2H5 | H | H |
| W-144 | ClCH2CH2 | C2H5 | H | H |
| W-145 | ClCH2CH2CH2 | C2H5 | H | H |
| W-146 | CH3OCH2CH2 | C2H5 | H | H |
| W-147 | CH3CH2OCH2CH2 | C2H5 | H | H |
| W-148 | CH3OCH2CH2CH2 | C2H5 | H | H |
| W-149 | C2H5OCH2CH2CH2 | C2H5 | H | H |
| W-150 | n-C4H9OCH2CH2CH2 | C2H5 | H | H |
| W-151 | CH3OCH(CH3)CH2CH2 | C2H5 | H | H |
| W-152 | (CH3O)2CHCH2 | C2H5 | H | H |
| W-153 | HOCH2CH2 | C2H5 | H | H |
| W-154 | HOCH2CH2CH2 | C2H5 | H | H |
| W-155 | CH3 | H | H | CH3 |
| W-156 | C2H5 | H | H | CH3 |
| W-157 | n-C3H7 | H | H | CH3 |
| W-158 | iso-C3H7 | H | H | CH3 |
| W-159 | tert-C4H9 | H | H | CH3 |
| W-160 | CH2=CHCH2 | H | H | CH3 |
| W-161 | CHCCH2 | H | H | CH3 |
| W-162 | cyclo-C3H5 | H | H | CH3 |
| W-163 | PhCH2 | H | H | CH3 |
| W-164 | CH3NH | H | H | CH3 |
| W-165 | C2H5NH | H | H | CH3 |
| W-166 | n-C3H7NH | H | H | CH3 |
| W-167 | iso-C3H7NH | H | H | CH3 |
| W-168 | PhCH2NH | H | H | CH3 |
| W-169 | PhNH | H | H | CH3 |
| W-170 | Ph | H | H | CH3 |
| W-171 | 2-Cl—Ph | H | H | CH3 |
| W-172 | 3-Cl—Ph | H | H | CH3 |
| W-173 | 4-Cl—Ph | H | H | CH3 |
| W-174 | CH3OCH2CH2 | H | H | CH3 |
| W-175 | CH3CH2OCH2CH2 | H | H | CH3 |
| W-176 | CH3OCH2CH2CH2 | H | H | CH3 |
| W-177 | C2H5OCH2CH2CH2 | H | H | CH3 |
| W-178 | n-C4H9OCH2CH2CH2 | H | H | CH3 |
| W-179 | CH3OCH(CH3)CH2CH2 | H | H | CH3 |
| W-180 | (CH3O)2CHCH2 | H | H | CH3 |
| W-181 | HOCH2CH2 | H | H | CH3 |
| W-182 | HOCH2CH2CH2 | H | H | CH3 |
| W-183 | CH2CH2CH2CH2 | | H | CH3 |
| W-184 | CH2CH2CH2CH2CH2 | | H | CH3 |
| W-185 | CH2CH2OCH2CH2 | | H | CH3 |
| W-186 | CH2CH2SCH2CH2 | | H | CH3 |
| W-187 | CH2CH2NHCH2CH2 | | H | CH3 |
| W-188 | CH2CH2N(CH3)CH2CH2 | | H | CH3 |
| W-189 | N=CHCH2CH2 | | H | CH3 |
| W-190 | CH3 | H | H | tert-C4H9 |
| W-191 | C2H5 | H | H | tert-C4H9 |
| W-192 | n-C3H7 | H | H | tert-C4H9 |
| W-193 | iso-C3H7 | H | H | tert-C4H9 |
| W-194 | tert-C4H9 | H | H | tert-C4H9 |
| W-195 | CH2=CHCH2 | H | H | tert-C4H9 |
| W-196 | CHCCH2 | H | H | tert-C4H9 |
| W-197 | cyclo-C3H5 | H | H | tert-C4H9 |
| W-198 | PhCH2 | H | H | tert-C4H9 |
| W-199 | CH3NH | H | H | tert-C4H9 |
| W-200 | PhCH2NH | H | H | tert-C4H9 |
| W-201 | PhNH | H | H | tert-C4H9 |
| W-202 | Ph | H | H | tert-C4H9 |
| W-203 | 2-Cl—Ph | H | H | tert-C4H9 |
| W-204 | 3-Cl—Ph | H | H | tert-C4H9 |
| W-205 | 4-Cl—Ph | H | H | tert-C4H9 |
| W-206 | CH3OCH2CH2 | H | H | tert-C4H9 |
| W-207 | CH3CH2OCH2CH2 | H | H | tert-C4H9 |
| W-208 | CH3OCH2CH2CH2 | H | H | tert-C4H9 |
| W-209 | C2H5OCH2CH2CH2 | H | H | tert-C4H9 |
| W-210 | (CH3O)2CHCH2 | H | H | tert-C4H9 |
| W-211 | HOCH2CH2 | H | H | tert-C4H9 |
| W-212 | HOCH2CH2CH2 | H | H | tert-C4H9 |
| W-213 | CH2CH2CH2CH2 | | H | tert-C4H9 |
| W-214 | CH2CH2CH2CH2CH2 | | H | tert-C4H9 |
| W-215 | CH2CH2OCH2CH2 | | H | tert-C4H9 |
| W-216 | CH2CH2SCH2CH2 | | H | tert-C4H9 |
| W-217 | CH2CH2NHCH2CH2 | | H | tert-C4H9 |
| W-218 | CH2CH2N(CH3)CH2CH2 | | H | tert-C4H9 |
| W-219 | N=CHCH2CH2 | | H | tert-C4H9 |
| W-220 | CH3 | H | H | OH |
| W-221 | C2H5 | H | H | OH |
| W-222 | n-C3H7 | H | H | OH |

TABLE 8-continued

Compounds of formula (I) wherein $R^1$ is —C(=U)NR$^3$R$^4$, U is NR$^{18}$ and m is zero.

| Compound | R$^3$ | R$^4$ | R$^2$ | R$^{18}$ |
|---|---|---|---|---|
| W-223 | iso-C3H7 | H | H | OH |
| W-224 | tert-C4H9 | H | H | OH |
| W-225 | CH2=CHCH2 | H | H | OH |
| W-226 | CHCCH2 | H | H | OH |
| W-227 | cyclo-C3H5 | H | H | OH |
| W-228 | PhCH2 | H | H | OH |
| W-229 | CH3NH | H | H | OH |
| W-230 | C2H5NH | H | H | OH |
| W-231 | PhCH2NH | H | H | OH |
| W-232 | PhNH | H | H | OH |
| W-233 | Ph | H | H | OH |
| W-234 | 2-Cl—Ph | H | H | OH |
| W-235 | 3-Cl—Ph | H | H | OH |
| W-236 | 4-Cl—Ph | H | H | OH |
| W-237 | CH3OCH2CH2 | H | H | OH |
| W-238 | CH3CH2OCH2CH2 | H | H | OH |
| W-239 | CH3OCH2CH2CH2 | H | H | OH |
| W-240 | C2H5OCH2CH2CH2 | H | H | OH |
| W-241 | n-C4H9OCH2CH2CH2 | H | H | OH |
| W-242 | CH3OCH(CH3)CH2CH2 | H | H | OH |
| W-243 | (CH3O)2CHCH2 | H | H | OH |
| W-244 | HOCH2CH2 | H | H | OH |
| W-245 | HOCH2CH2CH2 | H | H | OH |
| W-246 | CH2CH2CH2CH2 | | H | OH |
| W-247 | CH2CH2CH2CH2CH2 | | H | OH |
| W-248 | CH2CH2OCH2CH2 | | H | OH |
| W-249 | CH2CH2SCH2CH2 | | H | OH |
| W-250 | CH2CH2NHCH2CH2 | | H | OH |
| W-251 | CH2CH2N(CH3)CH2CH2 | | H | OH |
| W-252 | N=CHCH2CH2 | | H | OH |
| W-253 | N=CHCH=CH | | H | OH |
| W-254 | CH3 | H | H | CH3O |
| W-255 | C2H5 | H | H | CH3O |
| W-256 | n-C3H7 | H | H | CH3O |
| W-257 | iso-C3H7 | H | H | CH3O |
| W-258 | tert-C4H9 | H | H | CH3O |
| W-259 | CH2=CHCH2 | H | H | CH3O |
| W-260 | CHCCH2 | H | H | CH3O |
| W-261 | cyclo-C3H5 | H | H | CH3O |
| W-262 | PhCH2 | H | H | CH3O |
| W-263 | CH3NH | H | H | CH3O |
| W-264 | C2H5NH | H | H | CH3O |
| W-265 | PhCH2NH | H | H | CH3O |
| W-266 | PhNH | H | H | CH3O |
| W-267 | Ph | H | H | CH3O |
| W-268 | 2-Cl—Ph | H | H | CH3O |
| W-269 | 3-Cl—Ph | H | H | CH3O |
| W-270 | 4-Cl—Ph | H | H | CH3O |
| W-271 | CH3OCH2CH2 | H | H | CH3O |
| W-272 | CH3CH2OCH2CH2 | H | H | CH3O |
| W-273 | CH3OCH2CH2CH2 | H | H | CH3O |
| W-274 | C2H5OCH2CH2CH2 | H | H | CH3O |
| W-275 | n-C4H9OCH2CH2CH2 | H | H | CH3O |
| W-276 | CH3OCH(CH3)CH2CH2 | H | H | CH3O |
| W-277 | (CH3O)2CHCH2 | H | H | CH3O |
| W-278 | HOCH2CH2 | H | H | CH3O |
| W-279 | HOCH2CH2CH2 | H | H | CH3O |
| W-280 | CH3SCH2CH2 | H | H | CH3O |
| W-281 | CH3CH2SCH2CH2 | H | H | CH3O |
| W-282 | CH3SCH2CH2CH2 | H | H | CH3O |
| W-283 | C2H5SCH2CH2CH2 | H | H | CH3O |

TABLE 9

Compounds of formula (I) wherein $R^1$ is —C(=V)OR$^{3a}$ and m is zero.

| Compound | V | R$^{3a}$ | R$^2$ |
|---|---|---|---|
| X-1 | O | cyclo-C3H5 | H |
| X-2 | O | cyclo-C5H9 | H |
| X-3 | O | cyclo-C6H11 | H |
| X-4 | O | CH3NH | H |
| X-5 | O | C2H5NH | H |
| X-6 | O | n-C3H7NH | H |
| X-7 | O | iso-C3H7NH | H |
| X-8 | O | n-C4H9NH | H |
| X-9 | O | tert-C4H9NH | H |
| X-10 | O | n-C5H11NH | H |
| X-11 | O | n-C6H13NH | H |
| X-12 | O | PhCH2NH | H |
| X-13 | O | PhNH | H |
| X-14 | O | CF3CH2 | H |
| X-15 | O | ClCH2CH2 | H |
| X-16 | O | ClCH2CH2CH2 | H |
| X-17 | O | CH3OCH2CH2 | H |
| X-18 | O | CH3CH2OCH2CH2 | H |
| X-19 | O | CH3OCH2CH2CH2 | H |
| X-20 | O | C2H5OCH2CH2CH2 | H |
| X-21 | O | n-C4H9OCH2CH2CH2 | H |
| X-22 | O | CH3OCH(CH3)CH2CH2 | H |
| X-23 | O | (CH3O)2CHCH2 | H |
| X-24 | O | HOCH2CH2 | H |
| X-25 | O | HOCH2CH2CH2 | H |
| X-26 | O | CH3SCH2CH2 | H |
| X-27 | O | CH3CH2SCH2CH2 | H |
| X-28 | O | CH3SCH2CH2CH2 | H |
| X-29 | O | C2H5SCH2CH2CH2 | H |
| X-30 | O | CH3(cyclo-C3H5)CH | H |
| X-31 | O | NCCH2CH2 | H |
| X-32 | S | cyclo-C3H5 | H |
| X-33 | S | cyclo-C5H9 | H |
| X-34 | S | cyclo-C6H11 | H |
| X-35 | S | CH3NH | H |
| X-36 | S | C2H5NH | H |
| X-37 | S | n-C3H7NH | H |
| X-38 | S | iso-C3H7NH | H |
| X-39 | S | n-C4H9NH | H |
| X-40 | S | tert-C4H9NH | H |
| X-41 | S | n-C5H11NH | H |
| X-42 | S | n-C6H13NH | H |
| X-43 | S | PhCH2NH | H |
| X-44 | S | PhNH | H |
| X-45 | S | CF3CH2 | H |
| X-46 | S | ClCH2CH2 | H |
| X-47 | S | ClCH2CH2CH2 | H |
| X-48 | S | CH3OCH2CH2 | H |
| X-49 | S | CH3CH2OCH2CH2 | H |
| X-50 | S | CH3OCH2CH2CH2 | H |
| X-51 | S | C2H5OCH2CH2CH2 | H |
| X-52 | S | n-C4H9OCH2CH2CH2 | H |
| X-53 | S | CH3OCH(CH3)CH2CH2 | H |
| X-54 | S | (CH3O)2CHCH2 | H |
| X-55 | S | HOCH2CH2 | H |
| X-56 | S | HOCH2CH2CH2 | H |
| X-57 | S | CH3SCH2CH2 | H |
| X-58 | S | CH3CH2SCH2CH2 | H |
| X-59 | S | CH3SCH2CH2CH2 | H |
| X-60 | S | C2H5SCH2CH2CH2 | H |
| X-61 | S | CH3(cyclo-C3H5)CH | H |
| X-62 | S | NCCH2CH2 | H |
| X-63 | O | cyclo-C3H5 | CH3 |
| X-64 | O | cyclo-C5H9 | CH3 |
| X-65 | O | cyclo-C6H11 | CH3 |
| X-66 | O | CH3NH | CH3 |
| X-67 | O | C2H5NH | CH3 |
| X-68 | O | n-C3H7NH | CH3 |
| X-69 | O | iso-C3H7NH | CH3 |
| X-70 | O | n-C4H9NH | CH3 |
| X-71 | O | tert-C4H9NH | CH3 |
| X-72 | O | n-C5H11NH | CH3 |
| X-73 | O | n-C6H13NH | CH3 |
| X-74 | O | PhCH2NH | CH3 |
| X-75 | O | PhNH | CH3 |
| X-76 | O | CF3CH2 | CH3 |
| X-77 | O | ClCH2CH2 | CH3 |
| X-78 | O | ClCH2CH2CH2 | CH3 |

TABLE 9-continued

Compounds of formula (I) wherein $R^1$ is —C(=V)$OR^{3a}$ and m is zero.

| Compound | V | $R^{3a}$ | $R^2$ |
|---|---|---|---|
| X-79 | O | CH3OCH2CH2 | CH3 |
| X-80 | O | CH3CH2OCH2CH2 | CH3 |
| X-81 | O | CH3OCH2CH2CH2 | CH3 |
| X-82 | O | C2H5OCH2CH2CH2 | CH3 |
| X-83 | O | n-C4H9OCH2CH2CH2 | CH3 |
| X-84 | O | CH3OCH(CH3)CH2CH2 | CH3 |
| X-85 | O | (CH3O)2CHCH2 | CH3 |
| X-86 | O | HOCH2CH2 | CH3 |
| X-87 | O | HOCH2CH2CH2 | CH3 |
| X-88 | O | CH3SCH2CH2 | CH3 |
| X-89 | O | CH3CH2SCH2CH2 | CH3 |
| X-90 | O | CH3SCH2CH2CH2 | CH3 |
| X-91 | O | C2H5SCH2CH2CH2 | CH3 |
| X-92 | O | CH3(cyclo-C3H5)CH | CH3 |
| X-93 | O | NCCH2CH2 | CH3 |
| X-94 | S | cyclo-C3H5 | CH3 |
| X-95 | S | cyclo-C5H9 | CH3 |
| X-96 | S | cyclo-C6H11 | CH3 |
| X-97 | S | CH3NH | CH3 |
| X-98 | S | C2H5NH | CH3 |
| X-99 | S | n-C3H7NH | CH3 |
| X-100 | S | iso-C3H7NH | CH3 |
| X-101 | S | n-C4H9NH | CH3 |
| X-102 | S | tert-C4H9NH | CH3 |
| X-103 | S | n-C5H11NH | CH3 |
| X-104 | S | n-C6H13NH | CH3 |
| X-105 | S | PhCH2NH | CH3 |
| X-106 | S | PhNH | CH3 |
| X-107 | S | CF3CH2 | CH3 |
| X-108 | S | ClCH2CH2 | CH3 |
| X-109 | S | ClCH2CH2CH2 | CH3 |
| X-110 | S | CH3OCH2CH2 | CH3 |
| X-111 | S | CH3CH2OCH2CH2 | CH3 |
| X-112 | S | CH3OCH2CH2CH2 | CH3 |
| X-113 | S | C2H5OCH2CH2CH2 | CH3 |
| X-114 | S | n-C4H9OCH2CH2CH2 | CH3 |
| X-115 | S | CH3OCH(CH3)CH2CH2 | CH3 |
| X-116 | S | (CH3O)2CHCH2 | CH3 |
| X-117 | S | HOCH2CH2 | CH3 |
| X-118 | S | HOCH2CH2CH2 | CH3 |
| X-119 | S | CH3SCH2CH2 | CH3 |
| X-120 | S | CH3CH2SCH2CH2 | CH3 |
| X-121 | S | CH3SCH2CH2CH2 | CH3 |
| X-122 | S | C2H5SCH2CH2CH2 | CH3 |
| X-123 | S | CH3(cyclo-C3H5)CH | CH3 |
| X-124 | S | NCCH2CH2 | CH3 |
| X-125 | O | cyclo-C3H5 | C2H5 |
| X-126 | O | CH3NH | C2H5 |
| X-127 | O | C2H5NH | C2H5 |
| X-128 | O | n-C3H7NH | C2H5 |
| X-129 | O | iso-C3H7NH | C2H5 |
| X-130 | O | n-C4H9NH | C2H5 |
| X-131 | O | tert-C4H9NH | C2H5 |
| X-132 | O | PhCH2NH | C2H5 |
| X-133 | O | PhNH | C2H5 |
| X-134 | O | CF3CH2 | C2H5 |
| X-135 | O | ClCH2CH2 | C2H5 |
| X-136 | O | ClCH2CH2CH2 | C2H5 |
| X-137 | O | CH3OCH2CH2 | C2H5 |
| X-138 | O | CH3CH2OCH2CH2 | C2H5 |
| X-139 | O | CH3OCH2CH2CH2 | C2H5 |
| X-140 | O | C2H5OCH2CH2CH2 | C2H5 |
| X-141 | O | n-C4H9OCH2CH2CH2 | C2H5 |
| X-142 | O | CH3OCH(CH3)CH2CH2 | C2H5 |
| X-143 | O | (CH3O)2CHCH2 | C2H5 |
| X-144 | O | HOCH2CH2 | C2H5 |
| X-145 | O | HOCH2CH2CH2 | C2H5 |
| X-146 | O | CH3(cyclo-C3H5)CH | C2H5 |
| X-147 | O | NCCH2CH2 | C2H5 |
| X-148 | S | cyclo-C3H5 | C2H5 |
| X-149 | S | CH3NH | C2H5 |
| X-150 | S | C2H5NH | C2H5 |
| X-151 | S | n-C3H7NH | C2H5 |
| X-152 | S | iso-C3H7NH | C2H5 |
| X-153 | S | n-C4H9NH | C2H5 |
| X-154 | S | tert-C4H9NH | C2H5 |
| X-155 | S | PhCH2NH | C2H5 |
| X-156 | S | PhNH | C2H5 |
| X-157 | S | CF3CH2 | C2H5 |
| X-158 | S | ClCH2CH2 | C2H5 |
| X-159 | S | ClCH2CH2CH2 | C2H5 |
| X-160 | S | CH3OCH2CH2 | C2H5 |
| X-161 | S | CH3CH2OCH2CH2 | C2H5 |
| X-162 | S | CH3OCH2CH2CH2 | C2H5 |
| X-163 | S | C2H5OCH2CH2CH2 | C2H5 |
| X-164 | S | n-C4H9OCH2CH2CH2 | C2H5 |
| X-165 | S | CH3OCH(CH3)CH2CH2 | C2H5 |
| X-166 | S | (CH3O)2CHCH2 | C2H5 |
| X-167 | S | HOCH2CH2 | C2H5 |
| X-168 | S | HOCH2CH2CH2 | C2H5 |
| X-169 | S | CH3(cyclo-C3H5)CH | C2H5 |
| X-170 | S | NCCH2CH2 | C2H5 |

TABLE 10

1H-NMR spectral details for representative Examples from the above Tables.
Nmr spectra were measured in deuterochloroform unless otherwise stated.

| Cpd | 1H-NMR |
|---|---|
| A-2 | 3.7-3.9(2H, m), 5.1-5.2(2H, m), 5.7-5.9(1H, m), 7.63(1H, d), 8.46(1H, brs), 8.83(1H, d), 8.91(1H, d), 10.70(1H, brs) |
| A-18 | 2.26(1H, t), 4.02(2H, dd), 7.66(1H, d), 8.34(1H, brs), 8.91(1H, s), 8.94(1H, d), 10.03(1H, brs) |
| A-24 | 0.5-0.6(1H, m), 0.7-0.8(1H, m), 2.6-2.7(1H, m), 7.65(1H, d), 8.33(1H, brs), 8.89(1H, s), 8.93(1H, d), 9.68(1H, brs) |
| A-26 | 9.83(1H, s), 8.93(1H, d), 8.89(1H, s), 8.40(1H, d), 7.65(1H, d), 4.12(1H, dt), 2.27(2H, m), 1.98(2H, m), 1.73(2H, m) |
| A-28 | 1.4-2.0(4H, m), 3.8-4.1(1H, m), 7.64(1H, d), 8.28(1H, brd), 8.90(1H, s), 8.91(1H, d) |
| A-30 | 1.2-1.4(5H, m), 1.5-1.9(5H, m), 3.4-3.6(1H, m), 7.63(1H, d), 8.22(1H, brd), 8.89(1H, s), 8.91(1H, d) |
| A-32 | 9.68(1H, s), 8.93(1H, d), 8.90(1H, s), 8.38(1H, t), 7.65(1H, d), 3.10(2H, t), 1.00(1H, m), 0.53(2H, m), 0.22(1H, m) |
| A-37 | 4.39(2H, d), 7.1-7.4(5H, m), 7.62(1H, d), 8.69(1H, m), 8.7-9.0(3H, m) |
| A-38 | 1.48(3H, d), 4.7-4.9(1H, m), 7.1-7.4(5H, m), 7.58(1H, d), 8.78(1H, brd), 8.86(1H, s), 8.90(1H, d) |

TABLE 10-continued

1H-NMR spectral details for representative Examples from the above Tables.
Nmr spectra were measured in deuterochloroform unless otherwise stated.

| Cpd | 1H-NMR |
|---|---|
| A-39 | 2.80(2H, t), 3.42(2H, t), 7.1-7.4(5H, m), 7.62(1H, d), 8.3-8.5(1H, m), 8.89(1H, s), 8.90(1H, d) |
| A-62 | 3.80(3H, s), 4.31(1H, s), 6.86(2H, d), 7.16(2H, d), 7.62(1H, d), 8.62(1H, brs), 8.8-9.0(2H, m), 10.26(1H, s) |
| A-64 | 3.83(3H, s), 7.66(1H, d), 8.89(1H, s), 8.94(1H, d), 9.21(1H, brs), 10.60(1H, brs) |
| A-65 | 10.54(1H, s), 9.51(1H, s), 8.94(1H, d), 8.89(1H, s), 7.65(1H, d)4.01(2H, q), 1.28(3H, t) |
| A-67 | 10.39(1H), 8.90-9.05(2H), 7.81(1H), 4.18(1H), 1.24(6H) |
| A-71 | 1.35(9H, s), 7.62(1H, d), 8.66(1H, s), 8.78(1H, d) |
| A-74 | 10.58(1H, s), 10.04(1H, s), 8.92(1H, d), 8.89(1H, s), 7.65(1H, d), 5.94(1H, m), 5.38(1H, d), 5.35(1H, d), 4.39(2H, d) |
| A-75 | 10.51(1H, brs), 8.94(1H, d), 8.89(1H, s), 7.65(1H, d), 5.05(2H, S), 4.34(2H, s), 1.81(3H, s) |
| A-79 | 10.45(1H, brs), 8.96(1H, d), 8.88(1H, s), 8.52(1H, brs), 7.66(1H, d), 5.85(1H, m), 5.67(1H, m), 4.38(2H, d), 1.77(3H, d) |
| A-81 | 10.74(1H, brs), 9.37(1H, brs), 8.93(1H, d), 8.89(1H, s), 7.66(1H, d), 4.56(2H, s), 2.60(1H) |
| A-85 | 1.33(3H, t), 4.29(2H, q), 4.48(2H, s), 7.64(1H, d), 8.85(1H, s), 8.90(1H, d), 9.60(1H, brs), 11.11(1H, brs) |
| A-86 | 4.92(2H, s), 7.3-7.5(5H, m), 7.63(1H, d), 8.8-9.0(2H, m), 9.91(1H, brs), 10.56(1H, brs) |
| A-88 | 8.29(1H, d), 8.88(1H, s), 8.86(1H, s), 7.65(1H, d), 7.28(1H, t), 6.93-6.99(3H) 4.93(2H, s), 3.83(3H, s) |
| A-89 | 8.88(1H, s), 8.76(1H, d), 8.63(1H, s), 7.55(1H, d), 7.36(2H, d), 6.88(2H, d), 4.99(2H, s), 3.79(3H, s) |
| A-90 | 8.97(1H, d), 8.93(1H, d), 8.52(1H, brs), 7.67(1H, d), 7.35(2H, t), 7.11(2H, d), 7.10(1H, t) |
| A-149 | 10.32(1H, s), 9.53(1H, s), 8.98-9.01(2H), 7.68(1H, d), 7.44(2H, d), 7.33(2H, t), 7.15(1H, t) |
| A-153 | 7.0-7.1(1H, m), 7.2-7.3(1H, m), 7.3-7.5(1H, m), 7.68(1H, d), 7.9-8.1(1H, m), 8.9-9.1(2H, m), 9.82(1H, brs), 10.88(1H, brs) |
| A-154 | 7.0-7.3(3H, m), 7.51(1H, s), 7.71(1H, d), 8.99(1H, s), 9.03(1H, d), 10.21(1H, brs), 10.46(1H, brs) |
| A-155 | 7.2-7.3(2H, m), 7.4-7.5(2H, m), 7.69(1H, d), 8.94(1H, s), 8.97(1H, d), 10.26(1H, brs), 10.42(1H, brs) |
| A-158 | 7.3-7.4(2H, m), 7.4-7.5(2H, m), 7.70(1H, d), 8.99(1H, s), 9.02(1H, d), 9.30(1H, brs), 10.33(1H, brs) |
| A-162 | 7.2-7.3(1H, m), 7.5-7.6(1H, m), 7.6-7.7(2H, m), 7.93(1H, d), 8.96(1H, d), 8.98(1H, s), 9.68(1H, brs), 10.72(1H, brs) |
| A-170 | 3.82(3H, s), 6.8-6.9(2H, m), 7.3-7.5(2H, m), 7.68(1H, d), 8.9-9.0(2H, m), 9.33(1H, brs), 10.17(1H, brs) |
| A-180 | 3.99(3H, s), 7.1-7.2(1H, m), 7.4-7.6(1H, m), 7.66(1H, d), 8.0-8.1(1H, m), 8.2-8.3(1H, m), 8.97(1H, d), 9.00(1H, s), 9.39(1H, brs), 12.32(1H, brs) |
| A-190 | 10.42(1H, s), 9.11(1H, s), 9.01(1H, d), 7.86(1H, d), 7.60(1H, s), 7.53(1H, d), 7.31(1H, t), 7.11(1H, d), 4.62(2H) |
| A-194 | 7.1-7.3(2H, m), 7.4-7.5(2H, m), 7.69(1H, d), 8.9-9.0(2H, m), 9.65(1H, brs), 10.42(1H, brs) |
| A-200 | 6.9-7.1(4H, m), 7.3-7.4(2H, m), 7.4-7.5(2H, m), 7.69(1H, d), 8.9-9.0(2H, m), 9.34(1H, brs), 10.30(1H, brs) |
| A-203 | 10.38(1H, s), 9.58(1H, s), 8.98-9.01(2H), 7.71(1H, d), 7.59(2H, d), 7.49(2H, d), 7.00-7.08(4H) |
| A-204 | 7.2-7.4(2H, m), 7.70(1H, d), 8.1-8.2(1H, m), 8.79(1H, brs), 8.9-9.1(2H, m), 10.92(1H, brs) |
| A-205 | 7.0-7.1(1H, m), 7.3-7.4(1H, m), 7.71(1H, d), 7.9-8.0(1H, m), 8.99(1H, s), 9.03(1H, d), 10.08(1H, bes), 11.05(1H, brs) |
| A-206 | 7.2-7.3(2H, m), 7.3-7.4(2H, m), 7.65(1H, d), 8.92(1H, d), 8.95(1H, s), 9.36(1H, brs), 9.92(1H, brs) |
| A-207 | 7.1-7.2(1H, m), 7.3-7.4(1H, m), 7.6-7.7(1H, m), 7.72(1H, d), 8.99(1H, s), 9.03(1H, d), 10.21(1H, brs), 10.50(1H, brs) |
| A-208 | 7.1-7.2(1H, m), 7.4-7.5(2H, m), 7.72(1H, d), 8.97(1H, s), 9.03(1H, d), 9.13(1H, brs), 10.45(1H, brs) |
| A-209 | 9.07(1H, s), 8.97(1H, d), 8.27(1H, d), 8.00(1H, brs), 7.81(1H, d), 7.74(1H, t), 7.09(1H, t) |
| A-210 | 10.44(1H, s), 9.33(1H, brs), 9.02(1H, d), 8.99(1H, s), 8.71(1H, S), 8.40(1H, d), 7.98(1H, d), 7.71(1H, d), 7.32(1H, dd) |
| A-211 | 10.57(1H, s), 9.12(1H, s), 9.02(1H, d), 8.48(2H, d), 7.87(1H, d), 7.63(2H, d) |
| A-212 | 12.48(1H, brs), 9.63(1H, brs), 8.88(1H, d), 8.81(1H, s), 8.65(2H, d), 7.61(1H, d), 7.07(1H, t) |
| A-222 | 7.01(1H, d), 7.48(1H, d), 7.71(1H, d), 8.98(1H, s), 9.01(1H, d), 9.92(1H, brs) |
| A-223 | 7.72(1H, d), 8.33(1H, s), 8.87(1H, s), 8.98(1H, s), 9.01(1H, d), 10.18(1H, brs) |

TABLE 10-continued

1H-NMR spectral details for representative Examples from the above Tables.
Nmr spectra were measured in deuterochloroform unless otherwise stated.

| Cpd | 1H-NMR |
|---|---|
| A-248 | 3.8-4.0(2H, m), 7.67(1H, d), 8.6-8.8(1H, m), 8.91(1H, s), 8.96(1H, s), 9.80(1H, brs) |
| A-250 | 1.9-2.1(2H, m), 3.3-3.5(2H, m), 3.5-3.7(2H, m), 7.65(1H, d), 8.43(1H, brs), 8.90(1H, s), 8.93(1H, d), 10.35(1H, brs) |
| A-251 | 3.39(3H, s), 3.4-3.6(4H, m), 7.65(1H, d), 8.43(1H, brs), 8.90(1H, s), 8.94(1H, d), 9.02(1H, brs) |
| A-255 | 0.92(3H, t), 1.3-1.5(2H, m), 1.5-1.7(2H, m), 1.7-1.9(2H, m), 3.2-3.6(6H, m), 7.63(1H, d), 8.45(1H, brs), 8.89(1H, s), 8.91(1H, d), 10.00(1H, brs) |
| A-256 | 3.3-3.6(m, 8H), 4.44(1H, t), 7.65(1H, d), 8.40(1H, brs), 8.90(1H, s), 8.93(1H, s), 9.40(1H, brs) |
| A-260 | 3.4-3.5(2H, m), 3.7-3.9(2H, m), 7.67(1H, d), 8.58(1H, brs), 8.91(1H, s), 8.95(1H, d), 9.22(1H, brs) |
| A-261 | 10.89(1H, s), 8.89-8.93(2H), 8.55(1h, d), 7.66(1H, d), 3.32-3.64(4H), 1.71-1.76(2H) |
| A-262 | 3.78(3H, s), 3.98(2H, d), 7.64(1H, d), 8.7-8.9(1H, m), 8.89(1H, s), 8.92(1H, d), 10.31(1H, brs) |
| A-265 | 4.43(2H, d), 7.84(1H, d), 8.81(1H, brs), 9.00(1H, d), 9.08(1H, s) |
| A-267 | 8.97(1H, d), 8.93(1H, s), 8.60(1H, s), 7.67(1H, d), 1.74(6H, s) |
| A-268 | 1.0-1.2(6H, m), 1.61(3H, s), 2.1-2.3(1H, m), 7.66(1H, d), 8.73(1H, brs), 8.94(1H, s), 8.96(1H, d), 10.05(1H, brs) |
| A-274 | 1.5-1.7(4H, m), 2.3-2.6(6H, m), 3.2-3.4(2H, m), 7.62(1H, d), 8.5-8.7(1H, m), 8.8-9.0(2H, m), 10.40(1H, brs) |
| A-292 | 1.0-1.9(10H, m), 2.88(3H, s), 3.7-4.0(1H, m), 7.55(1H, d), 8.74(1H, s), 8.82(1H, d) |
| A-296 | 2.98(3H, s), 4.52(2H, s), 7.2-7.4(5H, m), 7.57(1H, d), 8.52(1H, brs), 8.74(1H, s), 8.34(1H, d) |
| A-312 | 3.11(3H, s), 7.73(1H, d), 8.74(1H, s), 8.87(1H, s), 9.39(1H, s), 9.79(1H, brs) |
| A-313 | 3.13(3H, s), 3.79(3H, s), 7.57(1H, d), 8.72(1H, s), 8.85(1H, d), 8.90(1H, brs) |
| A-316 | 1.32(6H, d), 3.12(3H, s), 4.1-4.3(1H, m), 7.56(1H, d), 8.70(1H, s), 8.78(1H, brs), 8.84(1H, d) |
| A-317 | 3.17(3H, s), 4.40(2H, d), 5.3-5.6(2H, m), 5.9-6.1(1H, m), 7.57(1H, d), 8.68(1H, s), 8.84(1H, d) |
| A-326 | 1.50(1H, s), 3.09(3H, s), 3.83(3H, s), 5.54(1H, q), 7.58(1H, d), 8.78(1H, s), 8.85(1H, d) |
| A-329 | 3.13(3H, s), 4.88(2H, s), 7.3-7.5(5H, m), 7.53(1H, d), 8.43(1H, s), 8.59(1H, brs), 8.82(1H, d) |
| A-331 | 3.17(3H, s), 7.81(1H, d), 8.96(1H, d), 9.13(1H, s), 10.22(1H, brs) |
| A-349 | 8.84(1H, d), 8.69(1H, s), 7.69(1H, brs), 7.50-7.59(4H), 7.29(2H, d), 3.21(3H, s) |
| A-353 | 8.84(1H, d), 8.70(1H, s), 7.55-7.62(2H), 7.24-7.46(3H), 3.16(3H, s) |
| A-354 | 8.84(1H, d), 8.70(1H, s), 7.57(1H, d), 7.45-7.48(2H), 7.32(1H), 7.20(1H), 3.21(3H, s) |
| A-355 | 8.84(1H, d), 8.69(1H, s), 7.57(1H, s), 7.50(2H, d), 7.24(2H, d), 3.20(3H, s) |
| A-365 | 8.84(1H, d), 8.67(1H, s), 7.55-7.58(2H), 7.27-7.39(2H), 7.22(1H, d), 3.13(3H, s), 2.30(3H, s) |
| A-366 | 8.82(1H, d), 8.67(1H, s), 7.77(1H, s), 7.56(1H, d), 7.38(1H, t), 7.23(1H, d)7.06-7.10(2H), 3.18(3H, s), 2.41(3H, s) |
| A-367 | 8.84(1H, d), 8.68(1H, s), 7.61(1H, s), 7.56(1H, d), 7.30(2H, d), 7.16(2H, d), 3.18(3H, s), 2.42(3H, s) |
| A-369 | 8.80(1H, d)8.66(1H, s), 7.91(1H, s), 7.55(1H, d), 7.39(1H, t), 6.93(1H, dd), 6.86(1H, d), 6.79(1H, d), 3.83(3H, s), 3.19(3H, s) |
| A-373 | 8.89(1H, d), 8.85(1H, s), 8.29(2H, d), 7.80(1H, d), 7.73(2H, d), 3.41(3H, s) |
| A-381 | 8.86(1H, d), 8.73(1H, s), 7.73(1H, d) 7.29(1H, t), 6.83-6.92(3H), 3.19(3H, s) |
| A-398 | 13.93(1H, s), 8.84(1H, d), 8.75(1H, s), 8.37(1H, d), 7.83(1H, t), 7.58(1H, d), 7.09-7.16(2H), 3.36(3H, s) |
| A-431 | 3.51(2H, t), 3.64(2H, t), 7.59(1H, d), 8.78(1H, s), 8.82(1H, d), 10.38(1H, brs) |
| A-519 | 1.11(3H, t), 3.2-3.4(2H, m), 3.4-3.6(2H, m), 3.7-3.9(2H, m), 7.56(1H, d), 8.73(1H, s), 8.80(1H, d) |
| A-524 | 0.85(3H, t), 1.4-1.7(2H, m), 3.1-3.3(2H, m), 3.4-3.6(2H, m), 3.7-3.9(2H, m), 4.82(1H, brs), 7.56(1H, d), 8.72(1H, s), 8.78(1H, d), 10.54(1H, brs) |
| A-529 | 8.82(1H, d), 8.62(1H, s), 8.73(1H, brs), 7.54(1H, d), 7.25-7.60(5H), 4.40-4.58(3H), 1.16(6H) |
| A-540 | 1.16(6H, d), 4.2-4.5(1H, m), 7.63(1H, d), 8.68(1H, s), 8.82(1H, d), 9.02(1H, brs) |
| A-544 | 8.84(1H, d), 8.69(1H, s), 7.56(1H, d), 4.10-4.25(2H), 1.34(3H, d), 1.21(3H, d) |
| A-564 | 8.82(1H, d), 8.67(1H, s), 7.50-7.57(3H), 7.15-7.26(3H), 4.65(1H, m), 1.03(6H, d) |
| A-605 | 1.10(6H, d), 3.3-3.5(2H, m), 3.8-4.0(2H, m), 4.3-4.5(1H, m), 7.54(1H, d), 8.79(1H, s), 8.80(1H, d) |
| A-626 | 8.88(1H, d), 8.73(1H, s), 7.60(1H, d), 6.41(1H, brs), 1.17(9H, s) |
| A-691 | 8.82(1H, d), 8.65(1H, s), 7.53(1H, d), 3.95(2H, t), 3.58(2H, t), 1.36(9H, s) |

TABLE 10-continued

1H-NMR spectral details for representative Examples from the above Tables.
Nmr spectra were measured in deuterochloroform unless otherwise stated.

| Cpd | 1H-NMR |
|---|---|
| A-697 | 8.82(1H, d), 8.75(1H, brs), 8.71(1H, s), 7.56(1H, s), 5.75(2H, m), 5.19-5.30(4H), 3.29(4H, d) |
| A-713 | 8.97(1H, s), 8.84(1H, d), 8.73(1H, s), 7.57(1H, d), 5.79(1H, m), 5.26(1H, d), 5.24(1H, d), 4.11(2H, d), 3.78(3H, s) |
| A-736 | 8.83(1H, d), 8.69(1H, s), 7.45-7.58(5H), 7.24-7.28(2H), 5.78(1H, m), 5.12(1H, d), 5.08(1H, d), 4.17(2H, d), |
| A-737 | 8.84(1H, d), 8.71(1H, s), 7.55-7.62(2H), 7.27-7.45(3H), 5.80(1H, m), 5.09(1H, d), 5.06(1H, d), 4.49(1H, dd), 3.81(1H, dd) |
| A-738 | 8.84(1H, d), 8.70(1H, s), 7.57(1H, d), 7.43-7.45(2H), 7.24-7.28(1H9, 7.16(1H, dd), 5.77(1H, m), 5.14(1H, d), 5.10(1H, d), 4.16(2H, d |
| A-744 | 8.81(1H, d), 8.69(1H, s), 7.68(1H, d), 7.34(1H, t), 6.88-6.95(3H), 5.77(1H, m), 5.05(1H, d), 5.02(1H, d), 4.19(2H, d), 3.80(3H, s) |
| A-745 | 8.83(1H, d), 8.68(1H, s), 7.56(1H, d), 7.15(2H, d), 6.98(2H, d), 5.76(1H, m), 5.10(1H, d), 5.06(1H, d), 4.12(2H, d), 3.86(3H, s) |
| A-747 | 8.85(1H, d), 8.70-8.721(2H), 7.72(1H, d), 7.28(1H, t), 6.82-6.89(3H), 5.82(1H, m), 5.03-5.14(2H), 4.20(2H, d) |
| A-748 | 8.80(!h, d), 8.68(1H, s), 7.84(1H, s), 7.59(1H, d), 7.07(2H, d), 6.89(2H, d), 5.77(1H, m), 5.00-5.30(2H), 4.11(2H, d) |
| A-798 | 4.61(2H, s), 7.2-7.4(5H, m), 7.54(1H, d), 8.54(1H, s), 8.62(1H, d), 9.18(1H, brs), 10.38(1H, brs) |
| A-799 | 8.95(1H, s), 8.86(1H, d), 8.73(1H, s), 7.57(1H, d), 7.24-7.36(5H), 4.65(2H, s), 3.68(3H, s) |
| A-805 | 8.80(1H, d), 8.45(1H, s), 7.53(1H, d), 7.23-7.41(10H), 4.75(2H, s), 4.64(2H, s) |
| A-822 | 8.86(1H, d), 8.71(1H, s), 7.58(2H), 7.42(3H), 7.24(3H), 7.04-7.11(4H), 4.76(2H, s) |
| A-861 | 9.30(1H, s), 8.81(1H, d), 8.73(1H, s), 7.55(1H, d), 4.38(1H, m), 3.83(1H, d), 3.03(1H, t), 1.50-1.75(6H), 1.22(3H, d) |
| A-862 | 3.3-3.5(2H, m), 3.6-3.8(2H, m), 4.47(2H, s), 7.1-7.4(5H, m), 7.57(1H, d), 8.73(1H, s), 8.79(1H, d) |
| A-864 | 8.79(1H, d), 8.72(1H, s), 7.56(1H, d), 4.45(1H, brs), 3.20-3.80(4H), 1.90-2.10(2H) |
| A-865 | 8.84(1H, d), 8.74(1H, s), 8.42(1H, brs), 7.57(1H, d), 5.87(2H, brd), 4.33(2H, s), 4.18(2H, s) |
| A-866 | 11.32(1H, brs), 9.18(1H, s), 9.05(1H, d), 7.97(1H, d), 7.96(1H, d), 7.94(1H, d), 7.47(1H, t), 7.33(1H, t) |
| A-867 | 8.86(1H, d), 8.78(1H, s), 7.71(1H, d), 7.25-7.45(10H) |
| A-869 | 3.6-3.9(4H, m), 7.2-7.6(6H, m), 8.67(1H, d), 8.79(1H, m) |
| A-871 | 1.7-2.2(4H, m), 3.2-3.7(4H, m), 7.56(1H, d), 8.73(1H, s), 8.81(1H, d), 9.11(1H, brs) |
| A-872 | 1.5-1.8(6H, m), 3.3-3.6(4H, m), 7.56(1H, d), 8.75(1H, s), 8.83(1H, d), 8.93(brs) |
| A-873 | 3.4-3.6(4H, m), 3.6-3.9(4H, m), 7.58(1H, d), 8.03(1H, brs), 8.76(1H, s), 8.86(1H, d) |
| A-874 | 2.6-2.8(4H, m), 4.7-4.9(4H, m), 7.59(1H, d), 8.77(1H, s), 8.86(1H, d) |
| B-37 | 4.85(2H, d), 7.2-7.5(5H, m), 7.62(1H, d), 8.85(1H, s), 8.92(1H, d), 9.74(1H, brs), 10.61(1H, brs) |
| B-40 | 10.83(1H, s), 8.95(1H, d), 8.91(1H, s), 8.78(1H, s), 7.65(1H, d), 7.25-7.67(5H), 1.91(6H) |
| B-47 | 10.58(1H), 9.14(1H, s), 8.97(1H, d), 8.90(1H, s), 7.67(1H, d), 7.24-7.38(4H), 4.86(2H, d) |
| B-64 | 3.84(3H, s), 7.79(1H, d), 8.84(1H, s), 8.93(1H, d), 10.78(1H, brs) |
| B-65 | 12.41(1H, s), 10.66(1H, s), 8.93(1H, d), 8.87(1H, d), 7.70(1H, d), 4.07(2H, q), 1.16(3H, t) |
| B-71 | 12.14(1H, s), 9.22(1H, s), 8.98(1H, d), 8.92(1H, s), 7.68(1H, d), 1.43(9H, s) |
| B-74 | 12.53(1H, s), 10.79(1H, s), 9.00(1H, s), 8.95(1H, d), 7.79(1H, d), 6.02(1H, m), 5.38(1H, d), 5.28(1H, d), 4.60(2H, d) |
| B-86 | 12.22(1H, s), 9.22(1H, brs), 8.95(1H, d), 8.86(1H, s), 7.66(1H, d), 7.37-7.44(5H), 5.14(2H, s) |
| B-100 | 2.84(1H, brs), 3.36(1H, brs), 7.87(1H, d), 8.28(1H, brs), 9.03(1H, d), 9.17(1H, s) |
| B-108 | 5.40(2H, s), 7.2-7.5(5H, m), 7.71(1H, d), 8.9-9.1(2H, m), 12.80(1H, brs) |
| B-109 | 6.8-7.1(4H, m), 7.3-7.4(1H, m), 7.65(1H, d), 8.90(1H, s), 8.96(1H, d), 8.49(1H, brs), 11.82(1H, d) |
| B-149 | 12.34(1H, s), 10.95(1H, brs), 9.14(1H, s), 9.02(1H, d), 7.86(1H, d), 7.81(2H, d), 7.44(2H, t), 7.29(1H, m) |
| B-150 | 12.35(1H, s), 11.15(1H, brs), 9.16(1H, s), 9.03(1H, d), 8.34(1H, t), 7.87(1H, d), 7.25-7.35(3H) |
| B-151 | 12.45(1H, s), 9.14(1H, s), 9.02(1H, d), 7.49(1H), 7.47(1H, d), 7.46-7.50(2H), 7.07(1H, m) |
| B-152 | 12.25(1H, s), 11.03(1H, brs), 9.12(1H, s), 9.02(1H, d), 7.86(1H, d), 7.78(2H, t), 7.21(2H, t) |
| B-155 | 9.09(1H, s), 8.98(1H, d), 7.83(1H, d), 7.78(2H, d), 7.44(2H, d) |
| B-158 | 9.13(1H, s), 9.02(1H, d), 7.87(1H, d), 7.79(2H, d), 7.62(2H, d) |

TABLE 10-continued

1H-NMR spectral details for representative Examples from the above Tables.
Nmr spectra were measured in deuterochloroform unless otherwise stated.

| Cpd | 1H-NMR |
|---|---|
| B-163 | 7.5-7.6(2H, m), 7.67(1H, d), 7.8-7.9(1H, m), 8.01(1H, d), 8.91(1H, s), 8.95(1H, s), 9.82(1H, brs), 12.25(1H, brs) |
| B-166 | 9.00(1H, s), 8.90(1H, d), 7.74(1H, d), 7.52(1H, d), 7.45(1H, s), 7.19(1H, t), 6.99(1H, d), 2.25(3H, s) |
| B-167 | 12.29(1H, s), 10.94(1H, brs), 9.13(1H, s), 9.01(1H, d), 7.86(1H, d), 7.66(2H, d), 7.25(2H, d), 2.34(3H, s) |
| B-168 | 3.97(3H, s), 6.9-7.3(3H, m), 7.88(1H, d), 8.8-8.9(1H, m), 9.03(1H, d), 9.15(1H, s), 10.95(1H, brs), 12.73(1H, brs) |
| B-169 | 3.83(3H, s), 6.8-6.9(1H, m), 7.2-7.4(2H, m), 7.6-7.7(1H, m), 7.86(1H, d), 9.01(1H, d), 9.13(1H, s), 10.97(1H, brs), 12.38(1H, brs) |
| B-170 | 3.79(3H, s), 6.95(2H, d), 7.63(2H, d), 7.83(1H, d), 8.98(1H, d), 9.08(1H, s), 10.93(1H, brs), 12.17(1H, brs) |
| B-176 | 9.14(1H, s), 9.03(1H, d), 8.12(2H, d), 7.88(1H, d), 7.85(2H, d) |
| B-184 | 12.35(1H, s), 10.96(1H, brs), 9.13(1H, s), 9.02(1H, d), 8.58(1H, s), 7.86(1H, d), 7.53(1H, s), 7.25(1H, t), 7.15(1H, t), 6.76(1H, d) |
| B-185 | 12.14(1H, s), 10.92(1H, brs), 9.12(1H, s), 9.20(1H, d), 8.54(1H, brs), 7.85(1H, d), 7.56(2H, d), 6.89(2H, d) |
| B-189 | 4.71(2H, s), 7.2-7.4(2H, m), 7.5-7.6(1H, m), 7.8-7.9(2H, m), 9.01(1H, d), 9.11(1H, s), 11.01(1H, brs), 12.13(1H, brs) |
| B-190 | 12.38(1H, s), 10.98(1H), 9.15(1H, s), 9.03(1H, d), 7.87(1H, d), 7.74(1H, d), 7.73(1H, s), 7.41(1H, t), 7.30(1H, d), 4.69(3H, s) |
| B-194 | 12.37(1H, brs), 9.13(1H, s), 9.03(1H, d), 7.92(2H, d), 7.87(1H, d), 7.42(2H, d) |
| B-209 | 9.99(1H, s), 9.18(1H, s), 9.04(1H, d), 8.48-8.55(3H), 7.88(1H, d) |
| B-247 | 7.5-8.0(6H, m), 8.99(1H, d), 9.01(1H, s), 10.64(1H, brs) |
| B-251 | 3.42(3H, s), 3.65(2H, t), 3.8-4.0(2H, m), 7.66(1H, d), 8.89(1H, s), 8.96(1H, d), 9.22(1H, brs), 10.48(1H, brs) |
| B-255 | 0.91(3H, t), 1.3-1.5(2H, m), 1.5-1.7(2H, m), 1.9-2.1(2H, m), 3.46(3H, t), 3.56(3H, t), 3.81(2H, q), 7.66(1H, d), 8.89(1H, s), 8.97(1H, d), 9.02(1H, brs), 10.53(1H, brs) |
| B-257 | 1.99(3H, s), 7.88(1H, d), 8.97(1H, d), 8.99(1H, d), 10.92(1H, brs), 12.92(1H, brs) |
| B-258 | 7.5-7.7(3H, m), 7.86(1H, s), 7.9-8.1(2H, m), 9.02(1H, d), 9.14(1H, brs) |
| B-259 | 7.3-7.5(5H, m), 7.5-7.7(5H, m), 7.77(1H, d), 8.8-9.0(2H, m), 13.05(1H, brs) |
| B-261 | 1.8-2.0(2H, m), 3.76(2H, t), 3.8-3.9(2H, m), 7.66(1H, m), 8.99(1H, s), 8.95(1H, d), 9.44(1H, brs), 10.53(1H, brs) |
| B-267 | 9.08(1H, s), 9.01(1H, d), 7.84(1H, d), 1.95(6H, s) |
| B-269 | 10.38(1H, brs), 9.35(1H, s), 8.96(1H, d), 8.90(1H, s), 7.67(1H, d), 3.73(4H), 1.60-1.80(4H) |
| B-296 | 3.23(3H, s), 5.22(2H, s), 7.22-7.5(5H, m), 7.63(1H, d), 8.7-9.0(2H, m) |
| B-313 | 9.40(1H, s), 8.95(1H, d), 8.75(1H, s), 7.57(1H, d), 3.86(3H, s), 3.58(3H, s) |
| B-331 | 3.37(3H, s), 4.70(1H, s), 7.53(1H, d), 8.62(1H, s), 8.80(1H, d) |
| B-349 | 3.69(1H, s), 7.3-7.6(6H, m), 8.33(1H, brs), 8.51(1H, s), 8.79(1h, d) |
| B-353 | 8.81(1H, d), 8.52(1H, s), 8.52(1H, s), 7.53-7.60(2H), 7.25-7.46(3H), 3.62(3H, s) |
| B-354 | 10.13(1H), 8.88(1H, d), 8.48(1H, s), 7.72(1H, d), 7.37-7.55(4H), 3.75(3H, s) |
| B-355 | 8.84(1H, d), 8.57(1H, s), 8.15(1H, s), 7.56(1H, d), 7.43(2H, d), 7.27(2H, d), 3.68(3H, s) |
| B-366 | 8.81(1H, d), 8.58(1H, s), 8.14(1H, s), 7.54(1H, d), 7.37(1H, d), 7.25(1H), 7.10(2H), 3.65(3H, s), 2.42(3H, s) |
| B-369 | 8.47(1H, d), 8.03(1H, s), 7.33(1H, d), 7.02(1H, t), 6.54-6.64(3H), 3.45(3H, s), 3.32(3H, s) |
| B-373 | 8.87(1H, d), 8.62(1H, s), 8.35(1H, s9, 8.31(2H, d), 7.57(1H, d), 7.53(2H, d), 3.78(3H, s) |
| B-398 | 8.89(1H, d), 8.72(1H, s), 8.51(1H, d), 7.98(1H, dd), 7.73(1H, d), 7.58(1H, d), 7.31(1H, dd), 3.79(3H, s) |
| B-417 | 9.15(1H, s), 8.88(1H, d), 7.69(1H, d), 4.16(3H, s), 3.56(3H, s) |
| B-431 | 3.38(3H, s), 3.7-4.2(4H, m), 7.5-7.7(1H, m), 8.7-9.0(2H, m), 10.35(1H, brs) |
| B-519 | 1.2-1.4(3H, m), 3.7-4.1(6H, m), 7.56(1H, d), 8.6-9.0(2H, m), 10.85(1H, brs) |
| B-564 | 9.08(1H, brs), 8.36(1H, d), 7.51(1H, brs), 7.23(1H, d), 7.04-7.30(3H), 6.86-6.91(2H), 5.17(1H, d), 0.74(6H, d) |
| B-713 | 9.45(1H, s), 8.85(1H, d), 8.76(1H, s), 7.56(1H, d), 5.90(1H, m), 5.27-5.36(2H), 4.70(2H, d), 3.86(3H, s) |
| B-736 | 8.85(1H, s) 8.27(1H, s), 7.69(1H, d), 7.30-7.50(5H), 6.10(1H, m), 5.28(1H, d), 5.17(1H, d), 4.89(2H, d) |
| B-737 | 8.83(1H, d), 8.12(1H, s), 7.69(1H, d), 7.54-7.65(2H), 7.38-7.45(2H), 6.05(1H, m), 5.24(1H, d), 5.21(1H, d), 5.00(1H, dd), 4.73(1H, dd) |
| B-738 | 10.15(1H), 8.86(1H, d), 8.40(1H, s), 7.71(1H, d), 7.35-7.54(4H), 6.00(1H, m), 5.27(1H, d), 5.22(1H, d), 4.93(1H, d) |
| B-744 | 8.80(1H, d), 8.59(1H, s), 8.11(1H, s), 7.53(1H, d), 7.41(1H, t), 6.96(1H, dd), 6.84(1H, dd), 6.77(1H), 5.94(1H, m), 5.20(1H, d), 5.17(1H, d), 4.73(2H, d), 3.84(3H, s) |

TABLE 10-continued

1H-NMR spectral details for representative Examples from the above Tables.
Nmr spectra were measured in deuterochloroform unless otherwise stated.

| Cpd | 1H-NMR |
|---|---|
| B-745 | 8.80(1H, d), 8.67(1H, s), 8.13(1H, s), 7.53(1H, d), 7.17(2H, d), 6.98(2H, d), 5.93(1H, m), 5.17(1H, d), 5.14(1H, d), 4.72(2H, d), 3.85(3H, s) |
| B-747 | 8.79(1H, d), 8.51(1H, s), 8.34(1H, s), 7.56(1H, d), 7.33(1H, t), 7.26(1H, s), 6.87(1H, dd), 6.79(1H, dd), 6.74(1H, s), 5.91(1H, m), 5.21(1H, d), 5.17(1H, d), 4.73(2H, d) |
| B-748 | 9.69(1H, s), 8.80(1H, d), 7.96(1H, s), 7.66(1H, d), 7.19(2H, d), 6.86(2H, d), 5.93(1H, m), 5.12-5.25(2H), 4.89(2H, d) |
| B-799 | 10.45(1H, brs), 8.90(1H, d), 8.86(1H, s), 7.76(1H, d), 7.30-7.46(5H), 5.41(2H, s), 3.88(3H, s) |
| B-805 | 8.80(1H, d), 8.69(1H, s), 8.45(1H, s), 7.53(1H, d), 7.23-7.41(10H), 4.75(2H, s), 4.64(2H, s) |
| B-822 | 9.90(1H), 8.84(1H, d), 8.25(1H, s), 7.70(1H, d), 7.24-7.45(10H), 5.62(2H, s) |
| B-861 | 9.96(1H, brs), 8.95(1H, s), 8.93(1H, d), 7.79(1H, d), 5.40(1H, brs), 4.23(1H, brs), 3.34(1H) 1.60-1.94(6H), 1.33(3H, d) |
| B-863 | 8.86-8.95(2H), 7.65(1H, d), 5.62(1H), 3.85-4.35(4H), 2.35-2.65(2H) |
| B-864 | 8.93-8.98(2H), 7.79(1H, d), 4.75(1H), 3.70-4.00(4H), 1.95-2.25(2H) |
| B-865 | 8.93(2H), 8.42(1H, brs), 7.64(1H, d), 5.9(2H, m), 4.64(2H, s), 4.57(2H, s) |
| B-867 | 8.81(1H, d), 8.54(1H, s), 8.49(1H, s), 7.54(1H, d), 7.28-7.45(10H) |
| B-868 | 10.10(1H, s), 8.90(1H, d), 8.82(1H, s), 7.76(1H, d), 7.30-7.53(5H), 2.04(3H, s) |
| B-870 | 10.38(1H,), 9.37(1H, s), 8.96(1H, d), 8.89(1H, s), 7.67(1H, d), 4.30(2H), 3.74(2H), 3.04(3H, s), 1.85-1.90(4H) |
| B-871 | 1.9-2.2(4H, m), 3.7-4.0(4H, m), 7.62(1H, d), 8.8-9.0(2H, m) |
| B-872 | 1.6-1.9(6H, m), 3.6-3.8(2H, m), 4.0-4.3(2H, m), 7.63(2h, d), 8.87(1H, brs), 8.9-9.0(2H, m) |
| B-873 | 3.5-4.5(6H, m), 7.64(1H, d), 8.56(1H, brs), 8.92(1H, s), 8.94(1H, d) |
| B-874 | 8.94(1H, d), 8.93(1H, d), 7.65(1H, d), 4.40(2H, brs), 4.02(2H, brs), 2.86(4H) |
| B-877 | 3.07(2H, dt), 3.96(2H, t), 7.06(1H, s), 7.74(1H, d), 8.73(1H, s), 8.87(1H, d) |
| B-880 | 1.87(6H, d), 7.2-7.8(6H, m), 8.77(1H, s), 8.83(1H, d) |
| C-10 | 3.08(3H, s), 4.57(2H, s), 7.2-7.5(5H, m), 7.64(1H, d), 8.72(1H, s), 8.89(1H, d), 9.34(1H, brs) |
| C-78 | 3.10(3H, s), 3.26(3H, d), 4.5-4.8(2H, m), 7.1-7.5(5H, m), 7.64(1H, d), 8.72(1H, s), 8.90(1H, d), 9.34(1H, brs) |
| C-85 | 3.02(3H, s), 3.34(3H, s), 3.64(3H, s), 7.58(1H, d), 8.65(1H, d), 8.81(1H, d) |
| C-91 | 2.88(3H, s), 2.98(3H, s), 4.72(2H, s), 7.30-7.43(5H), 7.59(1H, d), 8.52(1H, s), 8.80(1H, d) |
| D-85 | 1.33(1H, t), 2.98(3H, s), 3.61(3H, s), 3.87(1H, q), 7.60(1H, d), 8.67(1H, s), 8.82(1H, d) |
| D-86 | 1.2-1.4(6H, m), 3.7-4.0(4H, m), 7.59(1H, d), 8.67(1H, s), 8.81(1H, d) |
| E-85 | 2.97(3H, s), 3.59(3H, s), 4.42(2H, d), 5.28(1H, d), 5.32(1H, d), 5.98(1H, m), 7.61(1H, d), 8.68(1H, s), 8.83(1H, d) |
| E-87 | 3.00(3H, s), 4.25(2H, d), 4.37(2H, d), 5.2-5.5(4H, m), 5.7-6.1(2H, m), 7.61(1H, d), 8.68(1H, s), 8.82(1H, d) |
| F-85 | 2.35(1H, t), 3.09(3H, s), 3.68(3H, s), 4.64(2H, d), 7.62(1H, d), 8.68(1H, s), 8.85(1H, d) |
| F-88 | 2.37(1H, dd), 2.62(1H, dd), 3.12(3H, s), 4.50(2H, d), 4.61(2H, d), 7.63(1H, d), 8.73(1H, s), 8.86(1H, d) |
| G-35 | 4.66(2H, s), 4.75(2H, s), 7.24-7.42(10H), 7.43(1H, d), 8.46(1H, s), 8.83(1H, d) |
| G-85 | 2.81(3H, s), 3.08(3H, s), 5.06(2H, s), 7.26-7.32(3H), 7.45(2H, d), 7.59(1H, d), 8.70(1H, s), 8.82(1H, d) |
| G-91 | 2.71(3H, s), 4.29(2H, s), 4.71(2H, s), 7.0-7.1(2H, m), 7.2-7.6(8H, m), 7.58(1H, d), 8.56(1H, s), 8.80(1H, d) |
| G-126 | 4.31(2H, s), 4.38(2H, s), 4.71(2H, s), 6.89(2H, d), 7.07(2H), 7.17-7.39(11H), 7.50(1H, d), 8.39(1H, s), 8.58(1H, d) |
| H-85 | 2.96(3H, s), 3.64(3H, s), 3.81(3H, s), 4.59(2H, s), 7.62(1H, d), 8.80(1H, s), 8.85(1H, d) |
| H-89 | 3.08(3H, S), 3.74(3H, s), 3.77(3H, s), 4.48(2H, s), 4.60(2H, s), 7.64(1H, s), 8.84(1H, s), 8.87(1H, d) |
| H-91 | 2.90(3H, s), 3.69(3H, s), 4.76(2H, s), 7.24-7.45(5H), 7.64(1H, d), 8.80(1H, s), 8.85(1H, d) |
| I-85 | 1.60(3H, d), 3.63(3H, s), 3.80(3H, s), 5.30(1H, q), 7.58(1H, d), 8.78(1H, s), 8.84(1H, d) |
| S-2 | 0.87(3H, t), 1.4-1.7(2H, m), 3.17(2H, t), 3.54(2H, t), 4.06(2H, t), 7.54(1H, d), 8.65(1H, s), 8.81(1H, d) |
| S-3 | 1.15(6H, d), 3.49(2H, t), 3.9-4.2(3H, m), 7.54(1H, d), 8.66(1H, s), 8.81(1H, d) |
| S-7 | 1.34(9H, s), 3.58(2H, t), 3.96(2H, t), 7.53(1h, d), 8.65(1h, s), 8.81(1h, d) |
| S-15 | 3.40(2H, t), 4.01(2H, t), 4.53(2H, s), 7.1-7.4(5H, m), 7.57(1h, d), 8.69(1H, s), 8.83(1H, d) |
| S-18 | 4.00(2H, t), 4.18(2H, t), 7.1-7.5(5H, m), 7.57(1H, d), 8.70(1H, s), 8.83(1H, d) |

TABLE 10-continued

1H-NMR spectral details for representative Examples from the above Tables.
Nmr spectra were measured in deuterochloroform unless otherwise stated.

| Cpd | 1H-NMR |
|---|---|
| S-109 | 1.25(3H, q), 3.1-3.3(1H, d), 3.4-3.6(1H, m), 3.7-4.0(2H, m), 4.28(1H, d), 4.47(1H, d), 5.76(1H, d), 7.1-7.5(5H, m), 7.57(1H, d), 8.70(1H, s), 8.83(1H, d) |
| S-120 | 1.37(6H, d), 4.2-4.4(1H, m), 4.42(2H, s), 7.62(1H, d), 8.73(1H, s), 8.91(1H, d) |
| S-124 | 1.55(9H, s), 4.34(2H, s), 7.60(1H, d), 8.71(1H, s), 8.90(1H, d) |
| S-132 | 4.47(2H, s), 4.62(2H, s), 7.2-7.4(4H, m), 7.61(1H, d), 8.70(1H, s), 8.91(1H, d) |
| S-143 | 1.36(6H, d), 1.70(3H, d), 4.3-4.4(1H, m), 4.67(1H, q), 7.60(1H, d), 8.71(1H, s), 8.90(1H, d) |
| S-155 | 1.71(3H, d), 4.76(2H, s), 4.76(1H, q), 7.1-7.4(5H, m), 7.61(1H, d), 8.69(1H, s), 8.91(1H, d) |
| S-167 | 1.35(6H, d), 1.78(6H, s), 4.2-4.4(1H, m), 7.58(1H, d), 8.67(1H, s), 8.88(1h, d) |
| S-356 | 3.77(2H, t), 4.40(2H, t), 6.81(1H, brs), 7.54(1H, d), 8.65(1H, s), 8.82(1H, d) |
| S-357 | 0.94(3H, t), 1.34(1h, m), 1.60(1H, m), 3.63(2H, t), 3.76(2H, t), 4.23(2H, t), 7.51(1H, d), 8.62(1H, s), 8.79(1H, d) |
| S-548 | 3.69(2H, t), 3.77(3h, s), 4.00(2H, t), 7.57(1H, d), 8.67(1H, s), 8.86(1H, d) |
| S-549 | 3.43(2H, t), 3.88(2H, t), 4.90(2H, s), 7.30-7.40(5H), 7.57(1H, d), 8.67(1H, s), 8.85(1H, d) |
| S-550 | 1.40(3H, d), 4.09(1H, m), 4.34(1H, m), 4.64(1H, m), 7.55(1H,, d), 8.78(1H, d), 9.14(1H, s), 9.47(1H, brs) |
| S-551 | 1.03(3H, t), 1.76(2H, m), 4.19(2H, m), 4.63(1H, m), 7.56(1H, d), 8.80(1H, d), 9.17(1H, s), 9.49(1H, brs) |
| S-552 | 0.88(3H, t), 1.80(2H, m), 3.82(1H, m), 4.17(1H, d), 4.30(1H, dd), 4.63(1H, t), 5.12(1H, d), 7.23-7.38(5H), 7.53(1H, d), 8.75(1H, d), 9.10(1H, s) |
| S-553 | 4.38(1H, dd), 4.90(1H, t), 5.27((1H), 7.25-7.53(5H), 7.57(1H, d), 8.81(1H, d), 9.22(1H, s), 9.70(1H, brs) |
| S-554 | 2.67(3H, s), 3.90(1H, dd), 4.45(1H, dd), 4.65(1h, dd), 7.30(2H), 7.40-7.450(3H), 7.60(1H, d), 8.73(1H, s), 8.87(1H, d) |
| S-555 | 3.73(1H, d), 4.47(1H, t), 4.66(1H, t), 4.89(1H, t), 5.17(1H, d), 7.10-7.46(10H), 7.57(1H, d), 8.79(1H, d), 9.18(1H, s) |
| S-556 | 1.56(3H, d), 3.51(1H, dd), 4.02(1h, t), 4.95(1H, m), 7.54(1H, d), 8.78(1H, d), 9.15(1H, s), 9.32(1H, s) |
| S-557 | 3.90(1H, t), 4.32(1H, t), 5.80(1H, t), 7.38-7.46(5H), 7.57(1H, d), 8.81(1H, d), 9.21(1H, s), 9.42(1H, brs) |
| S-558 | 3.08(3H, s), 3.60(1H, dd), 4.06(1H, t), 5.78(1H, dd), 7.28-7.40(5H), 7.52(1H, d), 8.74(1H, d), 9.09(1H, s) |
| S-559 | 3.44(1H, dd), 3.89(1H, t), 4.60(1H, d), 4.73(1H, d), 5.76(1H, dd), 7.26-7.40(10H), 7.53(1H, d9, 8.76(1H, d), 9.13(1H, s) |
| U-3 | 8.80(1H, d), 8.66(1h, s), 7.54(1H, d), 4.29(2H, t), 4.05(2H, t), 1.18(6H, d) |
| U-7 | 8.78(1H, d), 8.66(1H, s), 7.52(1H, d), 4.28(2H, t), 4.00(2H, t), 1.34(9H, s) |
| U-20 | 8.81(1H, d), 8.67(1H, s), 7.55(1H, d), 7.25-7.50(5H), 4.66(2H, s), 4.00-4.17(4H) |
| W-194 | 1.45(18H, s), 7.54(1H, d), 7.75(1H, d), 9.08(1H, s), 10.17(1H, brs) |
| X-35 | 3.24(3H, d), 7.67(1H, d), 8.89(1H, s), 8.97(1H, d), 9.24(1H, brs), 10.32(1H, brs) |
| X-43 | 4.90(2H, d), 7.2-7.5(5H, m), 7.68(1H, d), 8.92(1H, s), 8.98(1H, d), 9.51(1H, brs), 10.62(1H, brs) |
| X-45 | 9.00(1H, s), 8.97(1H, d), 7.82(1H, d), 5.04(2H, q) |
| X-55 | 3.77(2H, t), 4.55(2H, t), 7.64(1H, d), 8.84(1H, s), 8.92(1H, d), 9.27(1H, brs) |

According to a further feature of the present invention there is provided a method for the control of pests at a locus which comprises the application of an effective amount of a compound of formula (I) or a salt thereof. For this purpose, the said compound is normally used in the form of a pesticidal composition (i.e. in association with compatible diluents or carriers and/or surface active agents suitable for use in pesticidal compositions), for example as hereinafter described.

The term "compound of the invention" as used hereinafter embraces a 3-pyridylcarboxamide of formula (I) as defined above and a pesticidally acceptable salt thereof.

One aspect of the present invention as defined above is a method for the control of pests at a locus. The locus includes, for example, the pest itself, the place (plant, field, forest, orchard, waterway, soil, plant product, or the like) where the pest resides or feeds, or a place susceptible to future infestation by the pest. The compound of the invention may therefore be applied directly to the pest, to the place where the pest resides or feeds, or to the place susceptible to future infestation by the pest.

As is evident from the foregoing pesticidal uses, the present invention provides pesticidally active compounds and methods of use of said compounds for the control of a number of pest species which includes: arthropods, especially insects or mites, or plant nematodes. The compound of the invention may thus be advantageously employed in practical uses, for example, in agricultural or horticultural crops, in forestry, in veterinary medicine or livestock husbandry, or in public health.

The compounds of the invention may be used for example in the following applications and on the following pests:

For the control of soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

In the protection of stored products, for example cereals, including grain or flour, groundnuts, animal feedstuffs, timber or household goods, e.g. carpets and textiles, compounds of the invention are useful against attack by arthropods, more especially beetles, including weevils, moths or mites, for example *Ephestia* spp. (flour moths), *Anthrenus* spp. (carpet beetles), *Tribolium* spp. (flour beetles), *Sitophilus* spp. (grain weevils) or *Acarus* spp. (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack on building by termites, for example, *Reticulitermes* spp., *Heterotermes* spp., *Coptotermes* spp.

In agriculture against adults, larvae and eggs of Lepidoptera (butterflies and moths), e.g. *Heliothis* spp. such as *Heliothis virescens* (tobacco budworm), *Heliothis armigera* and *Heliothis zea*. Against adults and larvae of Coleoptera (beetles) e.g. *Anthonomus* spp. e.g. *grandis* (cotton boll weevil), *Leptinotarsa decemlineata* (Colorado potato beetle), *Diabrotica* spp. (corn rootworms). Against Heteroptera (Hemiptera and Homoptera) e.g. *Psylla* spp., *Bemisia* spp., *Trialeurodes* spp., *Aphis* spp., *Myzus* spp., *Megoura viciae*, *Phylloxera* spp., *Nephotettix* spp. (rice leaf hoppers), *Nilaparvata* spp.

Against Diptera e.g. *Musca* spp. Against Thysanoptera such as *Thrips tabaci*. Against Orthoptera such as *Locusta* and *Schistocerca* spp., (locusts and crickets) e.g. *Gryllus* spp., and *Acheta* spp. for example, *Blatta orientalis*, *Periplaneta americana*, *Blatella germanica*, *Locusta migratoria migratorioides*, and *Schistocerca gregaria*. Against Collembola e.g. *Periplaneta* spp. and *Blatella* spp. (roaches). Against arthropods of agricultural significance such as Acari (mites) e.g., *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp., *Tetranychus* spp., *Eotetranychus* spp., *Oligonychus* spp., *Eutetranychus* spp.

From the order of the Isopoda, for example, *Oniscus aselus*, *Armadium vulgare*, *Porcellio scaber*.

Against nematodes which attack plants or trees of importance to agriculture, forestry or horticulture either directly or by spreading bacterial, viral, *mycoplasma* or fungal diseases of the plants. The plant-parasitic nematodes which can be controlled in accordance with the invention include, for example, the root-parasitic soil-dwelling nematodes such as, for example, those of the genera *Meloidogyne* (root knot nematodes, such as *Meloidogyne incognita*, *Meloidogyne hapla* and *Meloidogyne javanica*), *Heterodera* and *Globodera* (cyst-forming nematodes, such as *Globodera rostochiensis*, *Globodera pallida*, *Heterodera trifolii*) and of the genera *Radopholus*, such as *Radopholus similis*, *Pratylenchus* such as *Pratylenchus neglectus*, *Pratylenchus penetrans* and *Pratylenchus curvitatus*; *Tylenchulus* such as *Tylenchulus semipenetrans*, *Tylenchorhynchus*, such as *Tylenchorhynchus dubius* and *Tylenchorhynchus claytoni*, *Rotylenchus* such as *Rotylenchus robustus*, *Heliocotylenchus* such as *Haliocotylenchus multicinctus*, *Belonoaimus* such as *Belonoaimus longicaudatus*, *Longidorus* such as *Longidorus elongatus*, *Trichodorus* such as *Trichodorus primitivus* and *Xiphinema* such as *Xiphinema index*.

Other nematode genera which can be controlled using the compounds according to the invention are *Ditylenchus* (stem parasites, such as *Ditylenchus dipsaci* and *Ditylenchus destructor*), *Aphelenchoides* (foliar nematodes, such as *Aphelenchoides ritzemabosi*) and *Anguina* (seed nematodes, such as *Anguina tritici*).

In the field of veterinary medicine or livestock husbandry or in the maintenance of public health against arthropods which are parasitic internally or externally upon vertebrates, particularly warm-blooded vertebrates, for example domestic animals, e.g. cattle, sheep, goats, equines, swine, poultry, dogs or cats, for example Acarina, including ticks (e.g. *Ixodes* spp., *Boophilus* spp. e.g. *Boophilus microplus*, *Rhipicephalus* spp. e.g. *Rhipicephalus appendiculatus Ornithodorus* spp. (e.g. *Ornithodorus moubata*) and mites (e.g. *Damalinia* spp.); fleas; Diptera (e.g. *Aedes* spp., *Anopheles* spp., *Musca* spp., *Hypoderma* spp.); Hemiptera; Dictyoptera (e.g. *Periplaneta* spp., *Blatella* spp.); Hymenoptera; for example against infections of the gastro-intestinal tract caused by parasitic nematode worms, for example members of the family Trichostrongylidae.

From the class of the helminths, for example, *Haemonchus*, *Trichostrongulus*, *Ostertagia*, *Cooperia*, *Chabertia*, *Strongyloides*, *Oesophagostomum*, *Hyostrongulus*, *Ancylostoma*, *Ascaris* and *Heterakis* and also *Fasciola*.

From the class of the Gastropoda, for example, *Deroceras* spp., *Arion* spp., *Lymnaea* spp., *Galba* spp., *Succinea* spp., *Biomphalaria* spp., *Bulinus* spp., *Oncomelania* spp.

From the class of the *Bivalva*, for example, *Dreissena* spp.

In practical use for the control of arthropods, especially insects or acarids, or nematode pests of plants, a method, for example, comprises applying to the plants or to the medium in which they grow an effective amount of a compound of the invention. For such a method, the compound of the invention is generally applied to the locus in which the arthropod or nematode infestation is to be controlled at an effective rate in the range of about 2 g to about 1 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. Preferably an effective rate range of the active compound is from about 10 g/ha to about 400 g/ha, more preferably from about 50 g/ha to about 200 g/ha.

When a pest is soil-borne, the active compound generally in a formulated composition, is distributed evenly over the area to be treated (ie, for example broadcast or band treatment) in any convenient manner and is applied at rates from about 10 g/ha to about 400 g ai/ha, preferably from about 50 g/ha to about 200 g ai/ha. When applied as a root dip to seedlings or drip irrigation to plants the liquid solution or suspension contains from about 0.075 to about 1000 mg ai/l, preferably from about 25 to about 200 mg ai/l. Application may be made, if desired, to the field or crop-growing area generally or in close proximity to the seed or plant to be protected from attack. The compound of the invention can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting.

The compound of the invention and methods of control of pests therewith are of particular value in the protection of field, forage, plantation, glasshouse, orchard or vineyard crops, of ornamentals, or of plantation or forest trees, for example: cereals (such as wheat or rice), cotton, vegetables (such as peppers), field crops (such as sugar beets, soybeans or oil seed rape), grassland or forage crops (such as maize or sorghum), orchards or groves (such as of stone or pit fruit or citrus), ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compound of the invention and methods of use thereof are of particular value in the control of arthropods or helminths which are injurious to, or spread or act as vectors of diseases domestic animals, for example those hereinbefore mentioned, and more especially in the control of ticks, mites, lice, fleas, midges, or biting, nuisance or myiasis flies. The compounds of the invention are particularly useful in controlling arthropods or helminths which are present inside domestic host animals or which feed in or on the skin or suck the blood of the animal, for which purpose they may be administered orally, parenterally, percutaneously or topically.

The compositions hereinafter described for application to growing crops or crop growing loci or as a seed dressing may, in general, alternatively be employed in the protection of stored products, household goods, property or areas of the general environment. Suitable means of applying the compounds of the invention include: to growing crops as foliar sprays (for example as an in-furrow spray), dusts, granules, fogs or foams or also as suspensions of finely divided or encapsulated compositions as soil or root treatments by liquid drenches, dusts, granules, smokes or foams; to seeds of crops via application as seed dressings by liquid slurries or dusts;

to animals infested by or exposed to infestation by arthropods or helminths, by parenteral, oral or topical application of compositions in which the active ingredient exhibits an immediate and/or prolonged action over a period of time against the arthropods or helminths, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems;

to the environment in general or to specific locations where pests may lurk, including stored products, timber, household goods, or domestic or industrial premises, as sprays, fogs, dusts, smokes, wax-smears, lacquers, granules or baits, or in tricklefeeds to waterways, wells, reservoirs or other running or standing water.

The compounds of the formula (I) can also be employed for controlling harmful organisms in crops of known genetically engineered plants or genetically engineered plants yet to be developed. As a rule, the transgenic plants are distinguished by especially advantageous properties, for example by resistances to particular crop protection agents, resistances to plant diseases or pathogens of plant diseases, such as particular insects or microorganisms such as fungi, bacteria or viruses. Other particular properties concern, for example, the harvested material with regard to quantity, quality, storage properties, composition and specific constituents. Thus, transgenic plants are known where the starch content is increased, or the starch quality is altered, or where the harvested material has a different fatty acid composition.

The use in economically important transgenic crops of useful plants and ornamentals is preferred, for example of cereals such as wheat, barley, rye, oats, millet, rice, cassava and maize or else crops of sugar beet, cotton, soya, oilseed rape, potatoes, tomatoes, peas and other types of vegetables.

When used in transgenic crops, in particular those which have resistances to insects, effects are frequently observed, in addition to the effects against harmful organisms to be observed in other crops, which are specific for application in the transgenic crop in question, for example an altered or specifically widened spectrum of pests which can be controlled, or altered application rates which may be employed for application.

The invention therefore also relates to the use of compounds of the formula (I) for controlling harmful organisms in transgenic crop plants.

According to a further feature of the present invention there is provided a pesticidal composition comprising one or more compounds of the invention as defined above, in association with, and preferably homogeneously dispersed in one or more compatible pesticidally acceptable diluents or carriers and/or surface active agents [i.e. diluents or carriers and/or surface active agents of the type generally accepted in the art as being suitable for use in pesticidal compositions and which are compatible with compounds of the invention].

In practice, the compounds of the invention most frequently form parts of compositions. These compositions can be employed to control arthropods, especially insects and acarids, or helminths such as plant nematodes. The compositions may be of any type known in the art suitable for application to the desired pest in any premises or indoor or outdoor area. These compositions contain at least one compound of the invention as the active ingredient in combination or association with one or more other compatible components which are for example, solid or liquid carriers or diluents, adjuvants, surface-active-agents, or the like appropriate for the intended use and which are agronomically or medicinally acceptable. These compositions, which may be prepared by any manner known in the art, likewise form a part of this invention.

The compounds of the invention, in their commercially available formulations and in the use forms prepared from these formulations may be present in mixtures with other active substances such as insecticides, attractants, sterilants, acaricides, nematicides, fungicides, growth regulatory substances or herbicides.

The pesticides include, for example, phosphoric esters, carbamates, carboxylic esters, formamidines, tin compounds and materials produced by microorganisms. p Preferred components in mixtures are:

1. from the group of the phosphorus compounds acephate, azamethiphos, azinphos-ethyl, azinphos-methyl, bromophos, bromophos-ethyl, cadusafos (F-67825), chlorethoxyphos, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, dimethoate, disulfoton, EPN, ethion, ethoprophos, etrimfos, famphur, fenamiphos, fenitriothion, fensulfothion, fenthion, flupyrazofos, fonofos, formothion, fosthiazate, heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosphocarb (BAS-301), phosmet, phosphamidon, phoxim, pirimiphos, pirimiphos-ethyl, pirimiphos-methyl, profenofos, propaphos, proetamphos, prothiofos, pyraclofos, pyridapenthion, quinalphos, sulprofos, temephos, terbufos, tebupirimfos, tetrachlorvinphos, thiometon, triazophos, trichlorphon, vamidothion;

2. from the group of the carbamates alanycarb (OK-135), aldicarb, 2-sec-butylphenyl methylcarbamate (BPMC), carbaryl, carbofuran, carbosulfan, cloethocarb, benfuracarb, ethiofencarb, furathiocarb, HCN-801, isoprocarb, methomyl, 5-methyl-m-cumenylbutyryl(methyl)carbamate, oxamyl, pirimicarb, propoxur, thiodicarb, thiofanox, 1-methylthio(ethylideneamino)-N-methyl-N-(morpholinothio)carbamate (UC 51717), triazamate;

3. from the group of the carboxylic esters acrinathrin, allethrin, alphametrin, 5-benzyl-3-furylmethyl (E)-(1R)-cis-2,2-dimethyl-3-(2-oxothiolan-3-ylidenemethyl)cyclopropanecarboxylate, beta-cyfluthrin, alpha-cypermethrin, beta-cypermethrin, bioallethrin, bioallethrin ((S)-cyclopentylisomer), bioresmethrin, bifenthrin, (RS)-1-cyano-1-(6-phenoxy-2-pyridyl)methyl(1RS)-trans-3-(4-tert-butylphenyl)-2,2-dimethylcyclopropanecarboxylate (NCI 85193), cycloprothrin, cyfluthrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), imiprothrin (S-41311), lambda-cyhalothrin, permethrin, phenothrin (® isomer), prallethrin, pyrethrins (natural products), resmethrin, tefluthrin, tetramethrin, theta-cypermethrin, tralomethrin, transfluthrin, zeta-cypermethrin (F-56701);

4. from the group of the amidines amitraz, chlordimeform;

5. from the group of the tin compounds cyhexatin, fenbutatin oxide;

6. others abamectin, ABG-9008, acetamiprid, acequinocyl, Anagrapha falcitera, AKD-1022, AKD-3059, ANS-118, azadirachtin, *Bacillus thuringiensis, Beauveria bassianea*, bensultap, bifenazate, binapacryl, BJL-932, bromopropylate, BTG-504, BTG-505, buprofezin, camphechlor, cartap, chlorobenzilate, chlorfenapyr, chlorfluazuron, 2-(4-chlorophenyl)-4,5-diphenylthiophene (UBI-T 930), chlorfentezine, chlorproxyfen, chromafenozide, clothianidine, 2-naphthylmethyl cyclopropanecarboxylate (Ro12-0470), cyromazin, diacloden (thiamethoxam), diafenthiuron, DBI-3204, ethyl 2-chloro-N-(3,5-dichloro-4-(1,1,2,3,3,3-hexafluoro-1-propyloxy)phenyl)carbamoyl)-2-carboximidate, DDT, dicofol, diflubenzuron, N-(2,3-dihydro-3-methyl-1,3-thiazol-2-ylidene)-2,4-xylidine, dihydroxymethyldihydroxypyrrolidine, dinobuton, dinocap, diofenolan, emamectin benzoate, endosulfan, ethiprole (sulfethiprole), ethofenprox, etoxazole, fenazaquin, fenoxycarb, fipronil, fluazuron, flumite (flufenzine, SZI-121), 2-fluoro-5-(4-(4-ethoxyphenyl)-4-methyl-1-pentyl) diphenyl ether (MTI 800), granulosis and nuclear polyhedrosis viruses, fenpyroximate, fenthiocarb, fluacrypyrim, flubenzimine, flubrocythrinate, flucycloxuron, flufenoxuron, flufenzine, flufenprox, fluproxyfen, gamma-HCH, halfenozide, halofenprox, hexaflumuron (DE_473), hexythiazox, HOI-9004, hydramethylnon (AC 217300), IKI-220, indoxacarb, ivermectin, L-14165, imidacloprid, indoxacarb (DPX-MP062), kanemite (AKD-2023), lufenuron, M-020, M-020, methoxyfenozide, milbemectin, NC-196, neemgard, nidinoterfuran, nitenpyram, 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), novaluron, pirydaryl, propargite, protrifenbute, pymethrozine, pyridaben, pyrimidifen, pyriproxyfen, NC-196, NC-1111, NNI-9768, novaluron (MCW-275), OK-9701, OK-9601, OK-9602, OK-9802, R-195, RH-0345, RH-2485, RYI-210, S-1283, S-1833, SI-8601, silafluofen, silomadine (CG-177), spinosad, spirodiclofen, SU-9118, tebufenozide, tebufenpyrad, teflubenzuron, tetradifon, tetrasul, thiacloprid, thiocyclam, thiamethoxam, tolfenpyrad, triazamate, triethoxyspinosyn A, triflumuron, verbutin, vertalec (mykotal), YI-5301.

The abovementioned components for combinations are known active substances, many of which are described in Ch. R Worthing, S. B. Walker, The Pesticide Manual, 12$^{th}$ Edition, British Crop Protection Council, Farnham 2000.

The effective use doses of the compounds employed in the invention can vary within wide limits, particularly depending on the nature of the pest to be eliminated or degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like. In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminium or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or colouring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulphoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, or sulphate, sulphonate or phosphate functional derivatives of the above compounds. The presence of at least one surface-active agent is generally essential when the active ingredient and/or the inert carrier are only slightly water soluble or are not water soluble and the carrier agent of the composition for application is water. Compositions of the invention may further contain other additives such as adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

For their agricultural application, the compounds of the invention are therefore generally in the form of compositions, which are in various solid or liquid forms. Solid forms of compositions which can be used are dusting powders (with a content of the compound of the invention, ranging up to 80%), wettable powders or granules (including water dispersible granules), particularly those obtained by extrusion, compacting, impregnation of a granular carrier, or granulation starting from a powder (the content of the compound of the invention, in these wettable powders or granules being between about 0.5 and about 80%). Solid homogenous or heterogenous compositions containing one or more compounds of the invention, for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (eg. low or ultra-low volume) depending upon the need or application technique. The compound or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble Some organic solids or inorganic salts may be dissolved in the carrier to help prevent settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient is thoroughly mixed in a suitable blender with additional substances which may be impregnated on the porous filler and is ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The rates and concentrations of the formulated compositions may vary according to the method of application or the nature of the compositions or use thereof. Generally speaking, the compositions for application to control arthropod or helminth pests usually contain from about 0.00001% to about 95%, more particularly from about 0.0005% to about 50% by weight of one or more compounds of the invention, or of total active ingredients (that is to say the compounds of the invention, together with other substances toxic to arthropods or helminths, synergists, trace elements or stabilizers). The actual compositions employed and their rate of application will be selected to achieve the desired effect(s) by the farmer, livestock producer, medical or veterinary practitioner, pest control operator or other person skilled in the art. Solid or liquid compositions for application topically to animals, timber, stored products or household goods usually contain from about 0.00005% to about 90%, more particularly from about 0.001% to about 10%, by weight of one or more compounds of the invention. For administration to animals orally or parenterally, including percutaneously solid or liquid compositions, these normally contain from about 0.1% to about 90% by weight of one or more compounds of the invention. Medicated feedstuffs normally contain from about 0.001% to about 3% by weight of one or more compounds of the invention. Concentrates or supplements for mixing with feedstuffs normally contain from about 5% to about 90%, preferably from about 5% to about 50%, by weight of one or more compounds of the invention. Mineral salt licks normally contain from about 0.1% to about 10% by weight of one or more compounds of formula (I) or pesticidally acceptable salts thereof.

Dusts or liquid compositions for application to livestock, goods, premises or outdoor areas may contain from about 0.0001% to about 15%, more especially from about 0.005% to about 2.0%, by weight, of one or more compounds of the invention. Suitable concentrations in treated waters are between about 0.0001 ppm and about 20 ppm, more particularly about 0.001 ppm to about 5.0 ppm. of one or more compounds of the invention, and may be used therapeutically in fish farming with appropriate exposure times. Edible baits may contain from about 0.01% to about 5%, preferably from about 0.01% to about 1.0%, by weight, of one or more compounds of the invention.

When administered to vertebrates parenterally, orally or by percutaneous or other means, the dosage of compounds of the invention, will depend upon the species, age, or health of the vertebrate and upon the nature and degree of its actual or potential infestation by arthropod or helminth pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 2A-2M illustrate compositions for use against arthropods, especially insects or acarids, or helminths such as plant nematodes, which comprise, as active ingredient, compounds of the invention, such as those described in preparative examples. The compositions described in EXAMPLES 2A-2M can each be diluted to give a sprayable compositon at concentrations suitable for use in the field. Generic chemical descriptions of the ingredients (for which all of the following percentages are in weight percent), used in the composition EXAMPLES 2A-2M exemplified below, are as follows:

| Trade Name | Chemical Description |
|---|---|
| Ethylan BCP | Nonylphenol ethylene oxide condensate |
| Soprophor BSU | Tristyrylphenol ethylene oxide condensate |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan $NO_2$ | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

Example 2A

A water soluble concentrate is prepared with the composition as follows:

| | |
|---|---|
| Active ingredient | 7% |
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

Example 2B

An emulsifiable concentrate (EC) is prepared with the composition as follows:

| | |
|---|---|
| Active ingredient | 25% (max) |
| Soprophor BSU | 10% |
| Arylan CA | 5% |
| N-methylpyrrolidone | 50% |
| Solvesso 150 | 10% |

The first three components are dissolved in N-methylpyrrolidone and to this is then added the Solvesso 150 to give the final volume.

Example 2C

A wettable powder (WP) is prepared with the composition as follows:

| | |
|---|---|
| Active ingredient | 40% |
| Arylan S | 2% |

-continued

| | |
|---|---|
| Darvan NO$_2$ | 5% |
| Celite PF | 53% |

The ingredients are mixed and ground in a hammer-mill to a powder with a particle size of less than 50 microns.

Example 2D

An aqueous-flowable formulation is prepared with the composition as follows:

| | |
|---|---|
| Active ingredient | 40.00% |
| Ethylan BCP | 1.00% |
| Sopropon T360. | 0.20% |
| Ethylene glycol | 5.00% |
| Rhodigel 230. | 0.15% |
| Water | 53.65% |

The ingredients are intimately mixed and are ground in a bead mill until a mean particle size of less than 3 microns is obtained.

Example 2E

An emulsifiable suspension concentrate is prepared with the composition as follows:

| | |
|---|---|
| Active ingredient | 30.0% |
| Ethylan BCP | 10.0% |
| Bentone 38 | 0.5% |
| Solvesso 150 | 59.5% |

The ingredients are intimately mixed and ground in a bead-mill until a mean particle size of less than 3 microns is obtained.

Example 2F

A water dispersible granule is prepared with the composition as follows:

| | |
|---|---|
| Active ingredient | 30% |
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

Example 2G

A dusting powder is prepared with the composition as follows:

| | |
|---|---|
| Active ingredient | 1 to 10% |
| Talc powder-superfine | 99 to 90% |

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

Example 2H

An edible bait is prepared with the composition as follows:

| | |
|---|---|
| Active ingredient | 0.1 to 1.0% |
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

Example 2I

A solution formulation is prepared with a composition as follows:

| | |
|---|---|
| Active ingredient | 15% |
| Dimethyl sulfoxide | 85% |

The active ingredient is dissolved in dimethyl sulfoxide with mixing and or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

Example 2J

A wettable powder is prepared with the composition as follows:

| | |
|---|---|
| Active ingredient | 50% |
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infection by arthropods, by spraying or dipping, or by oral administration in drinking water, to control the arthropods.

Example 2K

A slow release bolus composition is formed from granules containing the following components in varying percentages (similar to those described for the previous compositions) depending upon need:

| | |
|---|---|
| Active ingredient | |
| Density agent | |
| Slow-release agent | |
| Binder | |

The intimately mixed ingredients are formed into granules which are compressed into a bolus with a specific gravity of 2 or more. This can be administered orally to ruminant domestic animals for retention within the reticulo-rumen to give a continual slow release of active compound over an extended period of time to control infestation of the ruminant domestic animals by arthropods.

Example 2L

A slow release composition in the form of granules, pellets, brickettes or the like can be prepared with compositions as follows:

| | |
|---|---|
| Active ingredient | 0.5 to 25% |
| Polyvinyl chloride | 75 to 99.5% |
| Dioctyl phthalate (plasticizer) | |

The components are blended and then formed into suitable shapes by melt-extrusion or molding. These composition are useful, for example, for addition to standing water or for fabrication into collars or eartags for attachment to domestic animals to control pests by slow release.

Example 2M

A water dispersible granule is prepared with the composition as follows:

| | |
|---|---|
| Active ingredient | 85%(max) |
| Polyvinylpyrrolidone | 5% |
| Attapulgite clay | 6% |
| Sodium lauryl sulfate | 2% |
| Glycerine | 2% |

The ingredients are mixed as a 45% slurry with water and wet milled to a particle size of 4 microns, then spray-dried to remove water.

Methods of Pesticidal use

The following representative test procedures, using compounds of the invention, were conducted to determine the parasiticidal and pesticidal activity of compounds of the invention.

Method A:

Germinated field bean seeds (*Vicia faba*) with seed roots were transferred into brown glass bottles filled with tap water and then populated with about 100 black bean aphids (*Aphis fabae*). Plants and aphids were then dipped into an aqueous solution of the formulated preparation to be examined for 5 seconds. After they had drained, plants and animals were stored in a climatized chamber (16 hours of light/day, 25° C., 40-60% relative atmospheric humidity). After 3 and 6 days of storage, the effect of the preparation on the aphids was determined. At a concentration of 100 ppm (based on the content of active compound), the following Compounds caused a mortality of at least 50% among the aphids:

A-18, A-64, A-65, A-71, A-74, A-79, A-81, A-86, A-88, A-206, A-209, A-223, A-255, A-261, A-262, A-265, A-267, A-268, A-292, A-296, A-312, A-312, A-316, A-317, A-326, A-329, A-349, A-353, A-354, A-355, A-365, A-366, A-367, A-369, A-373, A-381, A-398, A-431, A-524, A-529, A-540, A-544, A-564, A-605, A-626, A-691, A-697, A-713, A-736, A-737, A-738, A-744, A-745, A-747, A-748, A-798, A-799, A-805, A-822, A-861, A-862, A-865, A-867, A-874, B-37, B-40, B-47, B-65, B-74, B-149, B-150, B-151, B-152, B-155, B-158, B-163, B-166, B-167, B-168, B-169, B-170, B-176, B-184, B-185, B-189, B-247, B-251, B-255, B-258, B-259, B-261, B-267, B-269, B-296, B-313, B-349, B-353, B-354, B-355, B-366, B-369, B-373, B-398, B-431, B-564, B-713, B-736, B-737, B-738, B-744, B-745, B-747, B748, B-799, B-805, B-822, B-861, B-863, B-864, B-865, B-867, B-869, B-870, B-871, B-873, B-874, B-877, C-85, E-85, F-85, F-88, H-85, S-548, S-550, S-551, S-552, S-553, S-555, S-556, S-558, S-559, U-3, U-7, U-20, X-45 and X-55.

Method B:

Germinated field bean seeds (*Vicia faba*) with seed roots were transferred into brown glass bottles filled with tap water. Four milliliters of an aqueous solution of the formulated preparation to be examined were pipetted into the brown glass bottle. The field bean was then heavily populated with about 100 black bean aphids (*Aphis fabae*). Plants and aphids were then stored in a climatized chamber (16 hours of light/day, 25° C., 40-60% relative atmospheric humidity). After 3 and 6 days of storage, the root-systemic effect of the preparation on the aphids was determined. At a concentration of 10 ppm (based on the content of active compound), the following Compounds caused a mortality of at least 80% among the aphids, by root-systemic action:

A-39, A-64, A-65, A-67, A-71, A-74, A-79, A-81, A-86, A-88, A-89, A-90, A-209, A-212, A-223, A-262, A-265, A-267, A-268, A-292, A-296, A-313, A-317, A-326, A-329, A-349, A-354, A-355, A-365, A-366, A-367, A-369, A-373, A-381, A-398, A-431, A-519, A-524, A-529, A-540, A-544, A-564, A-605, A-626, A-691, A-697, A-713, A-736, A-737, A-738, A-744, A-745, A-747, A-748, A-798, A-799, A-805, A-822, A-861, A-862, A-865, A-867, A-871, A-873, A-874, B-37, B-40, B-47, B-65, B-71, B-74, B-86, B-149, B-150, B-151, B-152, B-155, B-158, B-166, B-167, B-169, B-170, B-176, B-184, B-189, B-247, B-251, B-255, B-257, B-258, B-259, B-261, B-267, B-269, B-296, B-313, B-349, B-353, B-354, B-355, B-366, B-369, B-373, B-398, B-564, B-713, B-736, B-737, B-738, B-744, B-745, B-748, B-799, B-805, B-861, B-863, B-864, B-865, B-867, B-869, B-870, B-871, B-872, B-873, B-874, B-877, C-85, D-86, E-85, F-85, F-88, G-85, H-85, S-3, S-120, S-356, S-548, S-550, S-551, S-553, S-556, S-557, S-558, S-559, U-3, U-7, U-20, X-45 and X-55.

The invention claimed is:

1. A compound of the formula (I):

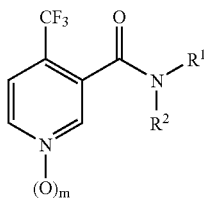

wherein:
R$^1$ is —C(=U)NR$^3$R$^4$;
R$^2$ is H, (C$_1$-C$_6$)alkyl or R$^3$;
R$^3$ is R$^5$, OH or NH$_2$; or is (C$_1$-C$_6$)alkyl substituted by one or more R$^6$ groups;
R$^4$ is H or R$^5$; or is (C$_1$-C$_6$)alkyl unsubstituted or substituted by one or more R$^6$ groups;
R$^5$ is (C$_3$-C$_6$)alkenyl, (C$_3$-C$_6$)alkynyl, (C$_3$-C$_8$)cycloalkyl, (C$_1$-C$_6$)alkoxy, (C$_3$-C$_6$)alkenyloxy, (C$_3$-C$_6$)alkynyloxy, (C$_1$-C$_6$)alkylamino, di-(C$_1$-C$_6$)alkylamino, CO(C$_1$-C$_6$)alkyl, NHCO(C$_1$-C$_6$)alkyl, NHSO$_2$(C$_1$-C$_6$)alkyl or SO$_2$(C$_1$-C$_6$)alkyl which last 12 mentioned groups are unsubstituted or substituted by one or more R$^6$ groups; or is (C$_3$-C$_8$)cycloalkyl-(C$_1$-C$_6$)alkyl which cycloalkyl group is unsubstituted or substituted by one or more R$^6$ groups; or is NH(CHR$^{14}$)$_s$aryl, —(CR$^{15}$R$^{16}$)$_p$aryl, O(R$^{15}$R$^{16}$)$_r$aryl, NHCOaryl, CO(CH$_2$)$_t$aryl, NHSO$_2$aryl, SO$_2$(CH$_2$)$_u$aryl or N=C(aryl)$_2$, which aryl groups are unsubstituted or substituted by one or more R$^{17}$ groups; or is O(CR$^{15}$R$^{16}$)$_p$(C$_3$-C$_8$)cycloalkyl or N=C[(C$_1$-C$_6$)alkyl]$_2$;
R$^6$ is halogen, (C$_1$-C$_6$)alkoxy, (C$_1$-C$_6$)haloalkoxy, S(O)$_n$R$^{14a}$, CN, CO$_2$(C$_1$-C$_6$)alkyl, CO$_2$H, NO$_2$, OH, amino, (C$_1$-C$_6$)alkylamino, di-(C$_1$-C$_6$)alkylamino, carbamoyl, (C$_1$-C$_6$)-alkylcarbamoyl, di-(C$_1$-C$_6$)-alkylcarbamoyl or CH[O(C$_1$-C$_6$)alkyl]$_2$; or is phenoxy unsubstituted or substituted by one or more R$^{14a}$ or halogen groups;
R$^{17}$ is R$^6$, R$^{14a}$ or CH$_2$OH;
U is S or O;
R$^{14}$, R$^{15}$ and R$^{16}$ are each independently H, (C$_1$-C$_6$)alkyl or (C$_1$-C$_6$)haloalkyl;
R$^{14a}$ is (C$_1$-C$_6$)alkyl or (C$_1$-C$_6$)haloalkyl;
m is zero or one;
n, p, r, s, t and u are each independently zero, one or two;
q is one, two or three;
or a pesticidally acceptable salt thereof;
with the exclusion of the compound wherein R$^1$ is —C(=U)NR$^3$R$^4$; U is O; R$^2$ is H; m is zero; R$^4$ is H and R$^3$ is 2,4-dichlorophenyl.

2. A compound or a salt thereof as claimed in claim 1, wherein R$^2$ is H or R$^3$.

3. A compound or a salt thereof as claimed in claim 1, wherein R$^3$ is R$^5$ or OH; or is (C$_1$-C$_6$)alkyl substituted by one or more R$^6$ groups.

4. A compound or a salt thereof as claimed in claim 1, wherein
R$^2$ is H;
R$^3$ is R$^5$ or OH; or is (C$_1$-C$_6$)alkyl substituted by one or more R$^6$ groups;
R$^4$ is H or R$^5$, or is (C$_1$-C$_6$)alkyl unsubstituted or substituted by one or more R$^6$ groups;
R$^5$ is (C$_3$-C$_6$)alkenyl, (C$_3$-C$_6$)alkynyl, (C$_3$-C$_8$)cycloalkyl, (C$_3$-C$_8$)cycloalkyl-(C$_1$-C$_6$)alkyl, (C$_1$-C$_6$)alkoxy, (C$_3$-C$_6$)alkenyloxy, (C$_3$-C$_6$)alkynyloxy or O(CR$^{15}$R$^{16}$)$_p$(C$_3$-C$_8$)cycloalkyl; or —(CR$^{15}$R$^{16}$)$_p$phenyl, O(CR$^{15}$R$^{16}$)$_r$phenyl which phenyl groups are unsubstituted or substituted by one or more R$^{17}$ groups;
R$^6$ is halogen, (C$_1$-C$_6$)alkoxy, (C$_1$-C$_6$)haloalkoxy, S(O)$_n$R$^{14a}$, CN, NO$_2$ or OH;
R$^{17}$ is R$^6$, R$^{14a}$ or CH$_2$OH;
U is S or O;
R$^{14}$, R$^{15}$ and R$^{16}$ are each H or (C$_1$-C$_6$)alkyl;
R$^{14a}$ is (C$_1$-C$_6$)alkyl or (C$_1$-C$_6$)haloalkyl;
m is zero;
n, r, s, t and u are zero, one or two;
q is one.

5. A compound or a salt thereof as claimed in claim 1, wherein
R$^2$ is H;
U is O or S;
R$^3$ is (C$_1$-C$_6$)alkoxy, C$_1$-C$_6$)haloalkoxy, (C$_3$-C$_6$)alkenyloxy, (C$_3$-C$_6$)alkynyloxy, CH$_2$phenyl or OCH$_2$phenyl, or phenyl, which phenyl groups are unsubstituted or substituted by one or more groups selected from halogen, (C$_1$-C$_6$)alkyl, (C$_1$-C$_6$)alkoxy, CN and NO$_2$;
R$^4$ is H, (C$_1$-C$_6$)alkyl, (C$_3$-C$_6$)alkenyl, (C$_3$-C$_6$)alkynyl or CH$_2$phenyl; and
m is zero.

6. A process for the preparation of a compound of formula (I) or a salt thereof as defined in claim 1, which process comprises:

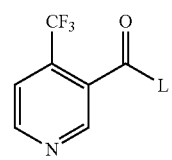

where R$^1$ is —C(=U)NR$^3$R$^4$, m is zero, R$^2$ is H, U is O, and R$^3$ and R$^4$ are as defined in formula (I), reacting a compound of formula (IX):

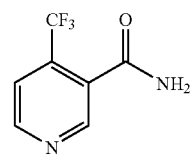

with oxalyl chloride or triphosgene, to give the corresponding acylisocyanate intermediate followed by reacting the resultant intermediate with an amine of formula (X):

      (X)

wherein R$^3$ and R$^4$ are as defined in formula (I); or
if desired, converting a resulting compound of formula (I) into a pesticidally acceptable salt thereof.

7. A pesticidal composition comprising a pesticidally effective amount of a compound of formula (I) or a pesticidally acceptable salt thereof as defined in claim 1, in association with a pesticidally acceptable diluent or carrier and/or surface active agent.

8. A method for the control of arthropod or nematode pests, said method comprising applying to said pests or to a locus at which they reside or feed or which is susceptible to infestation thereby, a pesticidally effective amount of a compound or salt thereof as claimed in claim 1.

9. A method for the control of arthropod or nematode pests, said method comprising applying to said pests or to a locus at which they reside or feed or which is susceptible to infestation thereby, a pesticidally effective amount of a composition as claimed in claim 7.

* * * * *